(12) United States Patent
Pfeifer et al.

(10) Patent No.: US 8,647,631 B2
(45) Date of Patent: Feb. 11, 2014

(54) PHARMACEUTICAL COMPOSITION OF AN ANTIGENIC TAU PEPTIDE RECONSTITUTED IN A LIPOSOME AND RELATED ANTIBODIES AND CELL LINES

(75) Inventors: Andrea Pfeifer, St.-Légier (CH); Andreas Muhs, Pully (CH); Fred Van Leuven, Linden (BE); Maria Pihlgren, Mont-sur-Lausanne (CH)

(73) Assignees: Katholieke Universiteit Leuven, Leuven (BE); AC Immune S.A., Lausanne (CH)

( * ) Notice: Subject to any disclaimer, the term of this patent is extended or adjusted under 35 U.S.C. 154(b) by 0 days.

(21) Appl. No.: 13/262,793

(22) PCT Filed: Apr. 1, 2010

(86) PCT No.: PCT/EP2010/054418
§ 371 (c)(1),
(2), (4) Date: Oct. 3, 2011

(87) PCT Pub. No.: WO2010/115843
PCT Pub. Date: Oct. 14, 2010

(65) Prior Publication Data
US 2012/0183599 A1 Jul. 19, 2012

(30) Foreign Application Priority Data
Apr. 3, 2009 (EP) ..................................... 09157303

(51) Int. Cl.
*A61K 39/385* (2006.01)
*A61K 38/10* (2006.01)
*A61K 39/00* (2006.01)
*A61K 9/127* (2006.01)

(52) U.S. Cl.
USPC ..................... 424/185.1; 424/194.1; 424/420; 424/450; 424/812; 514/17.7; 514/17.8

(58) Field of Classification Search
None
See application file for complete search history.

(56) References Cited

U.S. PATENT DOCUMENTS

| 5,843,779 A | 12/1998 | Vandermeeren et al. |
| 7,408,027 B1 | 8/2008 | Mandelkow et al. |

(Continued)

FOREIGN PATENT DOCUMENTS

| EP | 2 210 901 A1 | 7/2010 |
| WO | WO 96/20218 A1 | 7/1996 |

(Continued)

OTHER PUBLICATIONS

International Search Report and Written Opinion dated Apr. 3, 2012 in co-pending International Application No. PCT/EP2011/067604.

(Continued)

*Primary Examiner* — Jeffrey Stucker
*Assistant Examiner* — Adam M Weidner
(74) *Attorney, Agent, or Firm* — F. Brent Nix; Johnson, Marcou & Isaacs, LLC

(57) ABSTRACT

The present invention is related to methods and pharmaceutical compositions for the therapeutic and diagnostic use in the treatment of diseases and disorders which are caused by or associated with neurofibrillary tangles. In particular, the invention relates to pharmaceutical composition comprising an antigenic peptide, particularly an antigenic phospho-peptide mimicking a major pathological phospho-epitope of protein tau, for the therapeutic and diagnostic use in the treatment of tauopathies including Alzheimer's Disease.

15 Claims, 34 Drawing Sheets

(56) References Cited

U.S. PATENT DOCUMENTS

Figure 35:
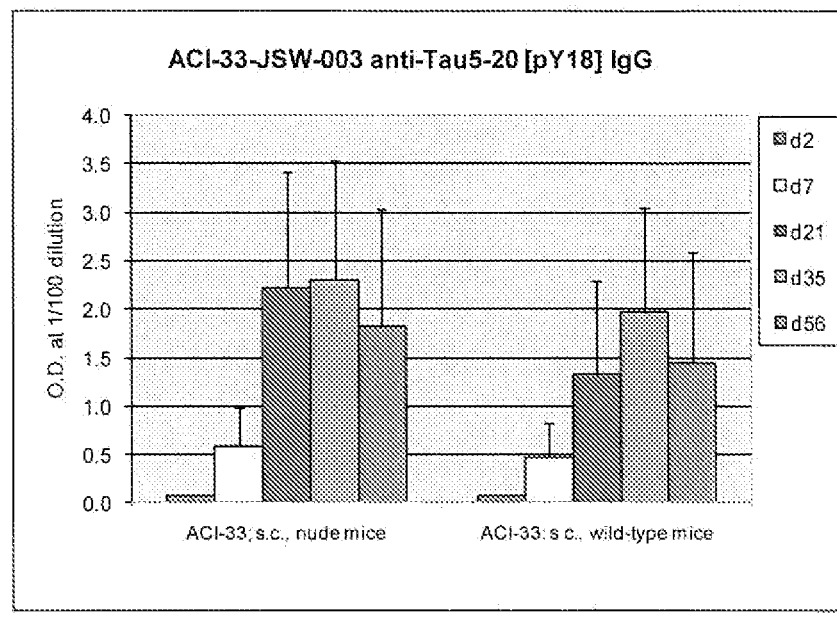

| | | | |
|---|---|---|---|
| 2002/0086009 | A1 | 7/2002 | Ishiguro et al. |
| 2004/0265920 | A1* | 12/2004 | Seubert et al. ............... 435/7.2 |
| 2005/0221391 | A1 | 10/2005 | Davies |
| 2005/0261475 | A1 | 11/2005 | Tseng et al. |
| 2006/0073158 | A1* | 4/2006 | Nicolau et al. ............ 424/185.1 |
| 2008/0050383 | A1 | 2/2008 | Sigurdsson et al. |
| 2008/0220449 | A1 | 9/2008 | Vasan et al. |

FOREIGN PATENT DOCUMENTS

| | | | |
|---|---|---|---|
| WO | WO 97/34145 | A1 | 9/1997 |
| WO | WO 98/22120 | A1 | 5/1998 |
| WO | WO 2005/080986 | A1 | 9/2005 |
| WO | WO 2005/081872 | A2 | 9/2005 |
| WO | WO 2007/068105 | A1 | 6/2007 |
| WO | WO 2007/068411 | A2 | 6/2007 |
| WO | WO 2010/106127 | A2 | 9/2010 |
| WO | WO 2010/115843 | A2 | 10/2010 |
| WO | WO 2010/144711 | A2 | 12/2010 |
| WO | WO 2011/013034 | A1 | 2/2011 |

OTHER PUBLICATIONS

Bhaskar, K. et al., "Tyrosine Phosphorylation of Tau Accompanies Disease Progression in Transgenic Mouse Models of Tauopathy," Neuropathology and Applied Neurobiology, Oct. 1, 2012, vol. 36, No. 6, pp. 462-477.

Hirata-Fukae, C. et al., "Levels of Soluble and Insoluble Tau Reflect Overall Status of Tau Phosphorylation in Vivo," Neuroscience Letters, Jan. 23, 2009, vol. 450, No. 1, pp. 51-55.

Hoffman, R. et al., "Unique Alzheimer's Disease Paired Helical Filament Specific Epitopes Involve Double Phosphorylation at Specific Sites," Biochemistry, Jul. 1, 1997, vol. 36, No. 26, pp. 8114-8124.

Jicha, "Camp-Dependent Protein Kinase Phosphorylations on Tau in Alzheimer's Disease," Journal of Neuroscience, Jan. 1, 1999, vol. 19, No. 17, p. 7486.

Lee, G. et al., "Phosphorylation of Tau by Fyn: Implications for Alzheimer's Disease," Journal of Neuroscience, Mar. 3, 2004, vol. 24, No. 9, pp. 2304-2312.

Lichtenberg-Kraag, B. et al., "Phosphorylation-Dependent Epitopes of Neurofilament Antibodies on Tau Protein and Relationship with Alzheimer Tau," Proceedings of the National Academy of Sciences of USA, Jun. 1, 1992, vol. 89, No. 12, pp. 5384-5388.

Oddo, S. et al., "Reduction of Soluble Abeta and Tau, but Not Soluble Abeta Alone, Ameliorates Cognitive Decline in Transgenic Mice with Plaques and Tangles," Journal of Biological Chemistry, Jan. 1, 2006, vol. 281, No. 51, pp. 39413-39423.

Otvos, L. et al., "Monoclonal Antibody PHF4 Recognizes Tau Protein Phosphorylated at Serine Residues 396 and 404," Journal of Neuroscience Research, Jan. 1, 1994, vol. 39, pp. 669-673.

Roder, H. et al., "Phosphorylation-Dependent Monoclonal Tau Antibodies Do Not Reliably Report Phosphorylation by Extracellular Signal-Regulated Kinase 2 at Specific Sites," Journal of Biological Chemistry, Feb. 14, 1997, vol. 272, No. 7, pp. 4509-4515.

Singer, D. et al., "Immuno-PCR-Based Quantification of Multiple Phosphorylated Tau-Epitopes Linked to Alzheimer's Disease," Analytical and Bioanalytical Chemistry, vol. 395, No. 7, Oct. 11, 2009, pp. 2263-2267.

Singer, D. et al., "Characterization of Phosphorylation Dependent Antibodies to Study the Phosphorylation Dependent Antibodies to Study the Phosphorylation Status of the Tau Protein," International Journal of Peptide Research and Therapeutics (formerly known as Letters in Pepdtide Science), Dec. 1, 2005, vol. 11, No. 4, pp. 279-289.

Torreilles, F. et al., "Binding Specificity of Monoclonal Antibody AD2: Influence of the Phosphorylation State of Tau," Molecular Brain Research, Jan. 1, 2000, vol. 78, pp. 181-185.

Vanhelmont, T. et al., "Serine-409 Phosphorylation and Oxidative Damage Define Aggregation of Human Protein Tau in Yeast," Fems Yeast Research, Dec. 1, 2010, vol. 10, No. 8, pp. 992-1005.

Zemlan, F. et al., "Monoclonal Antibody PHF-9 Recognizes Phosphorylated Serine 404 of Tau Protein and Labels Paired Helical Filaments," Journal of Neuroscience Research, Oct. 1, 1996, vol. 46, No. 1, pp. 90-97.

Zheng-Fischhoefer, Q. et al., "Sequential Phosphorylation of Tau by Glycogen Synthase Kinase-3beta and Protein Kinase A at Thr212 and Ser214 Generates the Alzheimer-Specific Epitope of Antibody AT100 and Requires a Paired-Helical-Filament-Like Conformation," European Journal of Biochemistry, Mar. 1, 1998, vol. 252, No. 3, pp. 542-552.

Asuni, A. et al., "Immunotherapy Targeting Pathological Tau Conformers in a Tangle Mouse Model Reduces Brain Pathology with Associated Functional Improvements," Journal of Neuroscience, Aug. 2007, pp. 9115-9129, vol. 27, No. 34.

Muhs, A. et al., "Liposomal Vaccines with Conformation-Specific Amyloid Peptide Antigens Define Immune Response and Efficacy in APP Transgenic Mice," Proceedings of the National Academy of Sciences of the United States of America, Jun. 2007, pp. 9810-9815, vol. 104, No. 23.

International Search Report and Written Opinion dated Oct. 1, 2010.

Tabira, T., "Immunization Therapy for Alzheimer Disease: A Comprehensive Review of Active Immunization Strategies," Tohoku J. Exp. Med., 2010, vol. 220, pp. 95-106.

Lewis, J. et al., "Neurofibrillary Tangles, Amyotrophy and Progressive Motor Disturbance in Mice 2 Expressing Mutant (P301L) Tau Protein," Aug. 2000, vol. 25, Nature America, Inc., pp. 402-405.

Masliah, E. et al., "Effects of α-Synuclein Immunization in a Mouse Model of Parkinson's Disease," Neuron, Jun. 16, 2005, vol. 46, pp. 857-868.

Muyllaert, D. et al., "Transgenic Mouse Models for Alzheimer's Disease: the Role of GSK-3β in Combined Amyloid and Tau-Pathology," Rev Neurol (Paris), 2006, vol. 162, No. 10, pp. 903-907.

Muyllaert, D. et al., "Glycogen Synthase Kinase-3β, or a Link Between Amyloid and Tau Pathology?" Genes, Brain and Behavior, 2008, vol. 7, Suppl. 1, pp. 57-66.

Nicolau, C. et al., "A Liposome-Based Therapeutic Vaccine Against β-Amyloid Plaques on the Pancreas of Transgenic Mice," PNAS, Feb. 19, 2012, vol. 99, No. 4, pp. 2332-2337.

Nicoll, J. et al., "Neuropathology of Human Alzheimer Disease After Immunization with Amyloid—β Peptide: A Case Report," Nature Medicine, Apr. 2003, vol. 9, No. 4, pp. 448-452.

Oddo, S. et al., "Aβ Immunotherapy Leads to Clearance of Early, but Not Late, Hyperphosphorylated Tau Aggregates via the Proteasome," Neuron, Aug. 5, 2004, vol. 43, pp. 321-332.

Ribé, E. et al., "Accelerated Amyloid Deposition, Neurofibrillary Degeneration and Neuronal Loss 10 in Double Mutant APP/TAU Transgenic Mice," Neurobiology of Disease, 2005, vol. 20, pp. 814-822.

Roberson, E. et al., "Reducing Endogenous Tau Ameliorates Amyloid β-Induced Deficits in an Alzheimer's Disease Mouse Model," Science, May 4, 2007, vol. 316 pp. 750-754.

Rosenmann, H. et al., "Tauopathy-Like Abnormalities and Neurologic Deficits in Mice Immunized with Neuronal Tau Protein," Arch Neurol, Oct. 2006, vol. 63, pp. 1459-1467.

Terwel, D. et al., "Amyloid Activates GSK-3β to Aggravate Neuronal Tauopathy in Bigenic Mice," The American Journal of Pathology, Mar. 2008, vol. 172, No. 3, pp. 786-798.

EPO Exam report issued in Application No. 10 713 172.4 mailed Feb. 7, 2013, pp. 1-8, Feb. 7, 2013.

Asuni et al., Immunotherapy Targeting Pathological Tau Conformers in a Tangle Mouse Model Reduces Brain Pathology with Associated Functional Improvements, *The Journal of Neuroscience*, pp. 9115-9129, Aug. 22, 2007.

Cussac, Yolaine (WIPO Authorized Officer), International Preliminary Report on Patentability in PCT/EP2010/053519, Oct. 4, 2011.

Dominguez et al., Novel Thereapeutic Strategies Provide the Real Test for the Amyloid Hypothesis of Alzheimer's Disease, *Trends in Pharmacological Sciences*, vol. 23 (7), Jul. 1, 2002.

(56) References Cited

OTHER PUBLICATIONS

Hermann, Patrice, International Search Report in PCT/EP2010/053519, pp. 1-11, Feb. 7, 2011.

Muhs et al., Liposomal Vaccines with Conformation-Specific Amyloid Peptide Antigens Define Immune Response and Efficacy in APP Transgenic Mice, *Proceedings of the National Academy of Sciences*, vol. 104, pp. 9810-9815, Jun. 5, 2007.

Sela et al., Therapeutic Vaccines: Realities of Today and Hopes for the Future, *Drug Discovery Today—Reviews/Therapeutic Focus*, vol. 7 (12), pp. 664-673, Jun. 1, 2002.

\* cited by examiner

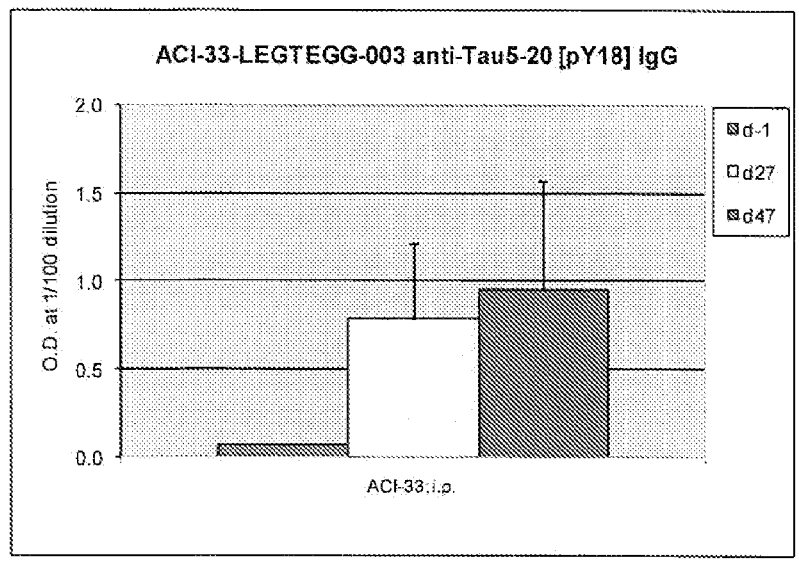
*FIGURE: 1a*
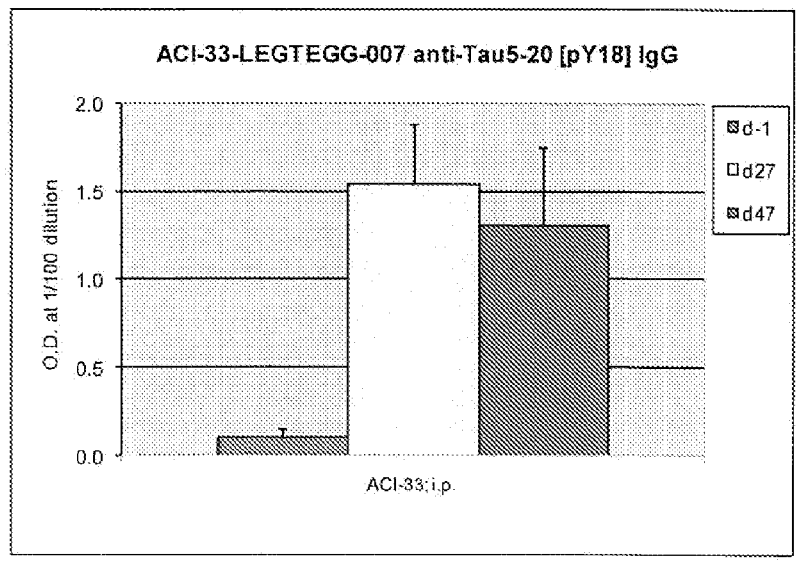
*FIGURE: 1b*

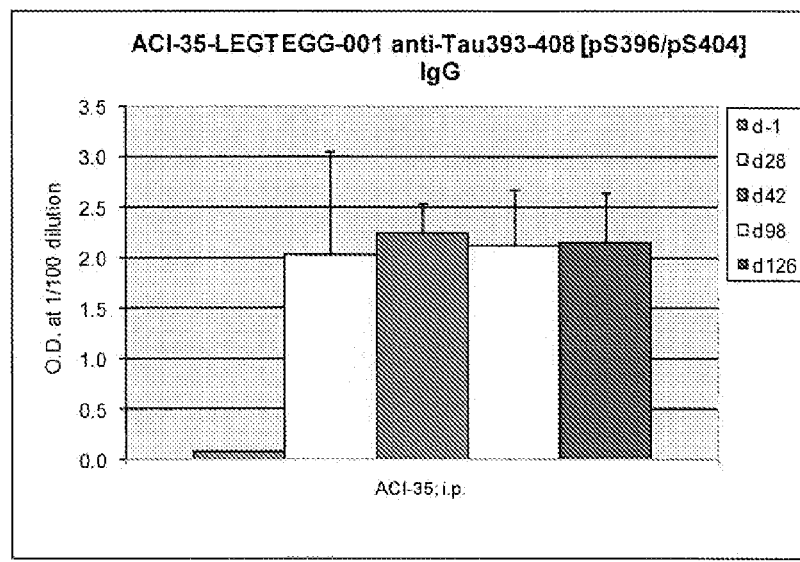
*FIGURE: 2a*
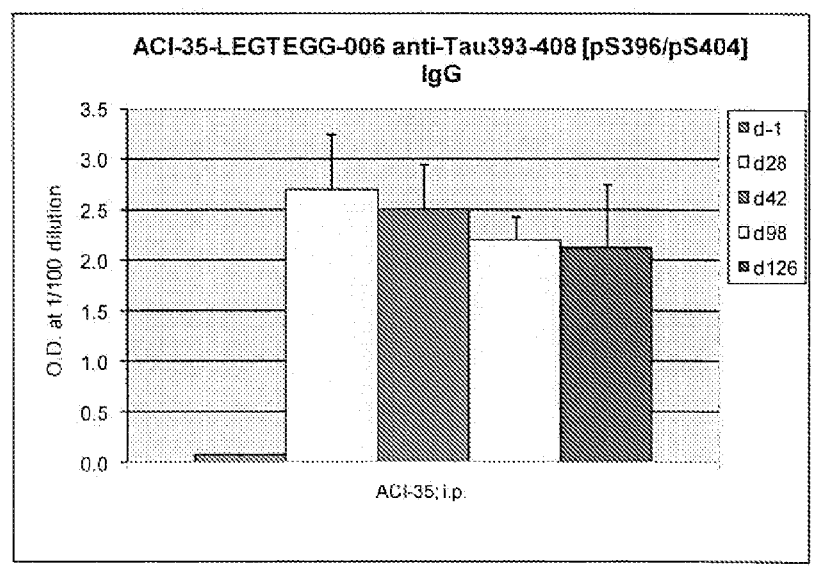
*FIGURE: 2b*

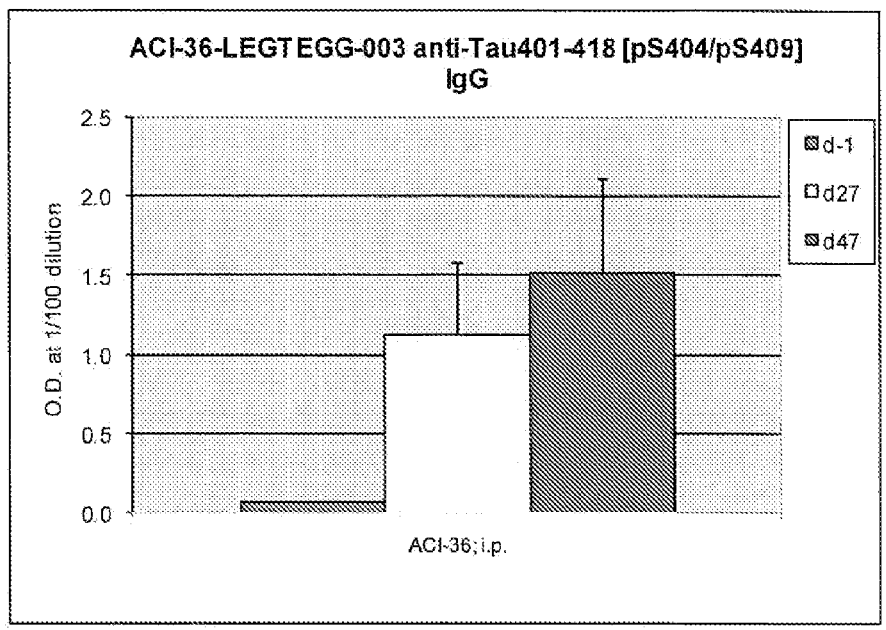
FIGURE: 3a
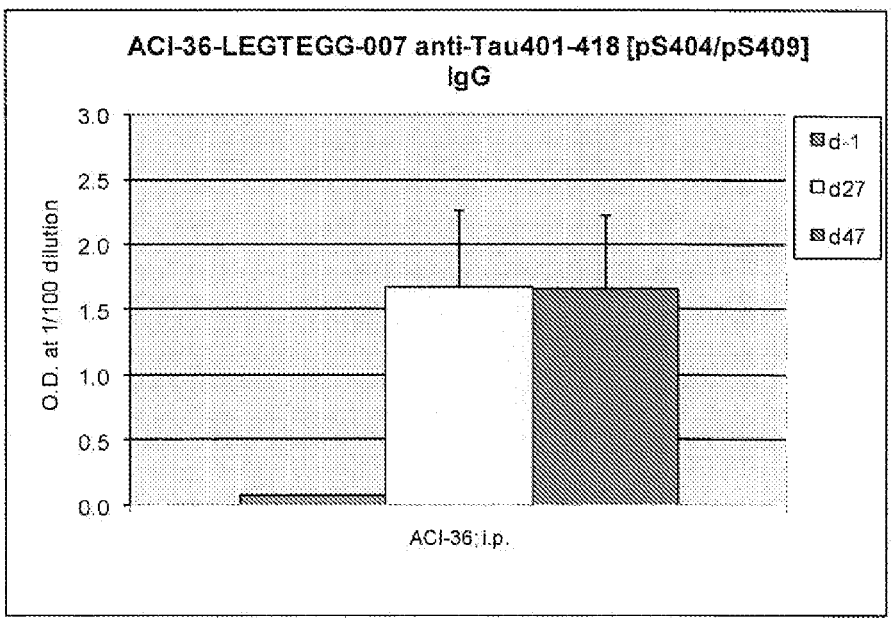
FIGURE: 3b

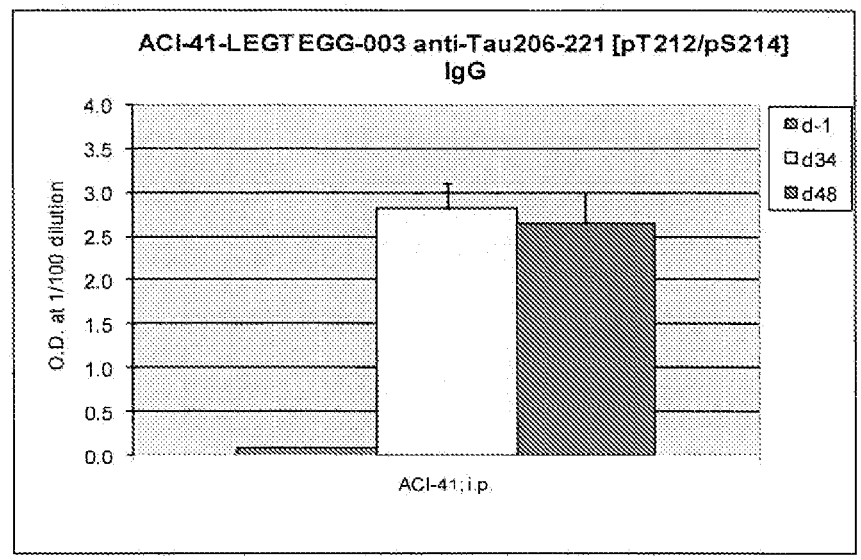
FIGURE: 4a
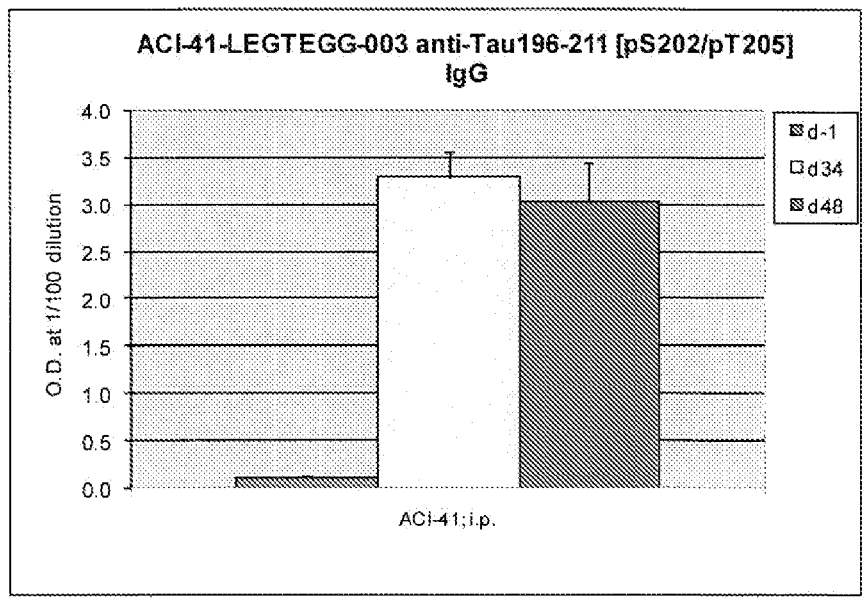
FIGURE: 4b

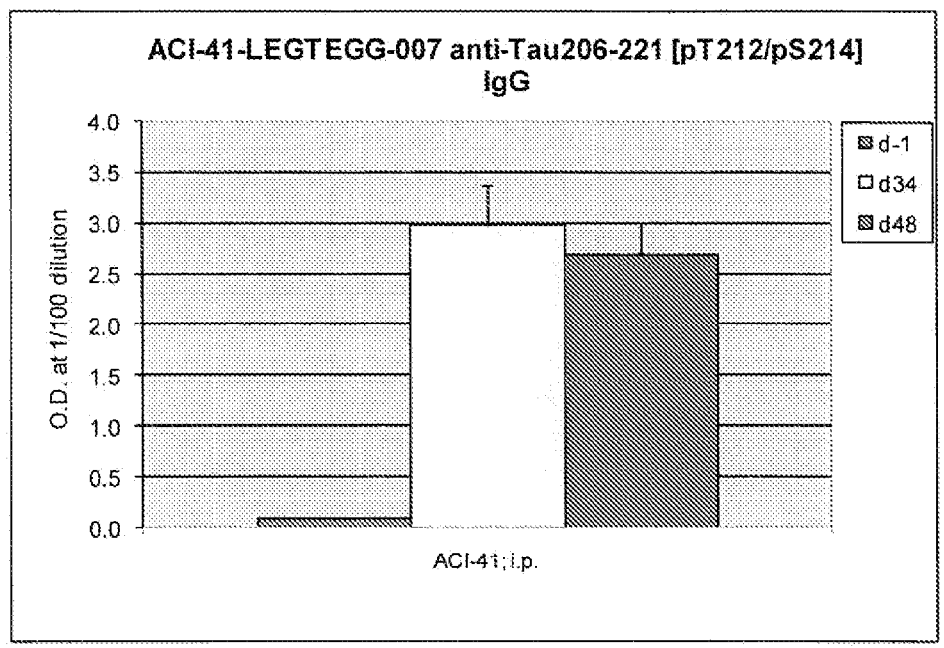
FIGURE: 4c
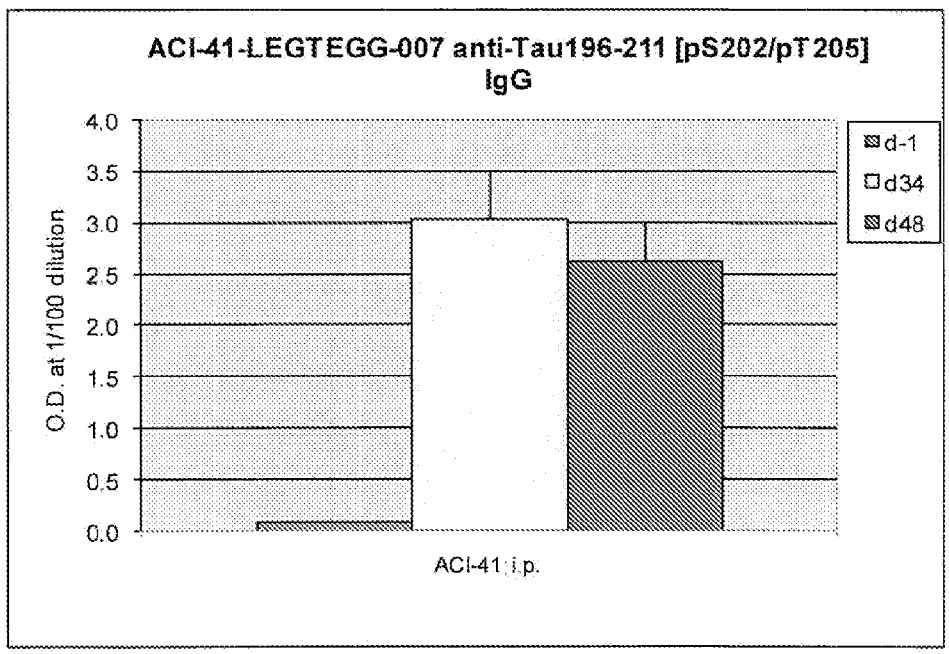
FIGURE: 4d

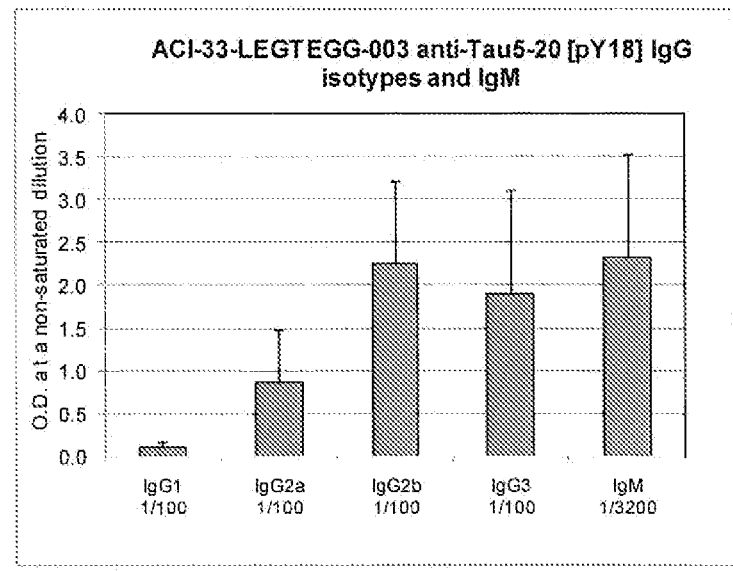
FIGURE: 5a
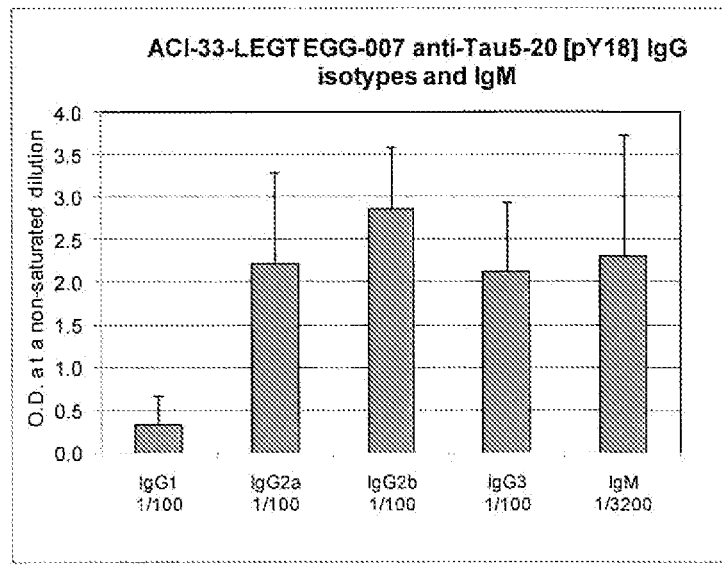
FIGURE: 5b

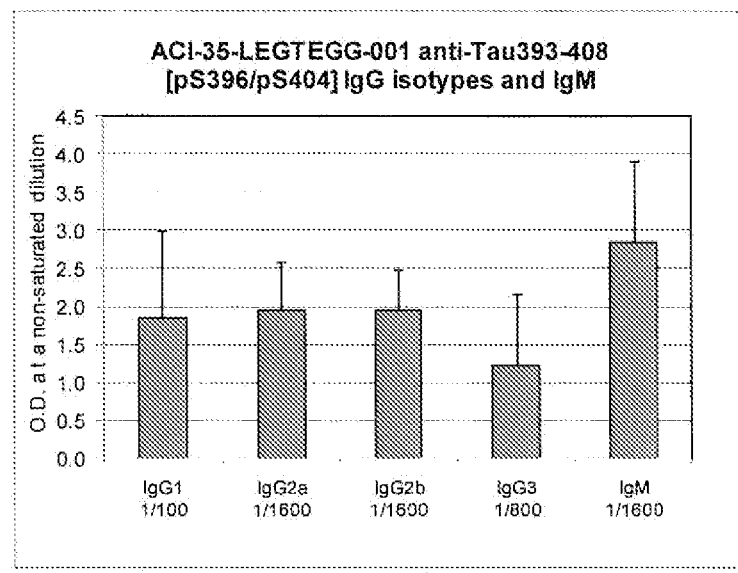
FIGURE: 6a
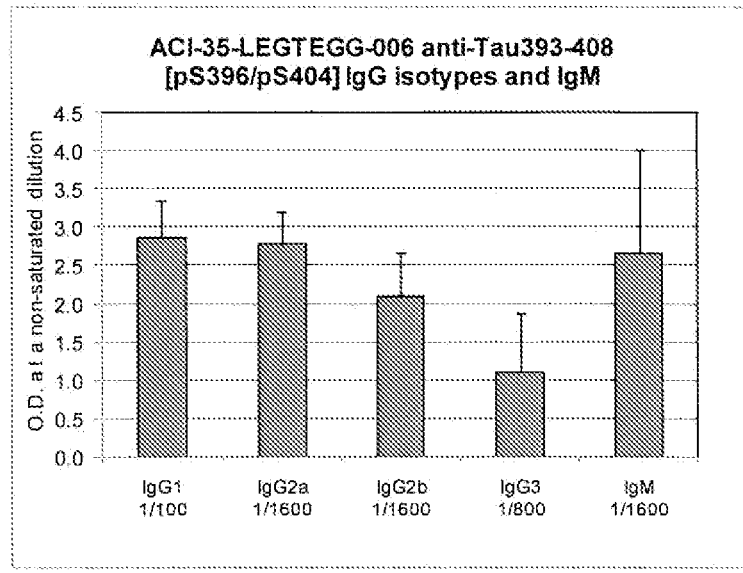
FIGURE: 6b

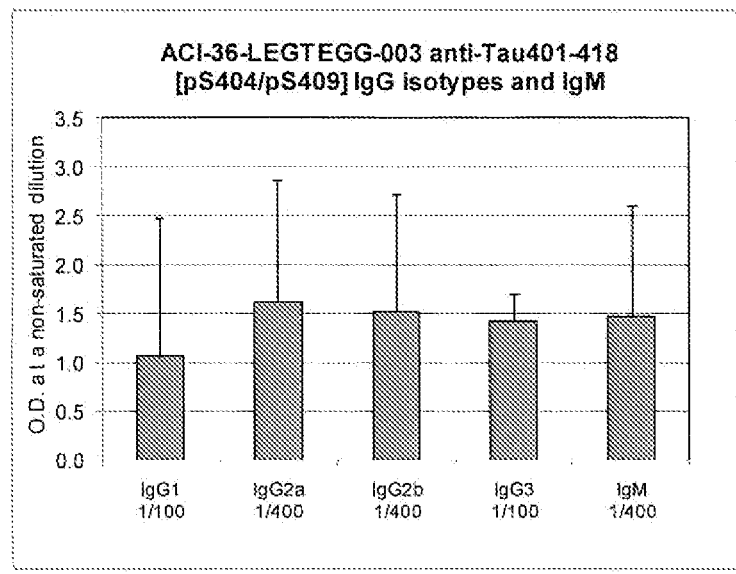
FIGURE: 7a
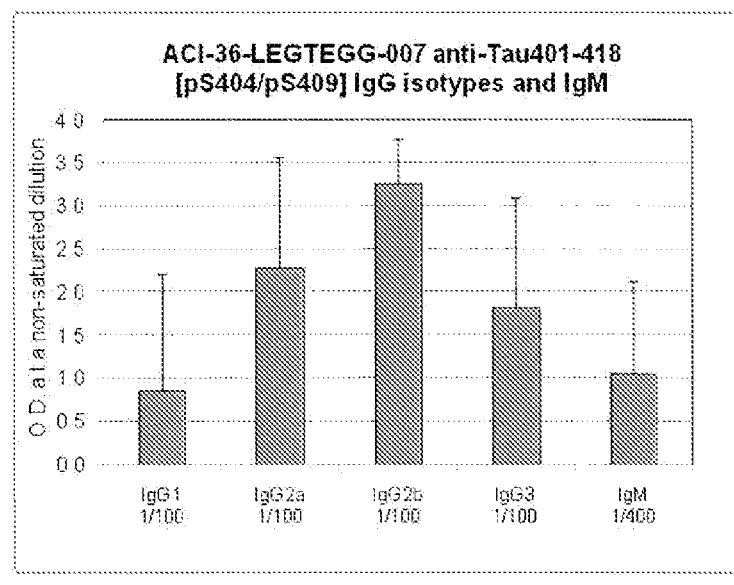
FIGURE: 7b

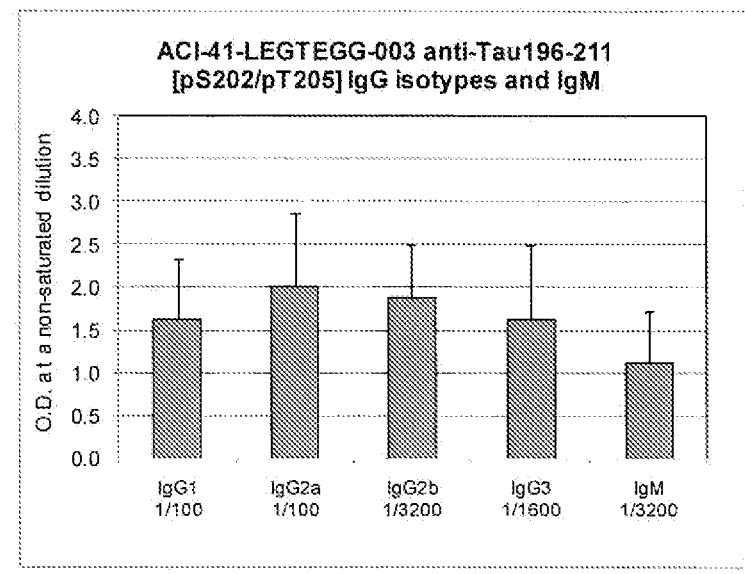
FIGURE: 8a
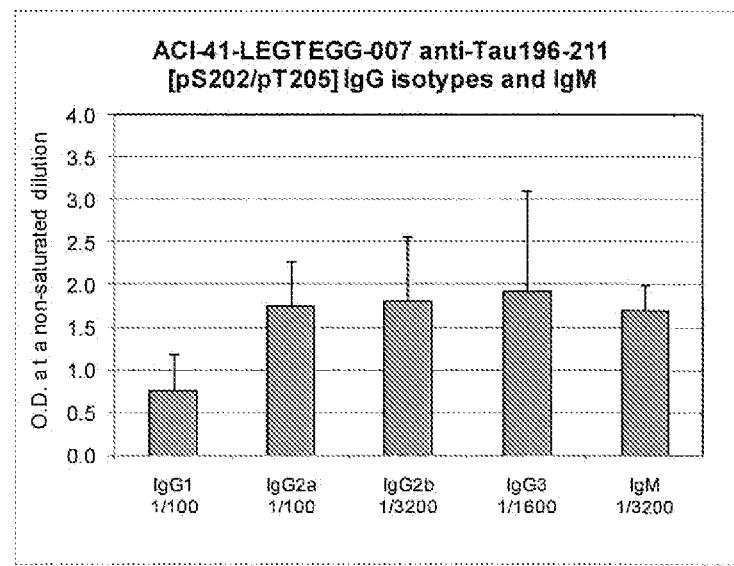
FIGURE: 8b

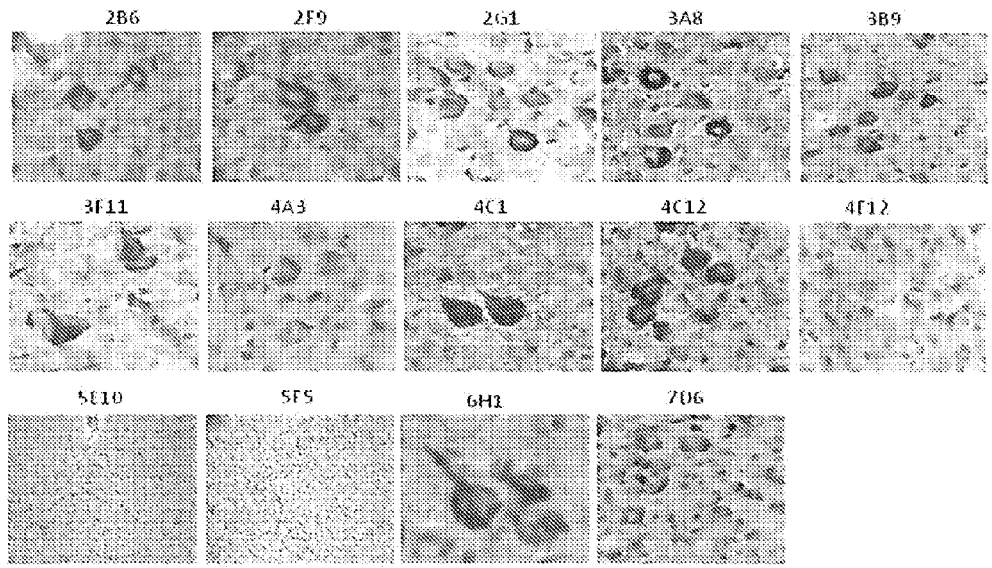
*FIGURE: 9a*
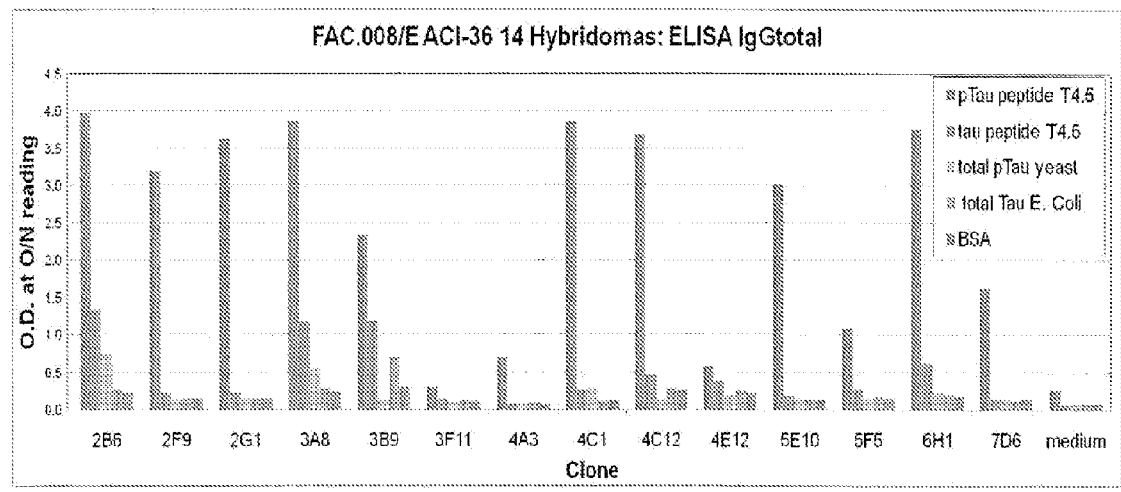
*FIGURE: 9b*

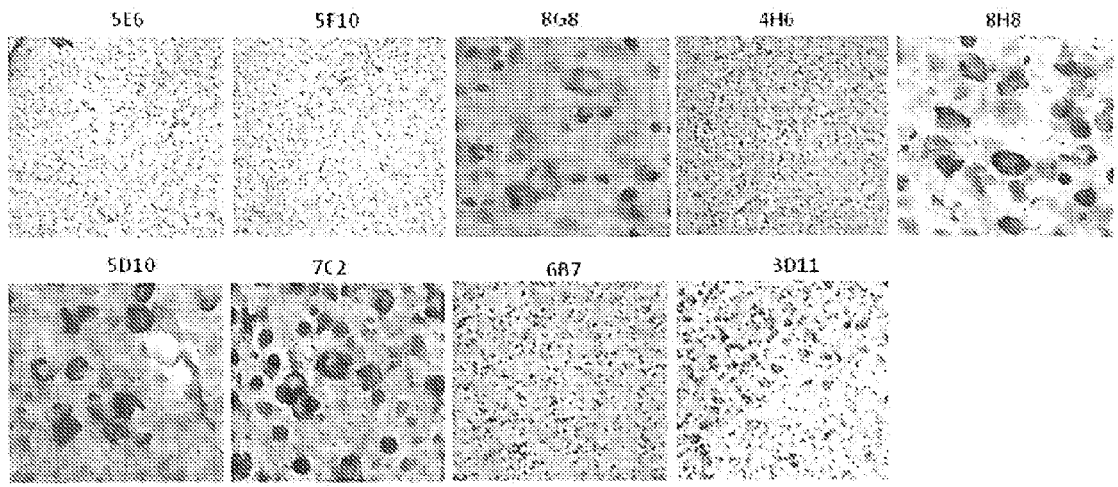
FIGURE: 10a
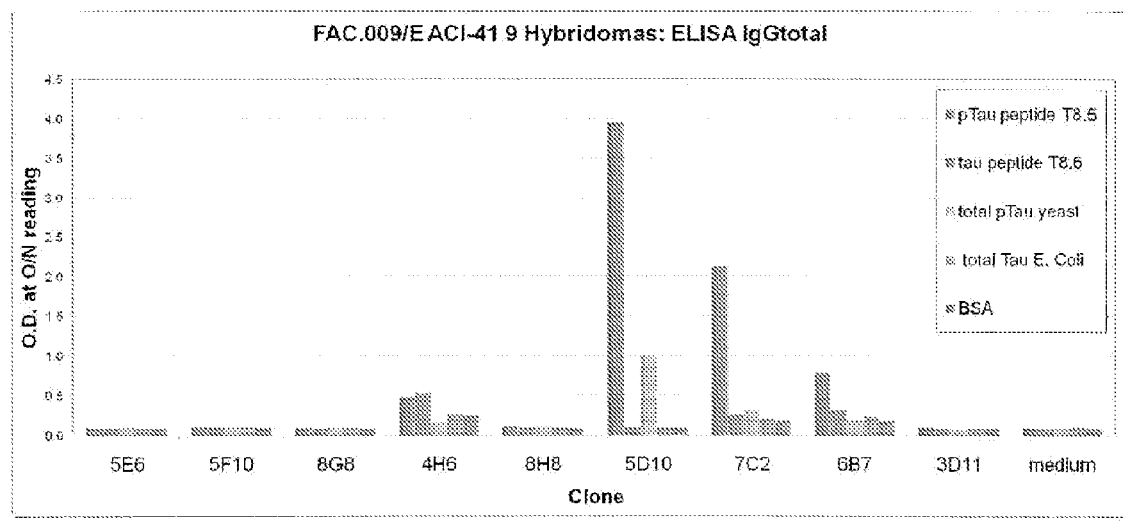
FIGURE: 10b

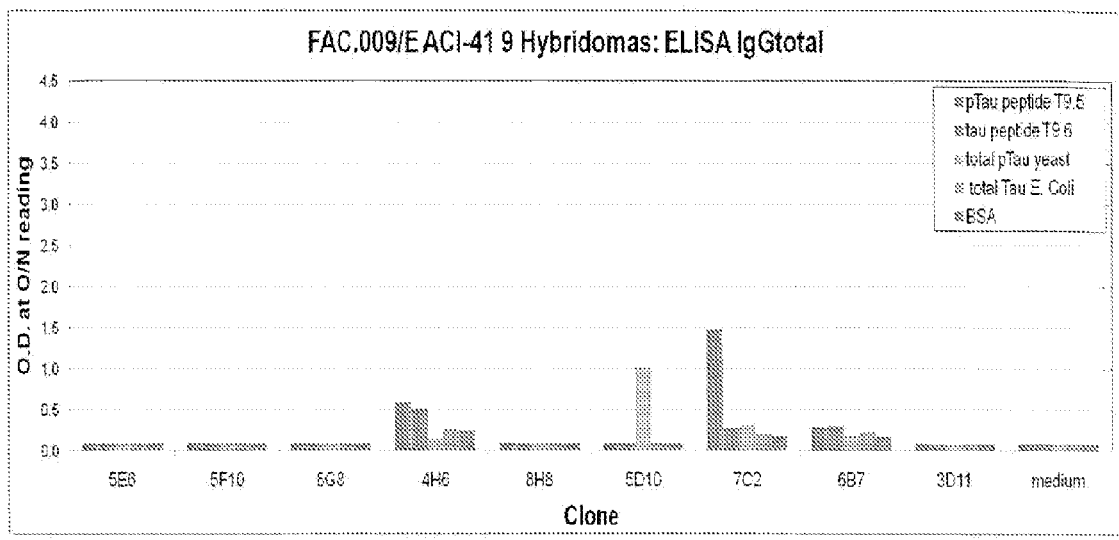
FIGURE: 10c

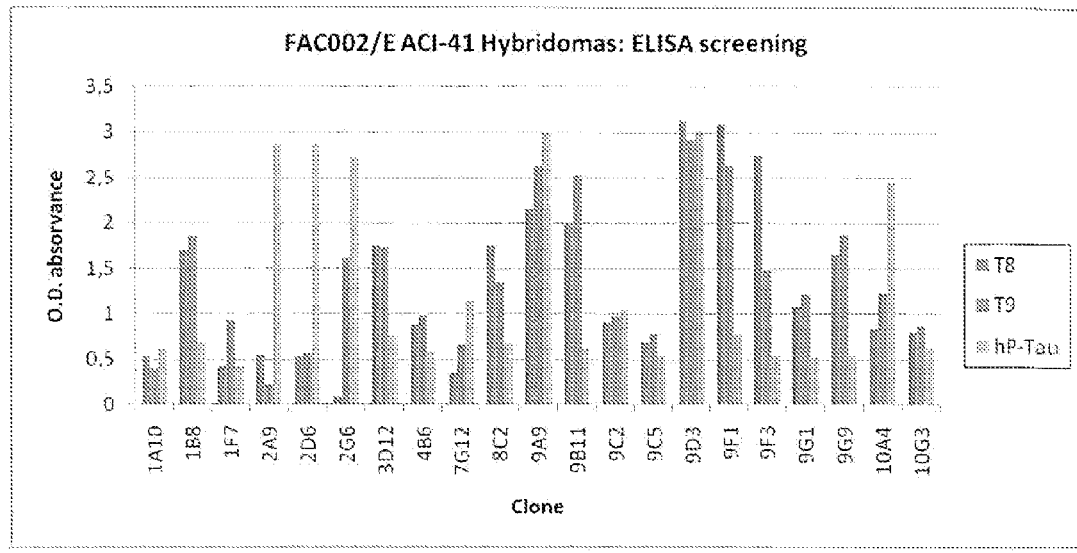
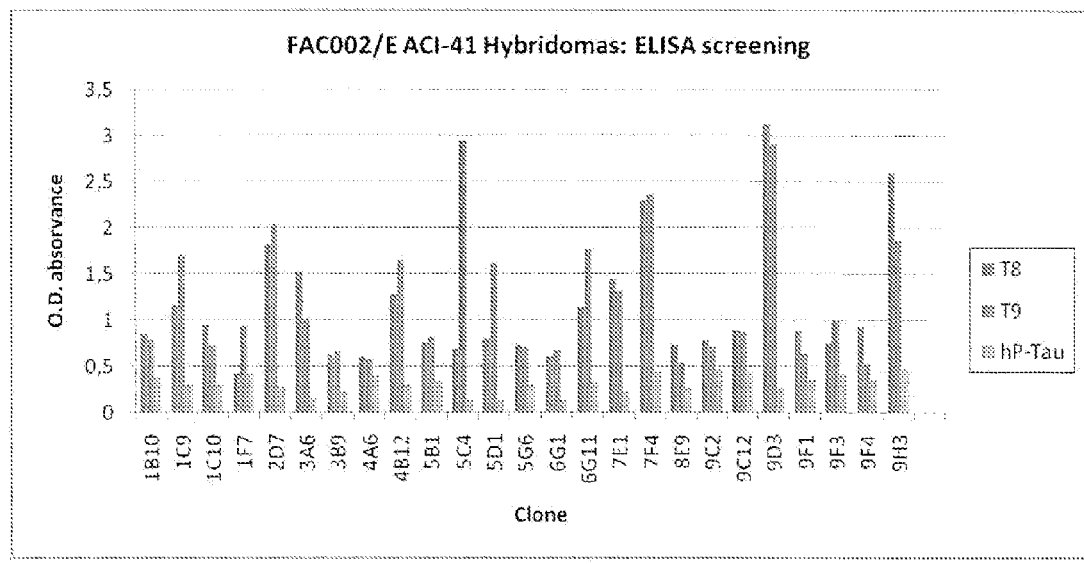
FIGURE:11

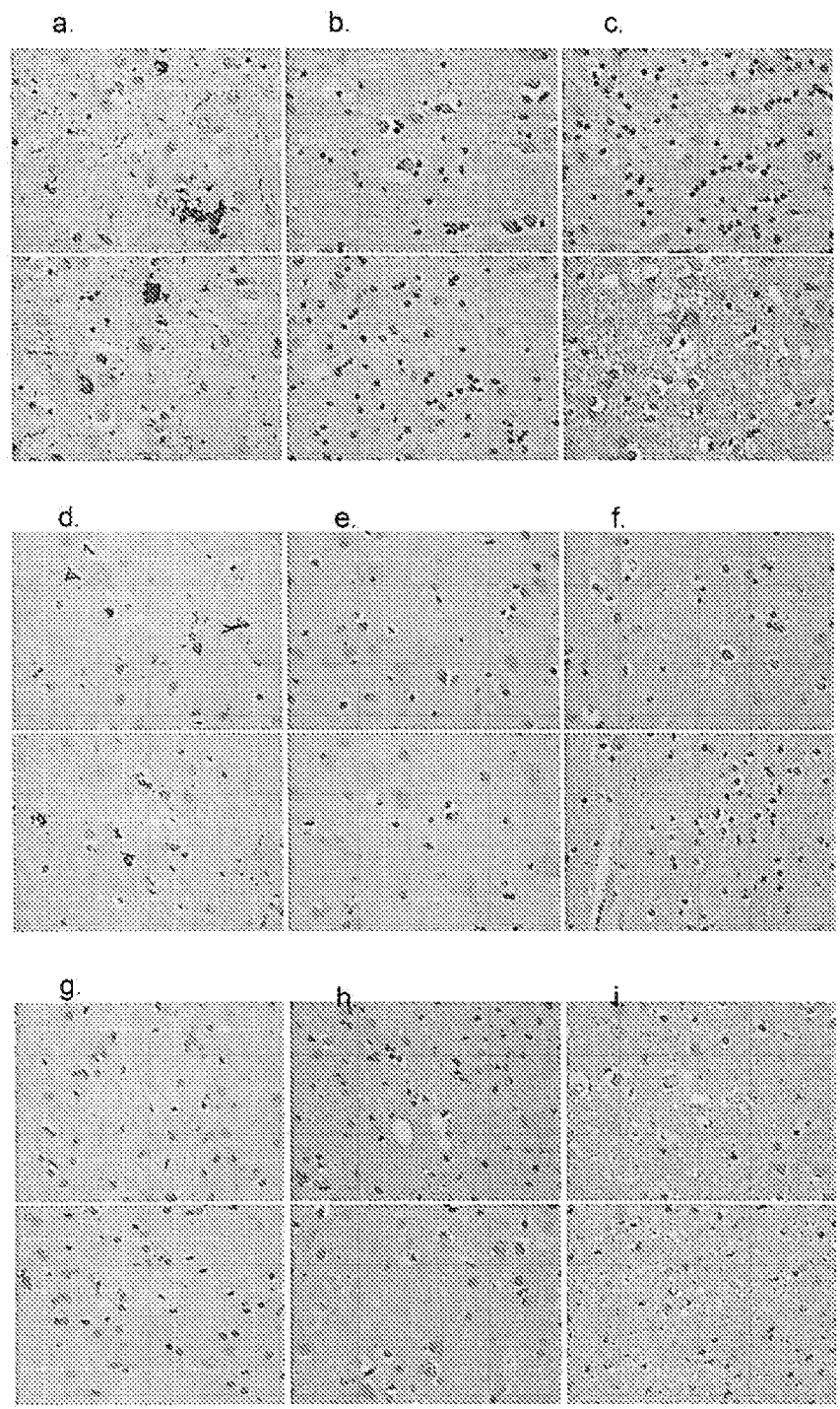
*FIGURE: 12*

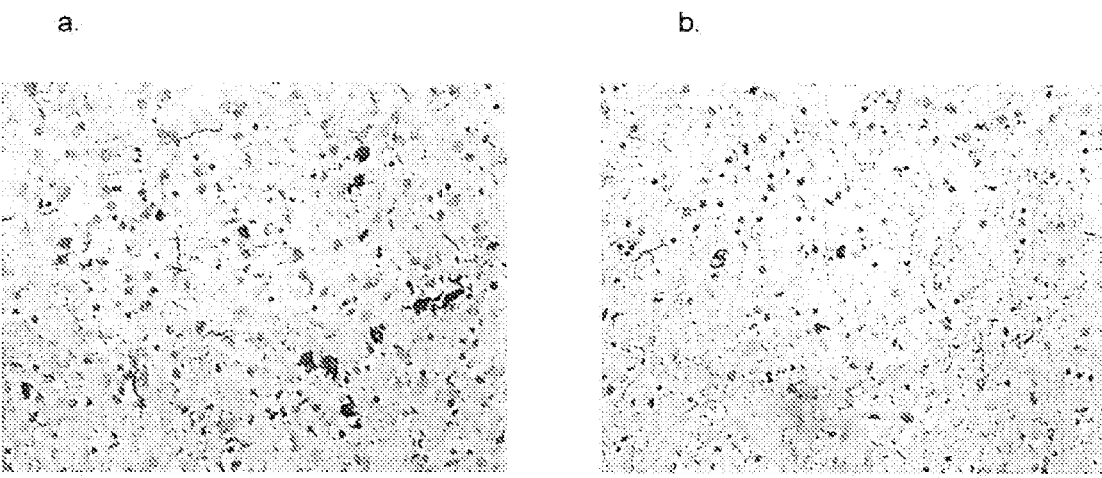
FIGURE: 13

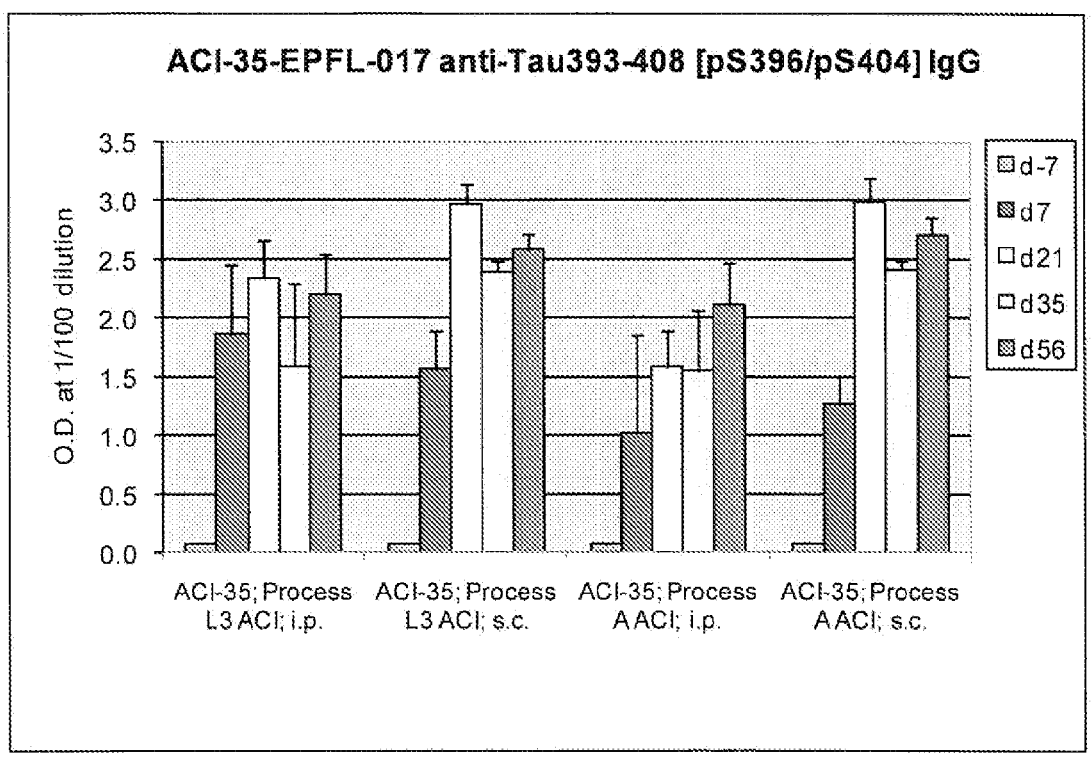
FIGURE: 14

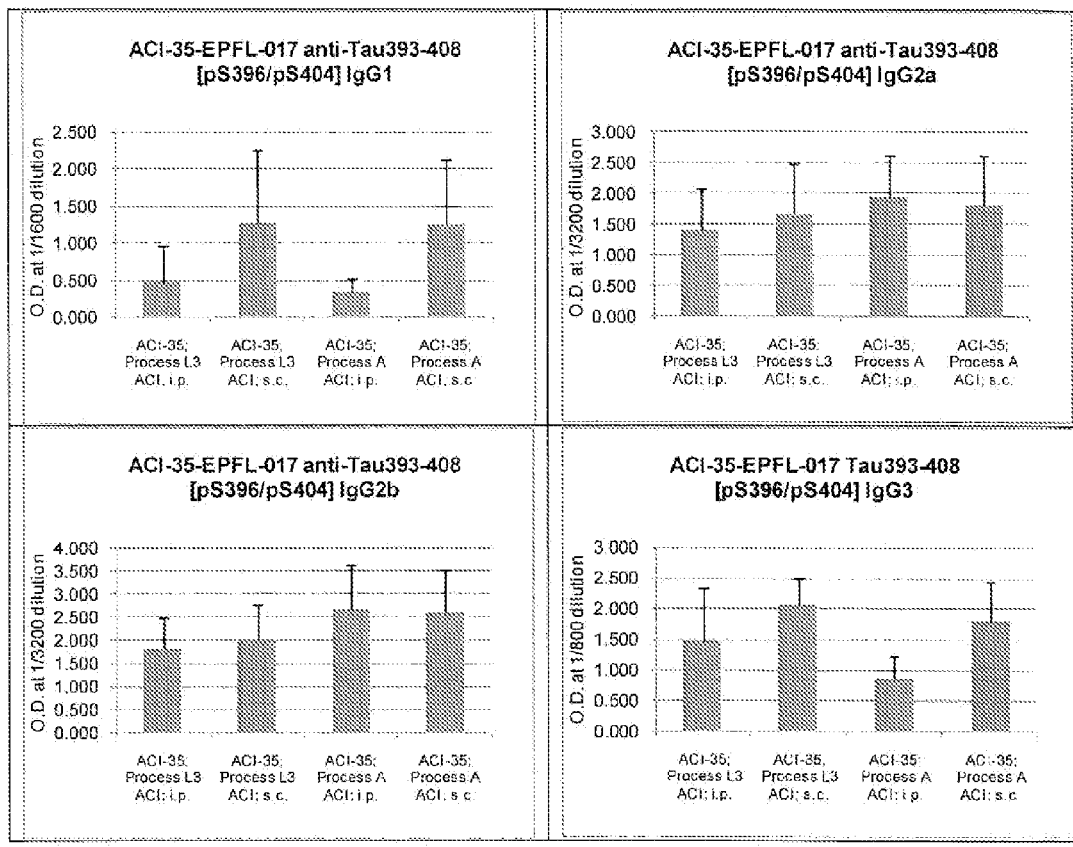
FIGURE: 15

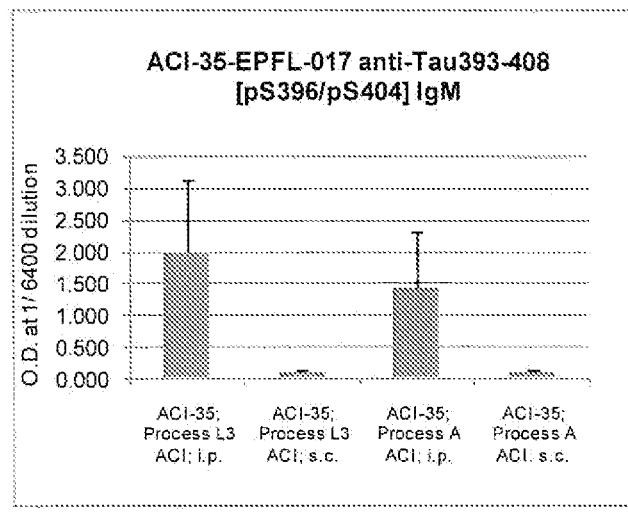
FIGURE: 16a
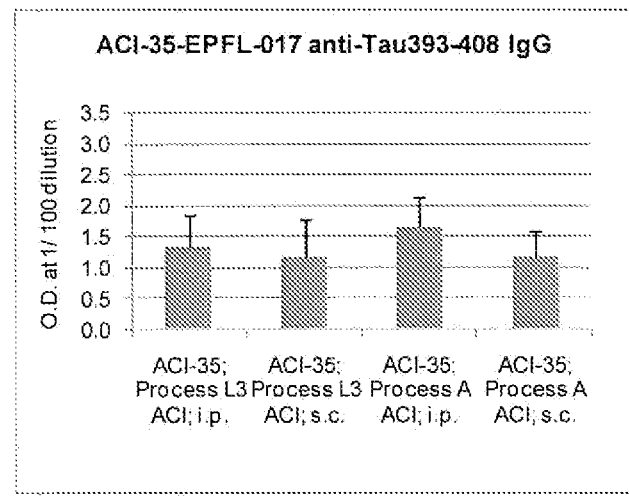
FIGURE: 16b

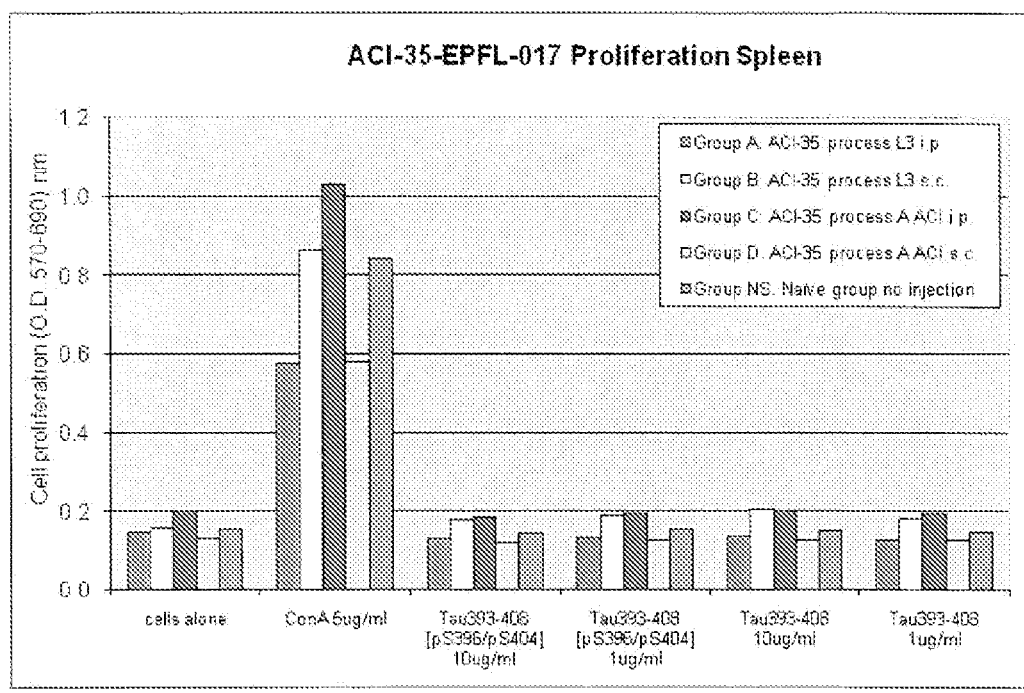
FIGURE: 17

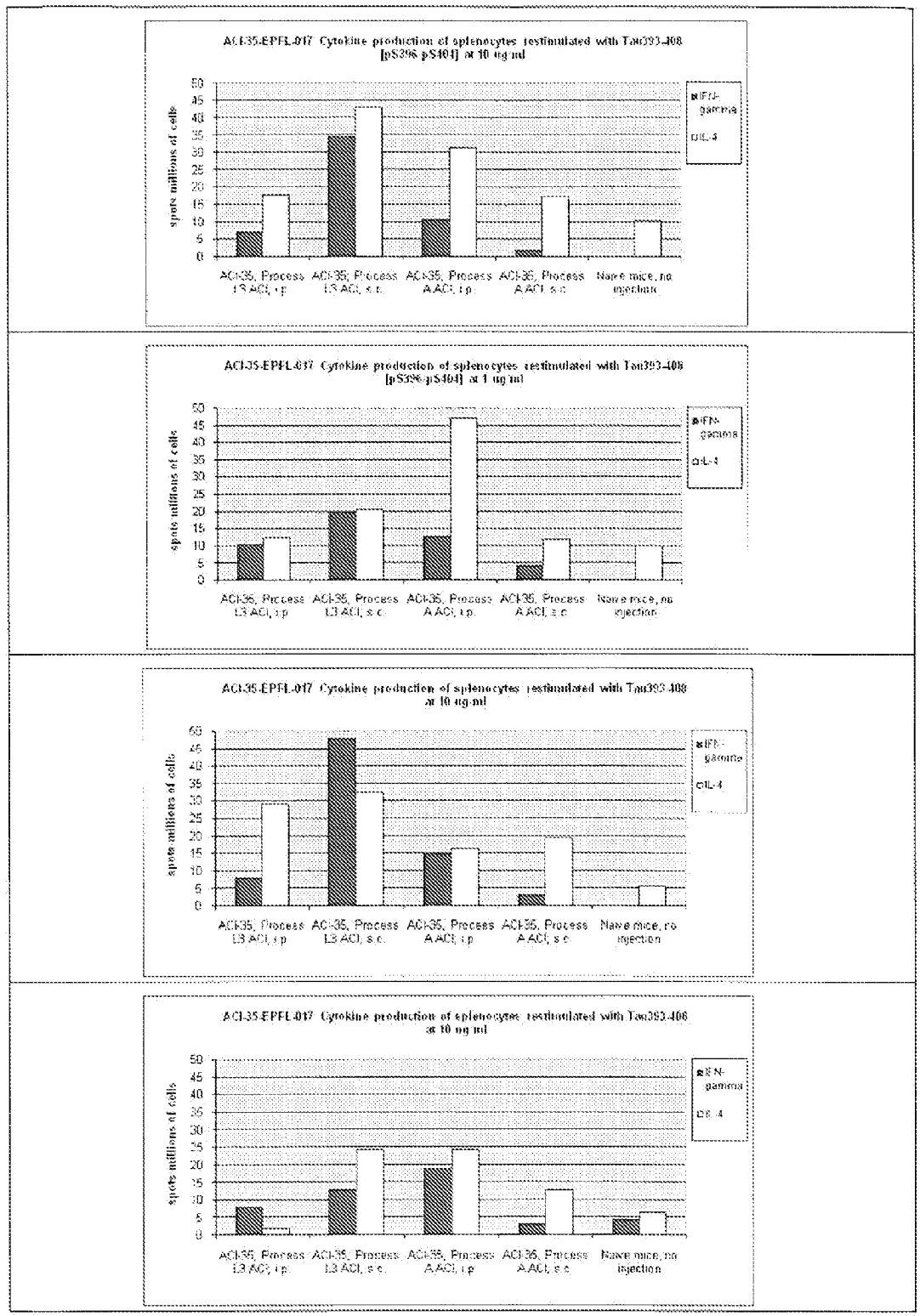
FIGURE: 18

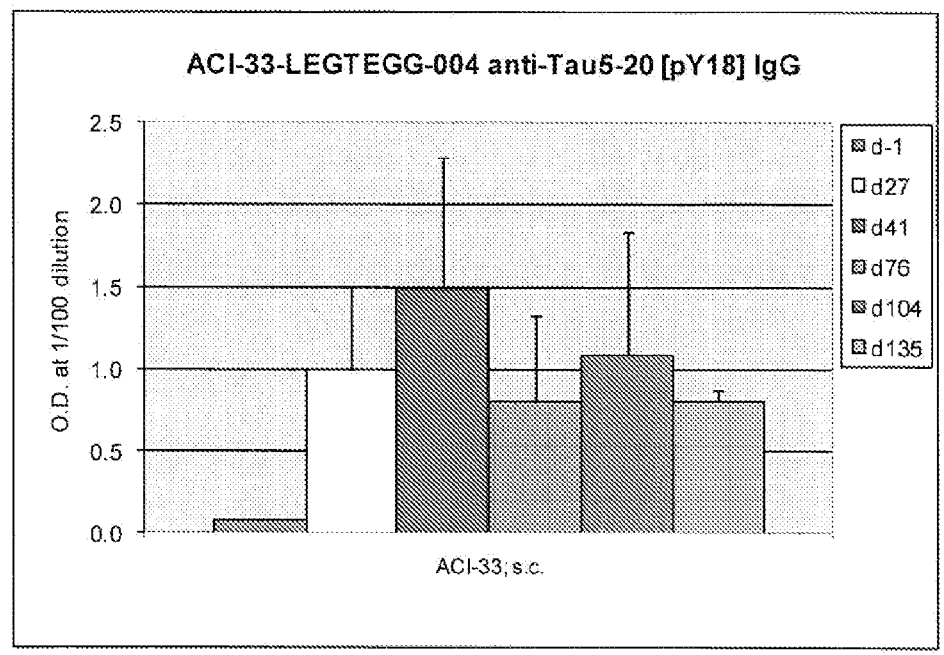
FIGURE: 19
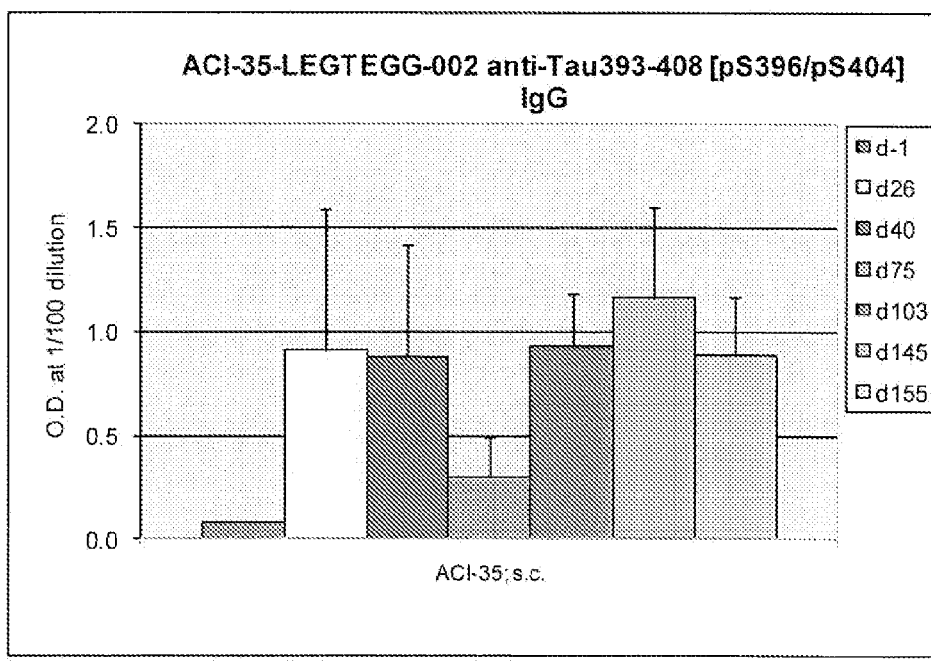
FIGURE: 20

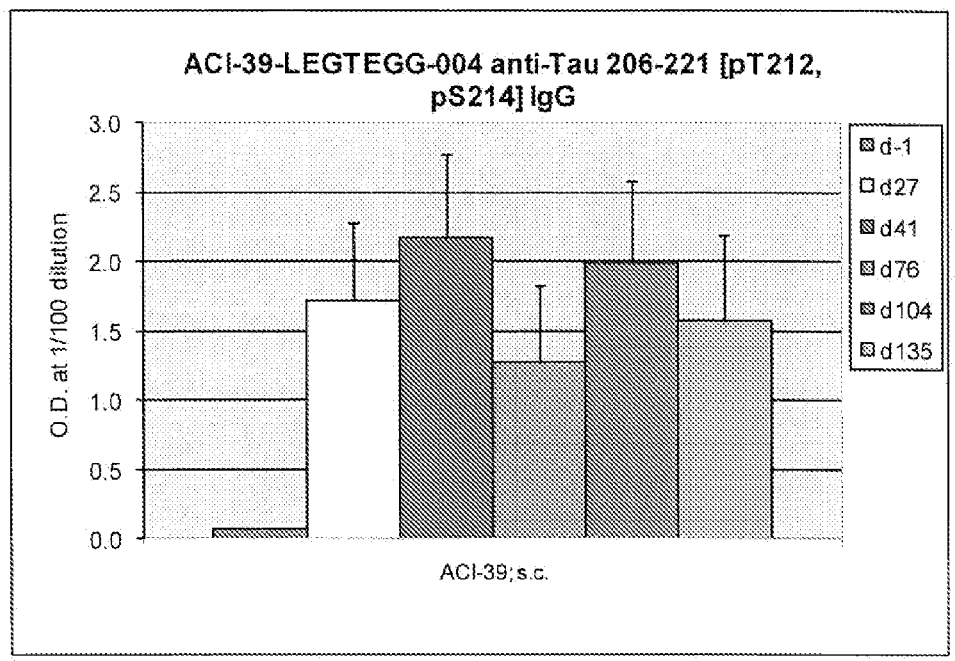
FIGURE: 21
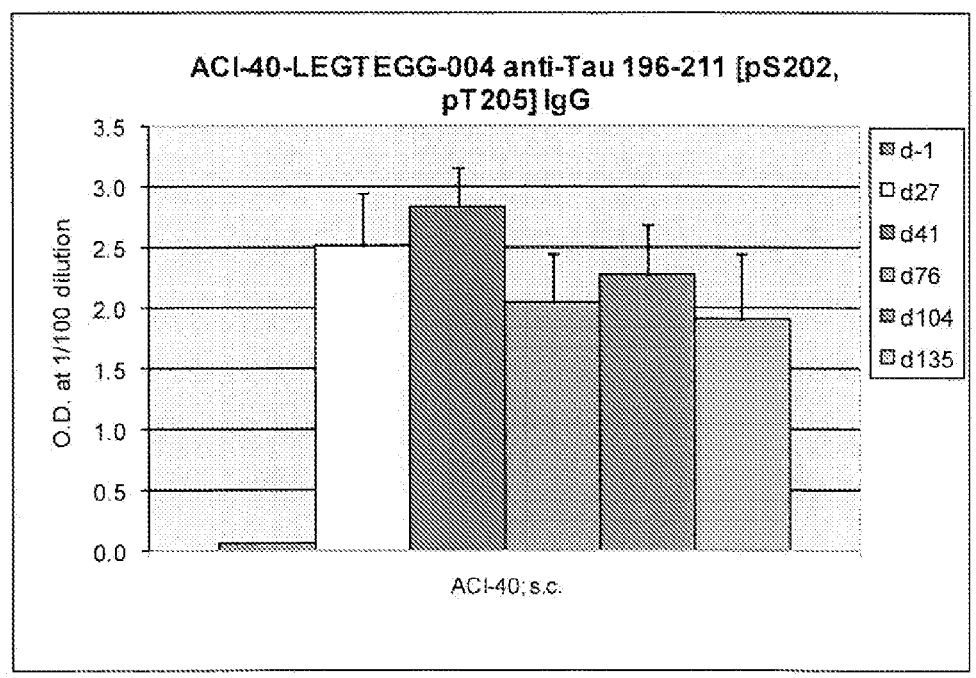
FIGURE: 22

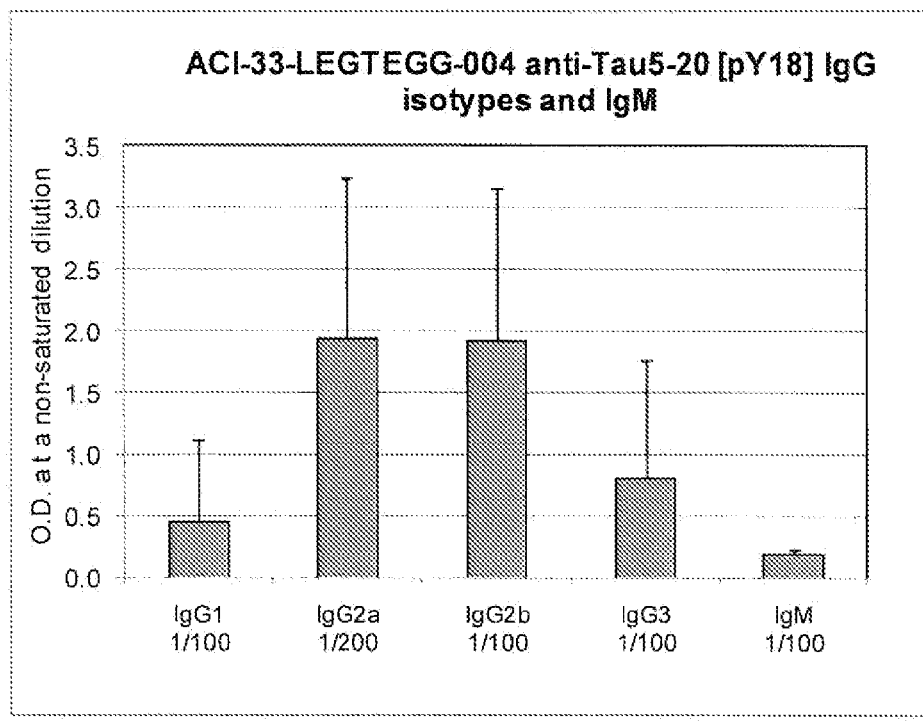
FIGURE: 23
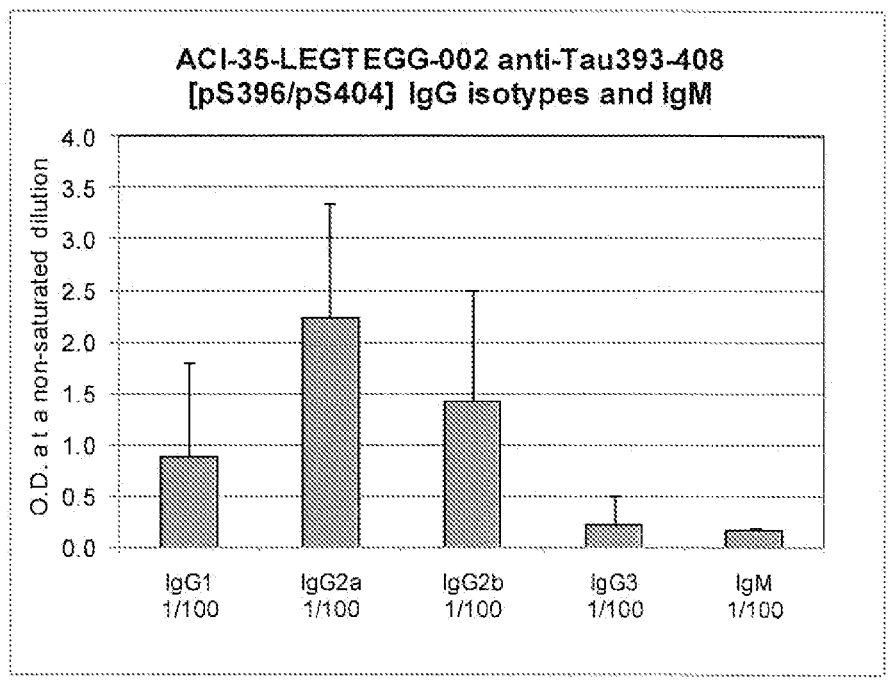
FIGURE: 24

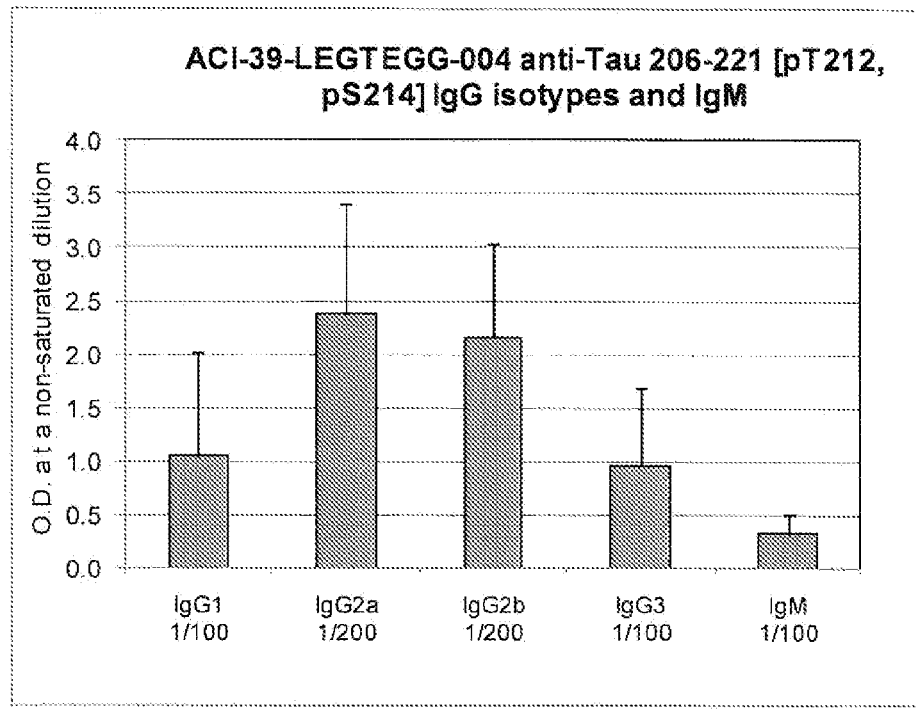
FIGURE: 25
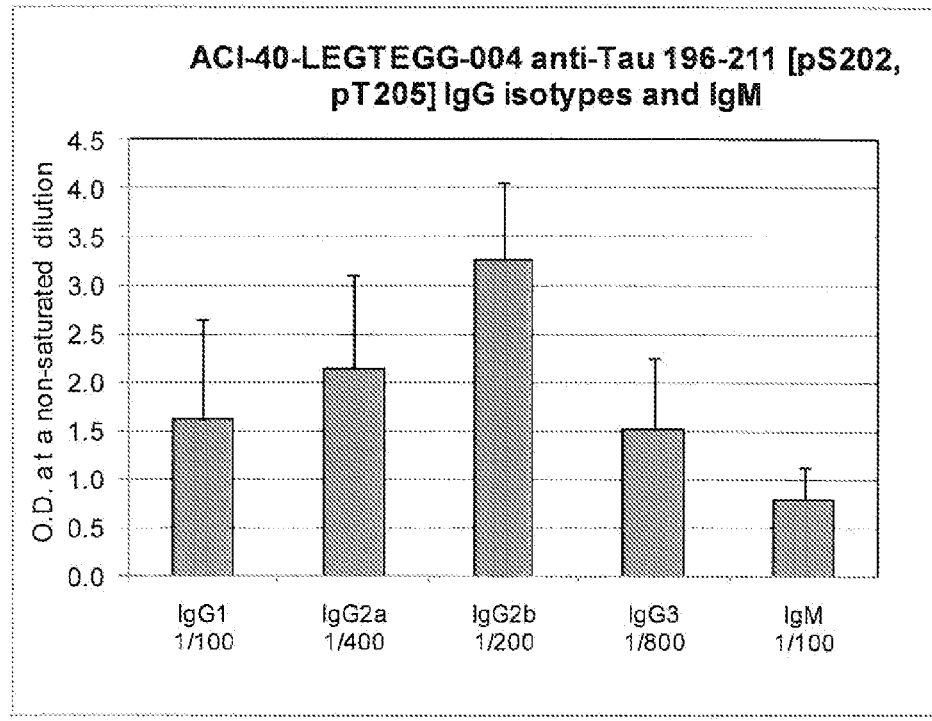
FIGURE: 26

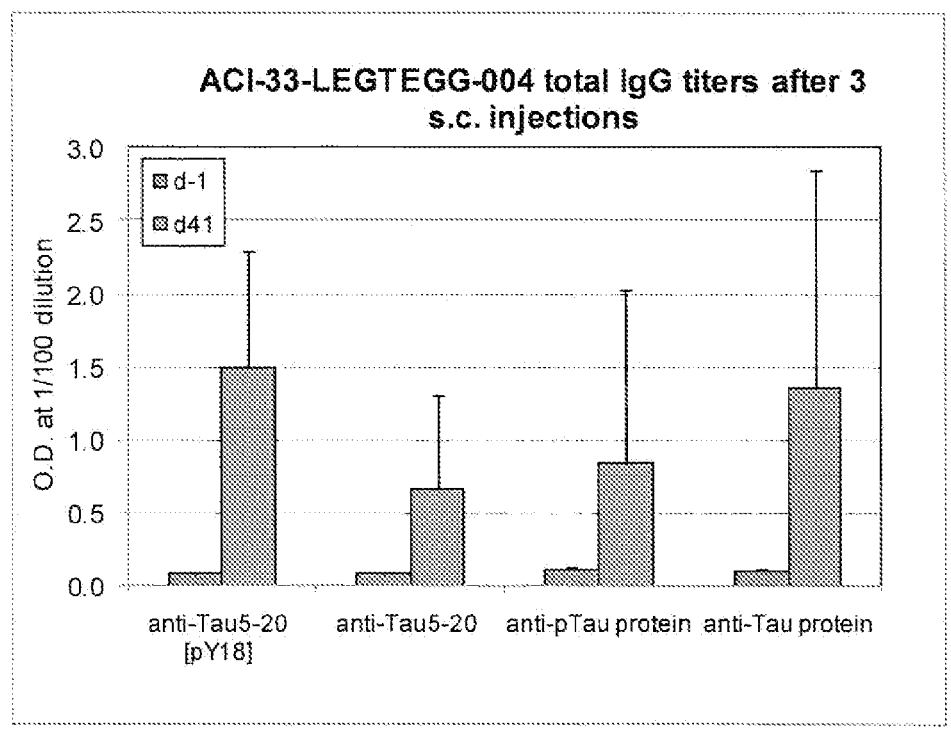
FIGURE: 27
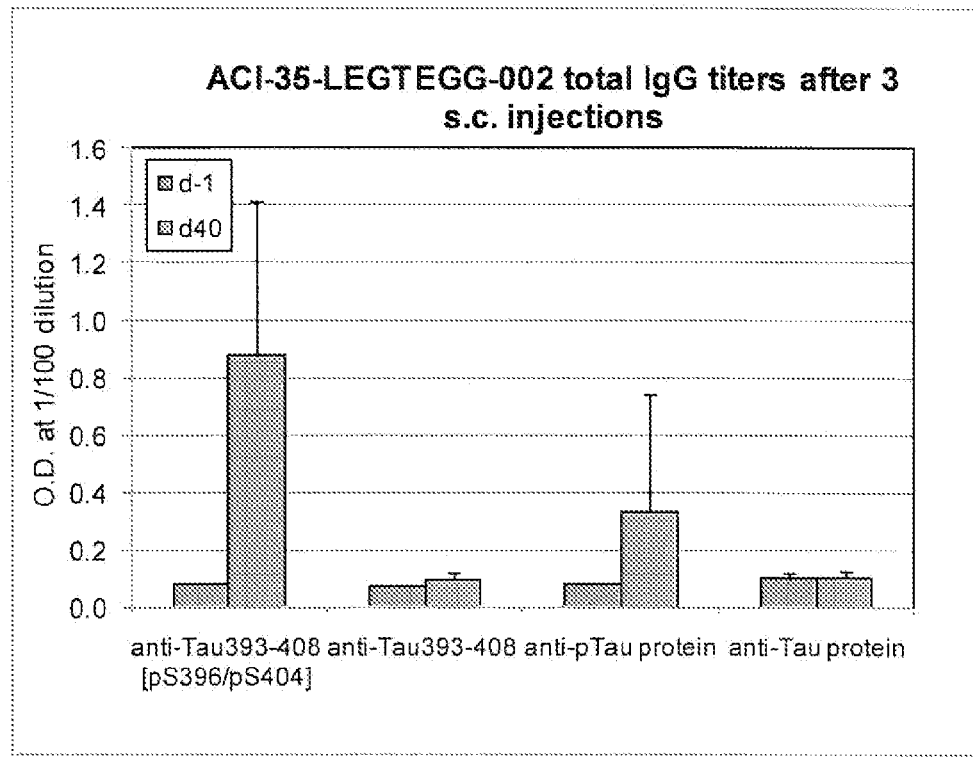
FIGURE: 28

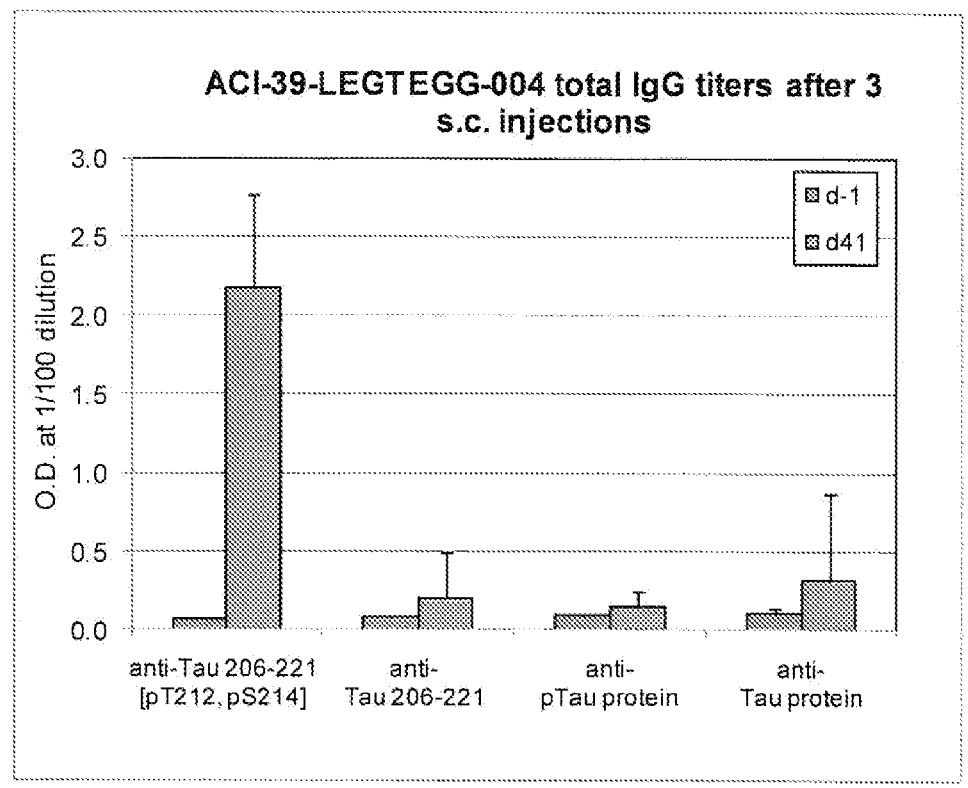
FIGURE: 29
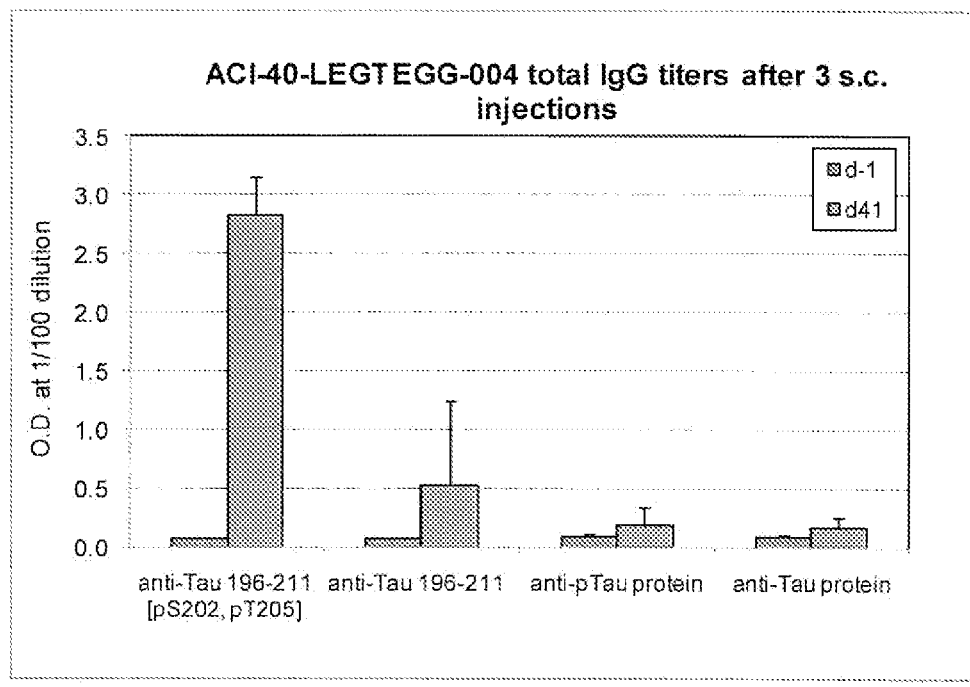
FIGURE: 30

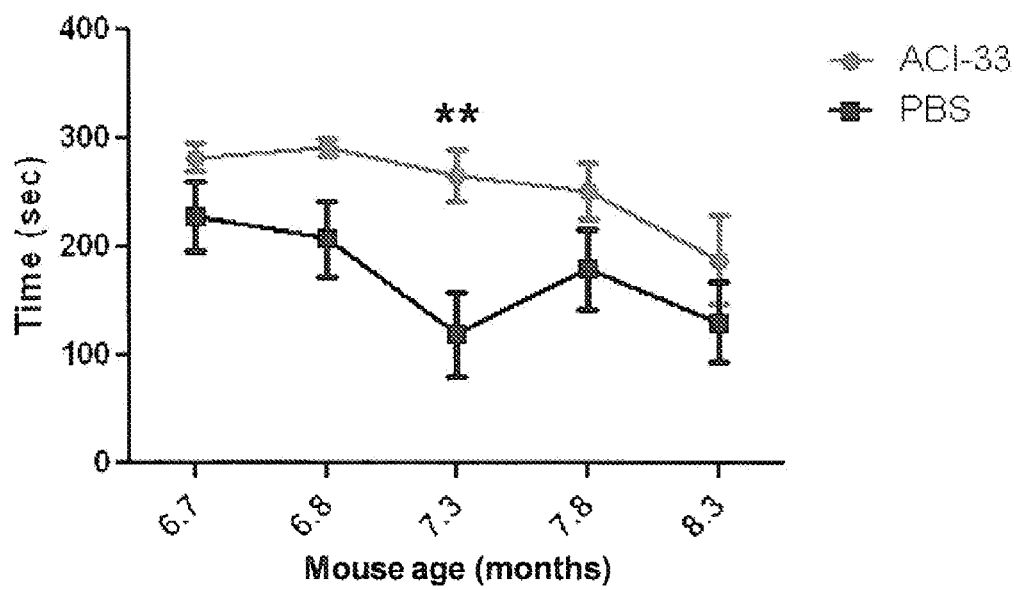
FIGURE: 31
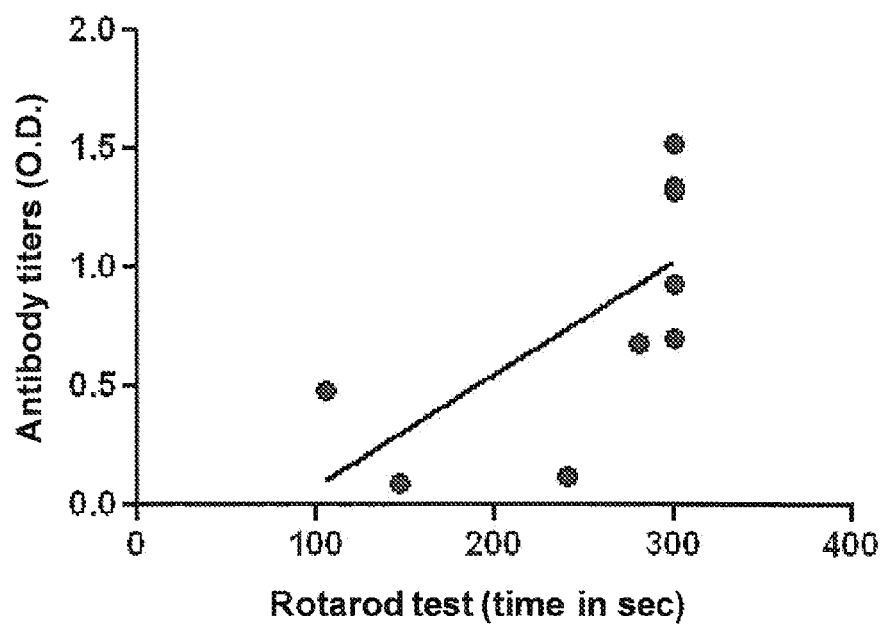
FIGURE: 32

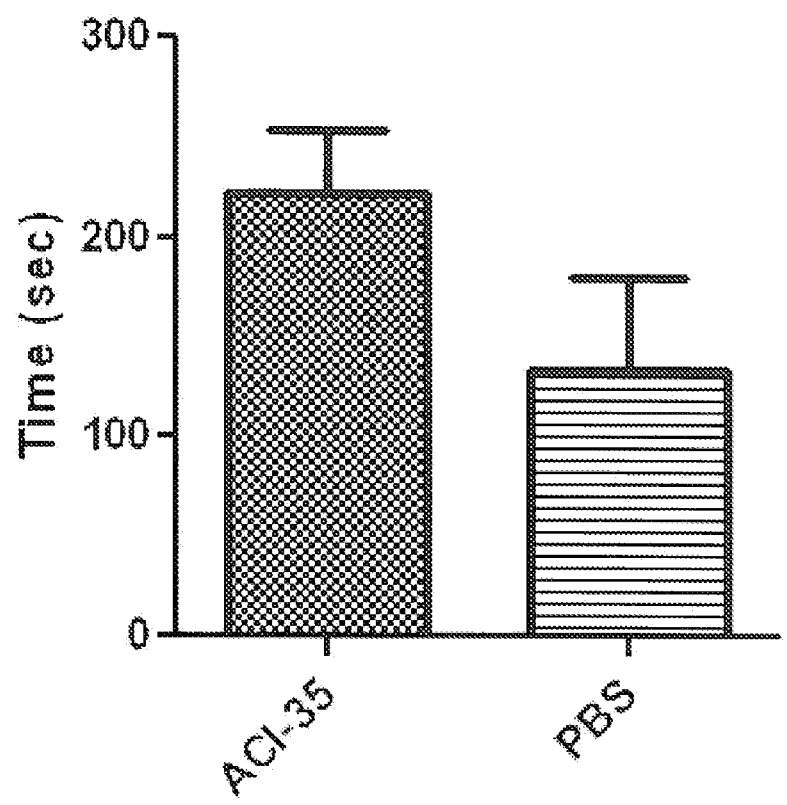
FIGURE: 33

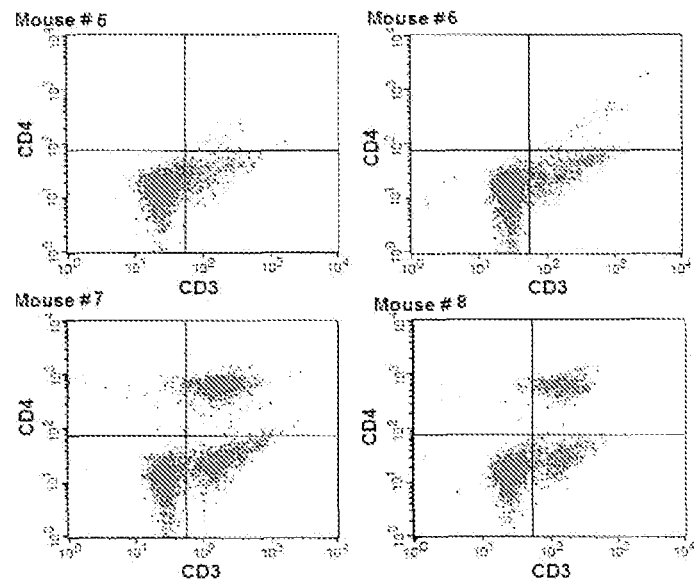
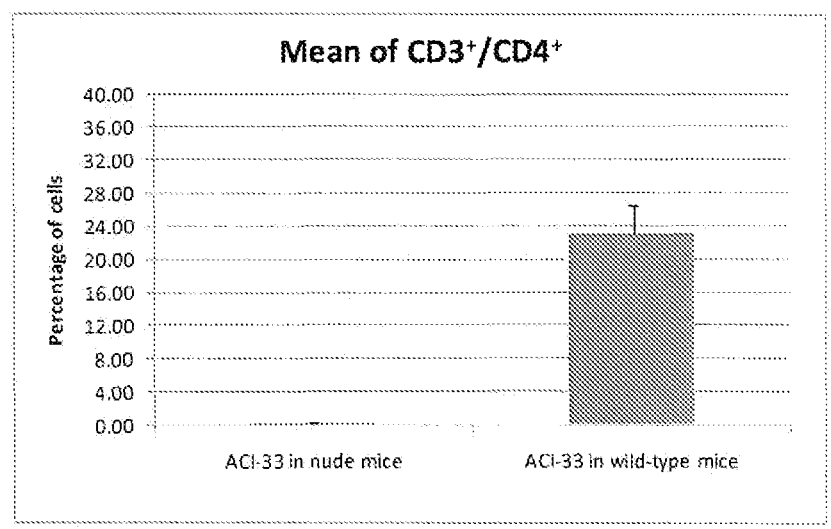
Figure 34

```
                        SEQUENCE LISTING

<160> NUMBER OF SEQ ID NOS: 9

<210> SEQ ID NO 1
<211> LENGTH: 30
<212> TYPE: PRT
<213> ORGANISM: Homo Sapiens
<220> FEATURE:
<221> NAME/KEY: VARIANT
<222> LOCATION: (18)..(18)
<223> OTHER INFORMATION: /replace="phosphorylated serine"
<220> FEATURE:
<221> NAME/KEY: VARIANT
<222> LOCATION: (26)..(26)
<223> OTHER INFORMATION: /replace="phosphorylated serine"

<400> SEQUENCE: 1

Arg Glu Asn Ala Lys Ala Lys Thr Asp His Gly Ala Glu Ile Val Tyr
1               5                   10                  15

Lys Ser Pro Val Val Ser Gly Asp Thr Ser Pro Arg His Leu
            20                  25                  30

<210> SEQ ID NO 2
<211> LENGTH: 16
<212> TYPE: PRT
<213> ORGANISM: Homo Sapiens
<220> FEATURE:
<221> NAME/KEY: VARIANT
<222> LOCATION: (14)..(14)
<223> OTHER INFORMATION: /replace="phosphorylated tyrosine"

<400> SEQUENCE: 2

Arg Gln Glu Phe Glu Val Met Glu Asp His Ala Gly Thr Tyr Gly Leu
1               5                   10                  15

<210> SEQ ID NO 3
<211> LENGTH: 16
<212> TYPE: PRT
<213> ORGANISM: Homo Sapiens
<220> FEATURE:
<221> NAME/KEY: VARIANT
<222> LOCATION: (7)..(7)
<223> OTHER INFORMATION: /replace="phosphorylated threonine"
<220> FEATURE:
<221> NAME/KEY: VARIANT
<222> LOCATION: (9)..(9)
<223> OTHER INFORMATION: /replace="phosphorylated serine"

<400> SEQUENCE: 3

Pro Gly Ser Arg Ser Arg Thr Pro Ser Leu Pro Thr Pro Pro Thr Arg
1               5                   10                  15
```

```
<210> SEQ ID NO 4
<211> LENGTH: 16
<212> TYPE: PRT
<213> ORGANISM: Homo Sapiens
<220> FEATURE:
<221> NAME/KEY: VARIANT
<222> LOCATION: (7)..(7)
<223> OTHER INFORMATION: /replace="phosphorylated serine"
<220> FEATURE:
<221> NAME/KEY: VARIANT
<222> LOCATION: (10)..(10)
<223> OTHER INFORMATION: /replace="phosphorylated threonine"

<400> SEQUENCE: 4

Gly Tyr Ser Ser Pro Gly Ser Pro Gly Thr Pro Gly Ser Arg Ser Arg
 1               5                  10                  15

<210> SEQ ID NO 5
<211> LENGTH: 16
<212> TYPE: PRT
<213> ORGANISM: Homo Sapiens
<220> FEATURE:
<221> NAME/KEY: VARIANT
<222> LOCATION: (4)..(4)
<223> OTHER INFORMATION: /replace="phosphorylated serine"
<220> FEATURE:
<221> NAME/KEY: VARIANT
<222> LOCATION: (12)..(12)
<223> OTHER INFORMATION: /replace="phosphorylated serine"

<400> SEQUENCE: 5

Val Tyr Lys Ser Pro Val Val Ser Gly Asp Thr Ser Pro Arg His Leu
 1               5                  10                  15

<210> SEQ ID NO 6
<211> LENGTH: 18
<212> TYPE: PRT
<213> ORGANISM: Homo Sapiens
<220> FEATURE:
<221> NAME/KEY: VARIANT
<222> LOCATION: (4)..(4)
<223> OTHER INFORMATION: /replace="phosphorylated serine"
<220> FEATURE:
<221> NAME/KEY: VARIANT
<222> LOCATION: (9)..(9)
<223> OTHER INFORMATION: /replace="phosphorylated serine"

<400> SEQUENCE: 6

Gly Asp Thr Ser Pro Arg His Leu Ser Asn Val Ser Ser Thr Gly Ser
 1               5                  10                  15

Ile Asp

<210> SEQ ID NO 7
<211> LENGTH: 17
<212> TYPE: PRT
<213> ORGANISM: Homo Sapiens
<220> FEATURE:
<221> NAME/KEY: VARIANT
<222> LOCATION: (3)..(3)
<223> OTHER INFORMATION: /replace="phosphorylated serine"
<220> FEATURE:
<221> NAME/KEY: VARIANT
<222> LOCATION: (6)..(6)
<223> OTHER INFORMATION: /replace="phosphorylated threonine"
<220> FEATURE:
<221> NAME/KEY: VARIANT
<222> LOCATION: (13)..(13)
<223> OTHER INFORMATION: /replace="phosphorylated threonine"
<220> FEATURE:
<221> NAME/KEY: VARIANT
<222> LOCATION: (15)..(15)
<223> OTHER INFORMATION: /replace="phosphorylated serine"
```

```
-continued

<400> SEQUENCE: 7

Pro Gly Ser Pro Gly Thr Pro Gly Ser Arg Ser Arg Thr Pro Ser Leu
1               5                   10                  15

Pro

<210> SEQ ID NO 8
<211> LENGTH: 12
<212> TYPE: PRT
<213> ORGANISM: Homo Sapiens
<220> FEATURE:
<221> NAME/KEY: VARIANT
<222> LOCATION: (3)..(3)
<223> OTHER INFORMATION: /replace="phosphorylated serine"

<400> SEQUENCE: 8

His Leu Ser Asn Val Ser Ser Thr Gly Ser Ile Asp
1               5                   10

<210> SEQ ID NO 9
<211> LENGTH: 10
<212> TYPE: PRT
<213> ORGANISM: Homo Sapiens
<220> FEATURE:
<221> NAME/KEY: VARIANT
<222> LOCATION: (6)..(6)
<223> OTHER INFORMATION: /replace="phosphorylated serine"

<400> SEQUENCE: 9

Val Ser Gly Asp Thr Ser Pro Arg His Leu
1               5                   10
```

PHARMACEUTICAL COMPOSITION OF AN ANTIGENIC TAU PEPTIDE RECONSTITUTED IN A LIPOSOME AND RELATED ANTIBODIES AND CELL LINES

CROSS-REFERENCE TO RELATED APPLICATIONS

This application is a 35 U.S.C. §371 national stage application of International Patent Application Number PCT/EP2010/054418 filed on Apr. 1, 2010, which claims the benefit of priority to European Patent Application Number 09157303.0 filed on Apr. 3, 2009, the disclosures of which are hereby incorporated by reference.

The present invention is related to methods and compositions for the therapeutic and diagnostic use in the treatment of diseases and disorders which are caused by or associated with neurofibrillary tangles. In particular, the invention relates to methods and compositions for the therapeutic and diagnostic use in the treatment of tauopathies including Alzheimer's Disease (AD).

Neurofibrillary tangles are a major neuropathological hallmark in AD. They originate by the aggregation of hyper-phosphorylated protein tau and its conformers. AD shares this pathology with many neurodegenerative tauopathies, in particularly with specified types of frontotemporal dementia (FTD).

Protein Tau is a freely soluble, "naturally unfolded" protein that binds avidly to microtubuli (MT) to promote their assembly and stability. MTs are of major importance for the cytoskeletal integrity of neurons—and thereby for the proper formation and functioning of neuronal circuits, hence for learning and memory. The binding of tau to MT is controlled by dynamic phosphorylation and de-phosphorylation, as demonstrated mainly in vitro and in non-neuronal cells. Due to the large number of possible phosphorylation sites (>80), the exact contribution of each, and the identity of the responsible kinases remains largely undefined in vivo.

In AD brain, tau pathology develops later than, and therefore probably in response to amyloid pathology, which constitutes the essence of the amyloid cascade hypothesis. This is based on and indicated by studies in AD and Down syndrome patients, and is corroborated by studies in transgenic mice with combined amyloid and tau pathology (Lewis et al., 2001; Oddo et al., 2004; Ribe et al., 2005; Muyllaert et al, 2006; 2008; Terwel et al, 2008).

The exact timing of both pathologies in human AD patients as well as mechanisms that link amyloid to tau pathology remain largely unknown, but are proposed to involve activation of neuronal signaling pathways that act on or by GSK3 and cdk5 as the major "tau-kinases" (reviewed by Muyllaert et al, 2006, 2008).

The hypothesis that tauopathy is not an innocent side-effect but a major pathological executer in AD is based on sound genetic, pathological and experimental observations that corroborate each other fully:
  in early-onset familial AD cases that are due to mutations in amyloid protein precursor (APP) or presenilin, the obligate pathogenic cause is amyloid accumulation, but invariably the pathology comprises collateral tauopathy, identical to that in the late-onset sporadic AD cases
  severity of cognitive dysfunction and dementia correlates with tauopathy, not with amyloid pathology, exemplified most recently by several clinical phase-1&2 studies that include PIB-PET imaging for amyloid and identify many "false positives": cognitively normal individuals with high brain amyloid load.
  in familial FTD, the tauopathy is provoked by mutant tau and causes neurodegeneration directly, without amyloid pathology
  in experimental mouse models the cognitive defects caused by amyloid pathology are nearly completely alleviated by the absence of protein tau (Roberson et al, 2007).

The combined arguments support the hypothesis that protein tau is a major player in the cognitive demise in AD and related neurodegenerative tauopathies.

A prominent emerging treatment of AD is by passive immunotherapy with specific mAbs, to clear amyloid peptides and their aggregates that are presumed to be neuro-toxic or synapto-toxic.

Immunotherapy targeting tau pathology, as proposed here, is anticipated to counteract the pathological protein tau-conformers that are known or postulated to cause neurodegeneration. Amyloid pathology in AD caused and intra-neuronal aggregates of hyper-phosphorylated protein tau are proposed to act synergistically in the cognitive and degenerative cascade of pathological events that leads from mild cognitive impairment (MCI) to the severe dementia of AD. The combination of tau-directed with amyloid directed (or any other) medication will therefore constitute the preferred and, and substantially more efficacious treatment of AD.

Other therapeutic approaches that target protein tau are scarce and comprise mainly:
  inhibitors of the kinases that are thought to increase the phosphorylation of tau to pathological levels
  compounds that block the cytoplasmic aggregation of hyper-phosphorylated protein tau.

These approaches suffer various draw-backs of specificity and efficacy, a problem they share with attempts to modify the metabolism of APP and amyloid, all emphasizing the importance of a continuous search for additional treatment options, including immunotherapy against tau.

Practically no efforts have been devoted to define—let alone target—the pathological tau conformers in vivo. In the Aβ42 phase H clinical trial, the tangle pathology did not appear to be well considered nor analyzed in much depth (Nicoll et al., 2003; Masliah et al., 2005). On the other hand, experimental immunotherapy targeting amyloid in a preclinical mouse model with combined AD-like pathology demonstrated also an effect on tau pathology although tau aggregates persisted (Oddo et at, 2004).

Some doubts have been cast on the feasibility of approaching intra-cellular protein tau by immunotherapy. These have been countered by the most recent experimental study in a tauopathy mouse model by Asuni and colleagues (Asuni et at, 2007). They showed reduction in tangle pathology and functional improvements by vaccination with a protein tau derived phospho-peptide. These data corroborate previous reports of immunotherapy targeting α-synuclein in a Parkinson's disease (PD) model (Masliah et at, 2005) and of superoxide dismutase in an amyotrophic lateral sclerosis (ALS) model (Urushitiani et al., 2007). These two diseases are examples of intra-cellular proteins that lead to neurodegeneration by as yet not fully understood mechanisms. On the other hand, full-length recombinant protein tau produced in and isolated from bacteria appears not suitable as vaccine, although the adjuvants used, i.e. complete Freunds and pertussis toxin, could have contributed to the negative outcome of that study (Rosenmann et al., 2006).

There is an unmet need for passive and/or active immunotherapies that work to counteract the pathological protein conformers that are known—or presumed—to cause neurodegenerative disorders, such as amyloid pathology in AD caused, for example, by intra-neuronal aggregates of hyper-phosphorylated protein tau that are as typical for AD as amyloid.

This unmet need could be met within the scope of the present invention by providing passive and active immunization methods using liposome-based vaccines (Nicolau et al., 2002; Muhs et al., 2007) and mAbs based on phospho-peptides mimicking major pathological phospho-epitopes of protein tau. These combined actions generate novel specific mAbs against linear and conformational, simple and complex phospho-epitopes on protein tau that are thought to be responsible for synapto- and neuro-toxicity in tauopathies, including AD.

The present invention provides novel methods and antigenic peptides according to the invention and as described herein and functional fragments thereof including compositions comprising said antigenic peptides or fragments thereof for eliciting a highly specific, particularly a conformation specific, immune response in an organism, but particularly within an animal, particularly a mammal or a human, which is highly effective and capable of preventing or alleviating tauopathies, or the symptoms associated with tauopathies, a group of diseases and disorders associated with the formation of neurofibrillary lesions, the predominant brain pathology in this group of neurodegenerative disorders.

The present invention also relates to the antibodies, particularly monoclonal antibodies, including functional parts thereof, and pharmaceutical compositions comprising said antibodies, which are resulting from the highly specific, particularly the conformation specific, immune response in an organism upon administration of the antigenic peptide according to the invention and as described herein or a functional fragment thereof and the composition comprising said antigenic peptide or fragment thereof for preventing or alleviating tauopathies, or the symptoms associated with tauopathies, a group of diseases and disorders associated with the formation of neurofibrillary lesions, the predominant brain pathology in this group of neurodegenerative disorders.

This group of neurodegenerative disorders may be subdivided into two sub-categories. In a first category diseases or disorders are comprised which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, prion protein cerebral amyloid angiopathy and traumatic brain injury.

In a second category diseases or disorders are comprised without distinct amyloid pathology including, but not limited to, amyotrophic lateral sclerosis/parkinsonism-dementia complex, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pick's disease, progressive subcortical gliosis, progressive supranuclear panencephalitis.

In particular, the present invention provides novel methods and pharmaceutical compositions comprising the antigenic peptides according to the invention and as described herein or functional fragments thereof and antibodies, particularly monoclonal antibodies, including functional parts thereof obtainable upon administration of the antigenic peptides according to the invention and as described herein or functional fragments thereof to a host animal, for retaining or improving, but particularly for restoring, more particularly for completely restoring the cognitive memory capacity in a mammal, particularly a human, suffering from a disease or disorder associated with the formation of neurofibrillar lesions.

It is an object of the invention to provide an antigenic peptide, particularly a modified antigenic peptide or a functional fragment thereof and pharmaceutical compositions comprising said antigenic peptide or a functional fragment thereof, which peptide is obtainable from a tau protein. In particular, the invention relates to an antigenic peptide, particularly an antigenic phospho-peptide, or a functional fragment thereof, mimicking a major pathological phospho-epitope of protein tau, which peptide or fragment is further modified through attachment to or reconstitution into a carrier, a pharmaceutical composition comprising said antigenic peptide or a functional fragment thereof and a method of producing such a peptide or a functional fragment thereof and pharmaceutical composition, respectively, for the treatment of diseases and disorders which are caused by or associated with the formation of neurofibrillary lesions, the predominant brain pathology in tauopathy comprising a heterogeneous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy.

In one embodiment, the invention relates to an antigenic peptide or a functional fragment thereof and a pharmaceutical compositions comprising said antigenic peptide or a functional fragment thereof, which peptide or fragment comprises of between 5 amino acid residues and 30 amino acid residues, particularly of between 10 amino acid residues and 25 amino acid residues, particularly of between 12 amino acid residues and 22 amino acid residues, particularly of between 14 amino acid residues and 20 amino acid residues, particularly of between 16 amino acid residues and 18 amino acid residues, respectively, of an amino acid sequence selected from the group of sequences depicted in SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9 wherein said sequences feature a characteristic phosphorylation pattern which is associated with a pathologic condition or disorder, particularly a condition or disorder associated with the formation of neurofibrillary lesions.

In one embodiment, the present invention relates to a nucleic acid molecule or fragments thereof encoding the antigenic peptide or a functional fragment thereof selected from the group of sequences depicted in SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 2 and has substantially the same immunogenic activity as said antigenic peptide of SEQ ID NO: 2, wherein the amino acid residue corresponding to amino acid residue 18 (P-Tyr$_{18}$) of SEQ ID NO: 2 is phosphorylated (T1).

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 2, wherein amino acid residue 18 (P-Tyr$_{18}$) is phosphorylated (T1).

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 3 and SEQ ID NO: 4, respectively, and has substantially the same immunogenic activity as said antigenic peptide of SEQ ID NO: 3, wherein at least one, particularly at least 2, particularly at least 3, but especially all of amino acid residues corresponding to amino acid residues 202 (P-Ser$_{202}$), 205 (P-Thr$_{205}$), 212 (P-Thr$_{212}$), and 214 (P-Ser$_{214}$) of SEQ ID NO: 3 and 4, respectively, are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 3 and SEQ ID NO: 4, respectively, wherein at least one, particularly at least 2, particularly at least 3, but especially all of amino acid residues 202 (P-Ser$_{202}$), 205 (P-Thr$_{205}$), 212 (P-Thr$_{212}$), and 214 (P-Ser$_{214}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 4 and has substantially the same immunogenic activity as said antigenic peptide of SEQ ID NO: 4, wherein at least one, particularly at least 2 of amino acid residues corresponding to amino acid residues 202 (P-Ser$_{202}$) and 205 (P-Thr$_{205}$) of SEQ ID NO: 4 are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 4, wherein at least one, particularly at least 2 of amino acid residues 202 (P-Ser$_{202}$) and 205 (P-Thr$_{205}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 8%, particularly at least 85%, particularly at least 90%, particularly at least 95%, particularly at least 98%, particularly at least 99%, sequence identity to the sequence depicted in SEQ ID NO: 3 and has substantially the same immunogenic activity as said antigenic peptide of SEQ ID NO: 3, wherein at least one, particularly at least 2 of amino acid residues corresponding to amino acid residues 212 (P-Thr$_{212}$) and 214 (P-Ser$_{214}$) of SEQ ID NO: 3 are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 3, wherein at least one, particularly at least 2 of amino acid residues 212 (P-Thr$_{212}$) and 214 (P-Ser$_{214}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 5 and has substantially the same immunogenic activity as said antigenic peptide of SEQ ID NO: 5, wherein at least one, but especially all of amino acid residues corresponding to amino acid residues 396 (P-Ser$_{395}$) and 404 (P-Ser$_{404}$) of SEQ ID NO: 5 are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 5, wherein at least one, but especially all of amino acid residues 396 (P-Ser$_{396}$) and 404 (P-Ser$_{404}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 6 and has substantially the same immunogenic activity as said antigenic peptide of SEQ ID NO: 6, wherein at least one, but especially all of amino acid residues corresponding to amino acid residues 404 (P-Ser$_{404}$) and 409 (P-Ser$_{409}$) of SEQ ID NO: 6 are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 6, wherein at least one, but especially all of amino acid residues 404 (P-Ser$_{404}$) and 409 (P-Ser$_{409}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 7 and has substantially the same immunogenic activity as said antigenic peptide of SEQ ID NO: 7, wherein at least one, particularly at least 2, particularly a least 3, but especially all of amino acid residues corresponding to amino acid residues 202 (P-Ser$_{202}$), 205 (P-Thr$_{205}$). 212 (P-Thr$_{212}$), and 214 (P-Ser$_{214}$) of SEQ ID NO: 7 are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 7, wherein at least one, particularly at least 2, particularly a least 3, but especially all of amino acid residues 202 (P-Ser$_{202}$), 205 (P-Thr$_{205}$), 212 (P-Thr$_{212}$), and 214 (P-Ser$_{214}$) are phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 8 and has substantially the same immunogenic activity as said antigenic peptide of SEQ ID NO: 8, wherein the amino acid residue corresponding to amino acid residue 409 (P-Ser$_{409}$) of SEQ ID NO: 8 is phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 8, wherein the amino acid residue corresponding to amino acid residue 409 (P-Ser$_{409}$) of SEQ ID NO: 8 is phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence which shows at least 80%, particularly at least 85%, particularly at least 90%, particularly at least 95%, particularly at least 98%, particularly at least 99%, sequence identity to the sequence depicted in SEQ ID NO: 9 and has substantially the same immunogenic activity as said antigenic peptide of SEQ ID NO: 9, wherein the amino acid residue corresponding to amino acid residue 404 (P-Ser$_{404}$) of SEQ ID NO: 9 is phosphorylated.

In one embodiment, the invention relates to an antigenic peptide, particularly an antigenic peptide modified according to the present invention, or a functional fragment thereof and a pharmaceutical composition comprising said antigenic peptide or a functional fragment thereof, which peptide or fragment exhibits an amino acid sequence as depicted in SEQ ID NO: 9, wherein the amino acid residue corresponding to amino acid residue 404 (P-Ser$_{404}$) of SEQ ID NO: 9 is phosphorylated.

Also comprised by the present invention is a antigenic peptide modified according to the present invention or a functional fragment thereof and a pharmaceutical compositions comprising said modified antigenic peptide or a functional fragment thereof, which peptide is essentially identical to the above mentioned antigenic peptides as shown in SEQ ID NOs: 2 to 9 and has substantially the same immunogenic activity as said antigenic peptides of SEQ ID NOs: 2 to 9, but particular a variant peptide fragment that is a conservatively modified variant of said fragments, wherein the alterations result in the substitution of one or more amino acids, particularly of between one to 10 amino acids, more particularly of between one to 6 amino acids, even more particularly of between one to 4 amino acids, but especially of between one to 3 amino acids, with a chemically similar amino acid. Conservative substitution tables providing functionally similar amino acids are well known in the art and disclosed herein below. The conservative substitution is preferably to be made such that the overall net charge of the peptide and also the charge distribution over the peptide molecule remains essentially the same.

Also comprised by the present invention is a variant peptide fragment, particularly a variant antigenic peptide modified according to the present invention and a pharmaceutical composition comprising said variant peptide fragment, which peptide is essentially identical to the above identified fragments of the invention and has substantially the same biological activity of said fragments, wherein one or more amino acid residues are deleted.

In a further embodiment, the peptide according to the invention or a functional fragment thereof is provided in form of a polymer selected from the group consisting of a 2-mer, a 3-mer, a 4-mer, a 5-mer, a 6-mer, a 7-mer, a 8-mer, a 9-mer, a 10-mer, a 11-mer, a 12-mer, a 13-mer, a 14-mer, a 15-mer, a 16-mer, a 20-mer, a 30-mer and a 50-mer, wherein the monomer units constituting said polymer are always identical or are different monomer units and selected from the group consisting of a peptide according to the invention and as described herein, particularly a peptide as shown in SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9 or a functional fragment thereof and variant peptides.

In one embodiment, the antigenic peptide according to the invention and as described herein or a functional fragment thereof, is modified through attachment to or reconstitution into a carrier, particularly a carrier that has also functionality as an adjuvant resulting a supramolecular antigenic construct. In a specific embodiment, the antigenic peptide according to the invention and as described herein or a functional fragment thereof, is modified through attachment to or reconstitution into a liposome such as to produce an "supramolecular antigenic construct" as described in WO publication WO 2005/081872, the description of which is enclosed herewith by reference in its entirety. The antigenic peptide or a functional fragment thereof is further modified such that it exhibits a unique presentation of the antigenic peptide on the carrier surface, which leads to an enhanced exposure of the antigen and ultimately to the generation of antibodies which show a high degree of conformational sensitivity. In particular, the antigenic peptide according to the invention and as described herein, is modified through association with a lipophilic or hydrophobic moiety, that facilitates insertion into the lipid bilayer of the liposome carrier/immune adjuvant, particularly by a lipophilic or hydrophobic moiety which functions as an anchor for the peptide in the liposome bilayer and has a dimension that leads to the peptide being positioned and stabilized in close proximity to the liposome surface.

In a further embodiment of the invention, the lipophilic or hydrophobic moiety is a fatty acid, a triglyceride or a phospholipid, particularly a fatty acid, a triglyceride or a phospholipid containing a carbon chain of between C12 and C24, but especially a palmitic acid.

In a specific embodiment of the invention an antigenic peptide according to the invention and as described herein is provided, or a functional fragment thereof, modified by at least two molecules of palmitic acid covalently bound to the N- and C-terminal ends of said antigenic peptide or a functional fragment thereof, and by reconstitution into a liposomal carrier.

In one embodiment of the invention, the peptides or fragments in the conjugates are each coupled to four molecules of palmitic acid; they are therefore tetrapalmitoylated.

In one embodiment of the invention, two molecules of palmitic acid are coupled to the N-terminal end and two molecules of palmitic acid are coupled to the C-terminal end of the peptide or fragment.

In still a further embodiment, the present invention provides an antigenic peptide according to the invention and as described herein, or a functional fragment thereof, modified through association with a lipophilic or hydrophobic moiety such as, for example, palmitic acid and reconstituted in a liposome, wherein the liposomal preparation may in addition contain an adjuvant such as, for example, lipid A, alum, calcium phosphate, interleukin 1, and/or microcapsules of polysaccharides and proteins, but particularly a detoxified lipid A, such as monophosphoryl or diphosphoryl lipid A, or alum resulting in a supramolecular antigenic construct.

In one embodiment, the invention relates to a supramolecular construct of the invention and as described herein, which comprises per carrier molecule one or more antigenic peptides, particularly two or more antigenic peptides, according to the invention and as described herein, or a functional fragment thereof.

In one embodiment of the invention, said carrier molecule is a liposome.

In one embodiment of the invention, the two or more antigenic peptides are the same or different peptides, particularly peptides selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9 or functional fragments thereof and variant peptides.

In one embodiment, the invention relates to a supramolecular construct of the invention and as described herein, which comprises per carrier molecule a combination of two or more antigenic peptides of SEQ ID NO: 3 and SEQ ID NO: 4, or functional fragments thereof.

In one embodiment, the invention relates to an antibody, particularly a monoclonal antibody including any functionally equivalent antibody or functional parts thereof, which antibody recognizes and binds a phosphorylated pathological protein tau-conformer or those parts of the conformer which causes the pathological properties of said conformer, particularly a pathological phospho-epitope of protein tau.

In particular, the present invention provides an antibody, particularly a monoclonal antibody including any functionally equivalent antibody or functional parts thereof, which antibody recognizes and binds a phosphorylated, pathological protein tau-conformer or those parts of the conformer which causes the pathological properties of said conformer, particularly a pathological phospho-epitope of protein tau, with a high specificity.

In a specific embodiment, the antibody, particularly the monoclonal antibody including any functionally equivalent antibody or functional parts thereof according to the invention binds the pathological protein tau-conformer or those parts of the conformer causing the pathological properties of said conformer with an affinity that is at least 40%, particularly at least 50%, particularly at least 60%, particularly at least 70%, particularly at least 80%, particularly at least 90%, particularly at least 95% and up to 100% higher than the binding affinity for the unphosphorylated, non-pathologial tau conformer.

In a specific embodiment, an antibody, particularly a monoclonal antibody including any functionally equivalent antibody or functional parts thereof according to the invention is provided, which binds specifically to neurofibrillar tangles (NETS) and neuropil threads in human Alzheimer Disease brains.

It is another object of the present invention to provide antibodies, particularly monoclonal antibodies or functional parts thereof, that directly and specifically binds to an epitope on the tau protein, or to a combination of epitopes, particularly to an epitope specific to a phosphorylated, pathological protein tau-conformer, particularly a pathological phospho-epitope of protein tau such as, for example, an epitope as represented by or comprised in a peptide sequence selected from the group of sequences as given in SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9 and variant fragments thereof.

In particular, the present invention provides an antibody including any functionally equivalent antibody or functional parts thereof particularly a monoclonal antibody including any functionally equivalent antibody or functional parts thereof obtainable by immunizing a suitable animal with an antigenic peptide, particularly a peptide composition according to the invention and as described herein before, particularly a composition comprising an antigenic peptide comprising an amino acid sequence as given in SEQ ID NO: 2, SEQ ID NO: 3, SEQ ID NO: 4, SEQ ID NO: 5, SEQ ID NO: 6, SEQ ID NO: 7, SEQ ID NO: 8, and SEQ ID NO: 9, including a functional fragment or a variant fragment thereof.

In one embodiment, the invention relates to an antibody, particularly a monoclonal antibody including any functionally equivalent antibody or functional parts thereof, which antibody has the characteristic properties of an antibody produced by hybridoma cell line AC1-41-Ab1 deposited on Mar. 3, 2010 as DSM ACC3043. More particularly, the invention relates to an antibody, particularly a monoclonal antibody including any functionally equivalent antibody or functional parts thereof produced by hybridoma cell line AC1-41-Ab1 deposited on Mar. 3, 2010 as DSM ACC3043.

In one embodiment, the invention relates to an antibody, particularly a monoclonal antibody including any functionally equivalent antibody or functional parts thereof, which antibody has the characteristic properties of an antibody produced by hybridoma cell line 2B6 deposited on Mar. 10, 2010 as DSM ACC3044.

More particularly, the invention relates to an antibody, particularly a monoclonal antibody including any functionally equivalent antibody or functional parts thereof produced by hybridoma cell line 2B6 deposited on Mar. 10, 2010 as DSM ACC3044.

In one embodiment, the invention relates to an antibody, particularly a monoclonal antibody including any functionally equivalent antibody or functional parts thereof, which antibody has the characteristic properties of an antibody produced by hybridoma cell line 3A8 deposited on Mar. 10, 2010 as DSM ACC3045.

More particularly, the invention relates to an antibody, particularly a monoclonal antibody including any functionally equivalent antibody or functional parts thereof produced by hybridoma cell line 3A8 deposited on Mar. 10, 2010 as DSM ACC3045.

In one embodiment, the invention relates to an antibody, particularly a monoclonal antibody including any functionally equivalent antibody or functional parts thereof, which antibody has the characteristic properties of an antibody produced by hybridoma cell line 4C1 deposited on Mar. 10, 2010 as DSM ACC3046.

More particularly, the invention relates to an antibody, particularly a monoclonal antibody including any functionally equivalent antibody or functional parts thereof produced by hybridoma cell line 4C1 deposited on Mar. 10, 2010 as DSM ACC3046.

In one embodiment, the invention relates to an antibody, particularly a monoclonal antibody including any functionally equivalent antibody or functional parts thereof, which antibody has the characteristic properties of an antibody produced by hybridoma cell line 5O10A3 deposited on Mar. 10, 2010 as DSM ACC3047.

More particularly, the invention relates to an antibody, particularly a monoclonal antibody including any functionally equivalent antibody or functional parts thereof produced by hybridoma cell line 5D10A3 deposited on Mar. 10, 2010 as DSM ACC3047.

In one embodiment, the invention relates to an antibody, particularly a monoclonal antibody including any functionally equivalent antibody or functional parts thereof, which antibody has the characteristic properties of an antibody produced by hybridoma cell line 6C10 deposited on Mar. 10, 2010 as DSM ACC3048.

More particularly, the invention relates to an antibody, particularly a monoclonal antibody including any functionally equivalent antibody or functional parts thereof produced by hybridoma cell line 6C10 deposited on Mar. 10, 2010 as DSM ACC3048.

In one embodiment, the invention relates to an antibody, particularly a monoclonal antibody including any functionally equivalent antibody or functional parts thereof, which antibody has the characteristic properties of an antibody produced by hybridoma cell line 6H1 deposited on Mar. 10, 2010 as DSM ACC3049.

More particularly, the invention relates to an antibody, particularly a monoclonal antibody including any functionally equivalent antibody or functional parts thereof produced by hybridoma cell line 6H1 deposited on Mar. 10, 2010 as DSM ACC3049.

In one embodiment, the invention relates to an antibody, particularly a monoclonal antibody including any functionally equivalent antibody or functional parts thereof, which antibody has the characteristic properties of an antibody produced by hybridoma cell line 7C2 deposited on Mar. 10, 2010 as DSM ACC3050.

More particularly, the invention relates to an antibody, particularly a monoclonal antibody including any functionally equivalent antibody or functional parts thereof produced by hybridoma cell line 7C2 deposited on Mar. 10, 2010 as DSM ACC3050.

The antibody may be provided in form of a chimeric antibody or a humanized antibody still exhibiting the specific binding characteristics as disclosed above.

In one embodiment, the invention relates to a cell line producing an antibody of the invention as described herein.

In a specific embodiment, the invention relates to hybridoma cell line ACl-41-Ab1 deposited on Mar. 3, 2010 as DSM ACC3043.

In another specific embodiment, the invention relates hybridoma cell line 2B6 deposited on Mar. 10, 2010 as DSM ACC3044.

In another specific embodiment, the invention relates to hybridoma cell line 3A8 deposited on Mar. 10, 2010 as DSM ACC3045.

In another specific embodiment, the invention relates to hybridoma cell line 4C1 deposited on Mar. 10, 2010 as DSM ACC3046.

In another specific embodiment, the invention relates to hybridoma cell line 5D10A3 deposited on Mar. 10, 2010 as DSM ACC3047.

In another specific embodiment, the invention relates to hybridoma cell line 6C10 deposited on Mar. 10, 2010 as DSM ACC3048.

In another specific embodiment, the invention relates to hybridoma cell line 6H1 deposited on Mar. 10, 2010 as DSM ACC3049.

In another specific embodiment, the invention relates to hybridoma cell line 7C2 deposited on Mar. 10, 2010 as DSM ACC3050.

Also enclosed herewith are subclones and variant clones of the above listed specific hybridoma cell lines, which still produce an antibody with the specific tau-binding properties of the present invention.

In a specific embodiment the invention provides a pharmaceutical composition and a method of producing a pharmaceutical composition comprising an antigenic peptide fragment, particularly an antigenic peptide fragment modified through attachment to and/or reconstitution into a carrier, particularly a liposomal carrier, according to the invention and as described herein or a functional fragment thereof, together with a pharmaceutically acceptable carrier and/or diluent and/or excipient, for retention or improvement, particularly for complete restoration of the cognitive memory capacity of an animal, particularly a mammal or a human, suffering from memory impairment.

In one embodiment, a pharmaceutical composition is provided comprising an antibody including any functionally equivalent antibody or functional parts thereof particularly a monoclonal antibody including any functionally equivalent antibody or functional parts thereof according to the present invention in a therapeutically effective amount together with a pharmaceutically acceptable carrier and/or diluent and/or excipient.

It is also an object of the invention to provide a pharmaceutical composition according to the invention and as described herein, and/or a method, for the treatment of diseases and disorders which are caused by or associated with the formation of neurofibrillary lesions, the predominant brain pathology in tauopathy comprising a heterogeneous group of neurodegenerative diseases or disorders including diseases or disorders which show co-existence of tau and amyloid pathologies including, but not limited to, Alzheimer's Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further diseases or disorders which do not show a distinct amyloid pathology including, but not limited to, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy, said method comprising administering to an animal, particularly a mammal or a human, a pharmaceutical composition according to the invention and as described herein in a therapeutically effective amount together with a pharmaceutically acceptable carrier and/or diluent and/or excipient.

In a specific embodiment the invention provides pharmaceutical composition according to the invention and as described herein, and/or a method, for retaining or increasing cognitive memory capacity but, particularly, for fully restoring the cognitive memory capacity of an animal, particularly a mammal or a human, suffering from memory impairment, said method comprising administering to an animal, particularly a mammal or a human, a pharmaceutical composition according to the invention and as described herein in a therapeutically effective amount together with a pharmaceutically acceptable carrier and/or diluent and/or excipient.

It is another object of the invention to provide a pharmaceutical composition and a method of producing such a composition, as well as a method for inducing an immune response in an animal, particularly a mammal or a human suffering from a disease and condition which is caused by or associated with the formation of neurofibrillary lesions, by administering to said animal or human a pharmaceutical composition according to the invention in a therapeutically effective amount together with a pharmaceutically acceptable carrier and/or diluent and/or excipient.

In one embodiment of the invention, a method is provided for inducing an immune response in an animal, particularly a mammal or a human suffering from neurofibrillary lesions resulting in a tauopathy, to such an extent that a retention or improvement of the symptoms associated with this disease or condition such as, for example, memory impairment can be obtained, particularly a complete restoration of the original condition.

The pharmaceutical composition comprising an antigenic peptide according to the invention and as described herein upon administration to an animal, particularly a mammal, but especially a human, results mainly in the generation of antibodies of non-inflammatory Th2 subtypes such as, for example, isotype IgG1 and IgG2b and/or antibodies of the T-cell independent IgG subclass such as, for example, IgG3 and/or does not lead to a significant increase in inflammation markers in the brain, particularly of inflammation markers selected from the group consisting of IL-1 β, IL-6, IFN-γ and TNF α.

In a further aspect of the invention, the pharmaceutical composition comprising an antigenic peptide according to the invention and as described herein may be used for inducing a T-cell independent immune response upon treatment of a disease, condition or disorder in a patient, particularly an animal or human patient, particularly a patient in need of such a T-cell independent response such as, for example, an immune tolerant patient or a T-cell activated patient wherein said antigenic peptide is modified through attachment to and/or reconstitution into a carrier, particularly a liposomal carrier such that the antigen is presented on the surface of the carrier, particularly the liposome.

In one embodiment, the antigenic composition of the invention as described herein is effective as an immune stimulant.

In a specific embodiment of the invention, said peptide antigen is presented in a highly repetitive array on the surface of the liposome. In a further specific embodiment, said antigen does not contain a T-cell epitope.

In one embodiment of the invention, the antigenic composition of the invention as described herein is used for treating an immune tolerant patient or a T-cell activated patient, particularly a immunocompromised patient, particularly a patient suffering from an autoimmune disease, particularly a patient who suffers from a T-cell deficiency, particularly a T-cell deficiency, which is caused by a depletion within said patients of CD4 T-cells and/or a reduced expression of CD14 and/or the CD40L on CD4 T-cells.

The antibodies according to the invention may be used in a method of diagnosing a tau-protein-associated disease or condition in a patient comprising detecting the immunospecific binding of an antibody or an active fragment thereof to an epitope of the tau protein in a sample or in situ which includes the steps of
  (a) bringing the sample or a specific body part or body area suspected to contain the tau protein into contact with said antibody, which antibody binds an epitope of the tau protein;
  (b) allowing the antibody to bind to the tau protein to form an immunological complex;
  (c) detecting the formation of the immunological complex; and
  (d) correlating the presence or absence of the immunological complex with the presence or absence of tau protein in the sample or specific body part or area.

In one embodiment, a method is provided for diagnosing a predisposition to tau-protein-associated disease or condition in a patient comprising detecting the immunospecific binding of a monoclonal antibody or an active fragment thereof to an epitope of the tau protein in a sample or in situ which includes the steps of
  (a) bringing the sample or a specific body part or body area suspected to contain the tau antigen into contact with an antibody according to the invention and as described herein before, which antibody binds an epitope of the tau protein;
  (b) allowing the antibody to bind to the tau antigen to form an immunological complex:
  (c) detecting the formation of the immunological complex; and
  (d) correlating the presence or absence of the immunological complex with the presence or absence of tau antigen in the sample or specific body part or area,
  (e) comparing the amount of said immunological complex to a normal control value.
wherein an increase in the amount of said aggregate compared to a normal control value indicates that said patient is suffering from or is at risk of developing an tau protein-associated disease or condition.

In another embodiment, the invention relates to a method for monitoring minimal residual disease in a patient following treatment with an antibody or a pharmaceutical composition according to any one of the preceding claims, wherein said method comprises:
  (a) bringing the sample or a specific body part or body area suspected to contain the tau antigen into contact with an antibody according to the invention and as described herein before, which antibody binds an epitope of the tau protein;

(b) allowing the antibody to bind to the tau antigen to form an immunological complex;
(c) detecting the formation of the immunological complex; and
(d) correlating the presence or absence of the immunological complex with the presence or absence of tau antigen in the sample or specific body part or area,
(e) comparing the amount of said immunological complex to a normal control value, wherein an increase in the amount of said aggregate compared to a normal control value indicates that said patient still suffers from a minimal residual disease.

In still another embodiment, the invention provides a method for predicting responsiveness of a patient being treated with an antibody or a pharmaceutical composition according to any one of the preceding claims comprising
(a) bringing the sample or a specific body part or body area suspected to contain the tau antigen into contact with an antibody according to the invention and as described herein before, which antibody binds an epitope of the tau protein;
(b) allowing the antibody to bind to the tau antigen to form an immunological complex;
(c) detecting the formation of the immunological complex; and
(d) correlating the presence or absence of the immunological complex with the presence or absence of tau antigen in the sample or specific body part or area,
(e) comparing the amount of said immunological complex before and after onset of the treatment, wherein an decrease in the amount of said aggregate indicates that said patient has a high potential of being responsive to the treatment.

In another embodiment of the invention, the antibody according to the invention may be used in a test kit for detection and diagnosis of tau-associated diseases and conditions.

In particular, a test kit is provided for detection and diagnosis of tau protein-associated diseases and conditions comprising antibodies according to the invention, in particular a test kit comprising a container holding one or more antibodies according to the present invention and instructions for using the antibodies for the purpose of binding to tau antigen to form an immunological complex and detecting the formation of the immunological complex such that presence or absence of the immunological complex correlates with presence or absence of tau antigen.

These and other objects, features and advantages of the present invention will become apparent after a review of the following detailed description of the disclosed embodiment and the appended claims.

BRIEF DESCRIPTION OF FIGURES AND SEQUENCES

FIG. 1a: Anti-Tau5-20 [pY18] IgG antibodies in WT mice immunized with ACI-33. Analysis of anti-Tau5-20 [pY18] IgG antibodies in the sera of C57BL/6 wild-type mice receiving 3 injections of ACI-33 at d0, d13 and d28 and being bleed at d-1, d27 and d47. Results are expressed as mean O.D+ standard deviation obtained in the group of 6 mice.

FIG. 1b: Anti-Tau5-20 [pY18] IgG antibodies in TKO mice immunized with ACI-33. Analysis of anti-Tau5-20 [pY18] IgG antibodies in the sera of C57BL/6 wild-type mice receiving 3 injections of ACI-33 at d0, d13 and d28 and being bleed at d-1; d27 and d47. Results are expressed as mean O.D+ standard deviation obtained in the group of 6 mice.

FIG. 2a: Anti-Tau393-408 [pS396/pS404] IgG antibodies in WT mice immunized with ACI-35. Analysis of anti-Tau393-408 [pS396/pS404] IgG antibodies in the sera of C57BL/6 wild-type mice receiving 5 injections of ACI-35 at d0, d16, d30, d99 and d113 and being bleed at d-1, d28, d42 d98 and d126. Results are expressed as mean O.D+standard deviation obtained in the group of 6 mice.

FIG. 2b: Anti-Tau393-408 [pS396/pS404] IgG antibodies in TKO mice immunized with ACI-35. Analysis of anti-Tau393-408 [pS396/pS404] IgG antibodies in the sera of TKO mice receiving 5 injections of ACI-35 at d0, d16, d30, d99 and d113 and being bleed at d-1, d28, d42, d98 and d126. Results are expressed as mean O.D+standard deviation obtained in the group of 6 mice.

FIG. 3a: Anti-Tau401-418 [pS404/S409] IgG antibodies in WT mice immunized with ACI-36. Analysis of anti-Tau401-418 [pS404/S409] IgG antibodies in the sera of C57BL/6 wild-type mice receiving 3 injections of ACI-36 at d0, d13 and d28 and being bleed at d-1, d27 and d47. Results are expressed as mean O.D+standard deviation obtained in the group of 6 mice.

FIG. 3b: Anti-Tau401-418 [pS404/S409] IgG antibodies in TKO mice immunized with ACI-36. Analysis of anti-Tau401-418 [pS404/S409] IgG antibodies in the sera of TKO mice receiving 3 injections of ACI-36 at d0, d13 and d28 and being bleed at d-1, d27 and d47. Results are expressed as mean O.D+standard deviation obtained in the group of 6 mice for d-1/d27 and in the group of 5 mice for d47.

FIG. 4a/4b: Anti-Tau206-221 [pT212/pS214] and anti-Tau196-211 [pS202/pT205] IgG antibodies in WT mice immunized with ACI-41. Analysis of anti-Tau206-221 [pT212/pS214] and anti-Tau196-211 [pS202/pT205] IgG antibodies in the sera of C57BL/6 wild-type mice receiving 3 injections of ACI-41 at d0, d20, d35 and being bleed at d-1, d34, d48. Results are expressed as mean O.D+standard deviation obtained in the group of 6 mice. Same sera were tested on both pTau peptides.

FIG. 4c/4d: Anti-Tau206-221 [pT212/pS214] and anti-Tau196-211 [pS202/pT205] IgG antibodies in TKO mice immunized with ACI-41. Analysis of anti-Tau206-221 [pT212/pS214] and anti-Tau196-211 [pS202/pT205] IgG antibodies in the sera of TKO mice receiving 3 injections of ACI-41 at d0, d20, d35 and being bleed at d-1, d34, d48. Results are expressed as mean OD+standard deviation obtained in the group of 6 mice. Same sera were tested on both pTau peptides.

FIG. 5a: Anti-Tau5-20 [pY18] IgG isotypes and IgM antibodies in WT mice immunized with ACI-33. Analysis of anti-Tau5-20 [pY18] IgG1, 2a, 2b, 3 and IgM antibodies in the sera of C57BL/6 mice 47 days after the first ACI-33 immunization. Results are expressed as O.D. at a dilution of 1/100 (IgG1), 1/100 (IgG2a), 1/100 (IgG2b), 1/100 (IgG3) and 1/3200 (IgM) showing mean+standard deviation obtained in the group of 6 mice.

FIG. 5b: Anti-Tau5-20 [pY18] IgG isotypes and IgM antibodies in TKO mice immunized with ACI-33, Analysis of anti-Tau5-20 [pY18] IgG1, 2a, 2b, 3 and IgM antibodies in the sera of TKO mice 47 days after the first ACI-33 immunization. Results are expressed as O.D. at a dilution of 1/100 (IgG1), 1/100 (IgG2a), 1/100 (IgG2b), 1/100 (IgG3) and 1/3200 (IgM) showing mean+standard deviation obtained in the group of 6 mice.

FIG. 6a: Anti-Tau393-408 [pS396/pS404] IgG isotypes and IgM antibodies in WT mice immunized with ACI-35. Analysis of anti-Tau393-408 [pS396/pS404] IgG1, 2a, 2b, 3 and IgM antibodies in the sera of C57BL/6 mice 42 days after the first ACI-35 immunization. Results are expressed as O.D.

at a dilution of 1/100 (IgG1), 1/1600 (IgG2a), 1/1600 (IgG2b), 1/800 (IgG3) and 1/1600 (IgM) showing mean+ standard deviation obtained in the group of 6 mice FIG. 6b: Anti-Tau393-408 [pS396/pS404] IgG isotypes and IgM antibodies in TKO mice immunized with ACI 35. Analysis of anti-Tau393-408 [pS396/S404] IgG1, 2a, 2b, 3 and IgM antibodies in the sera of TKO mice 42 days after the first ACl-35 immunization. Results are expressed as O.D. at a dilution of 1/100 (IgG1), 1/1600 (IgG2a), 1/1600 (IgG2b), 1/800 (IgG3) and 1/1600 (IgM) showing mean+standard deviation obtained in the group of 6 mice.

FIG. 7a: Anti-Tau401-418 [pS404/S409] IgG isotypes and IgM antibodies in WT mice immunized with ACl-36, Analysis of anti-Tau401-418 [pS404/S409] IgG1, 2a, 2b, 3 and IgM antibodies in the sera of C57BL/6 mice 47 days after the first ACl-36 immunization. Results are expressed as O.D. at a dilution of 1/100 (IgG1), 1/400 (IgG2a), 1/400 (IgG2b), 1/100 (IgG3) and 1/400 (IgM) showing mean+standard deviation obtained in the group of 6 mice.

FIG. 7b: Anti-Tau401-418 [pS404/S409] IgG isotypes and IgM antibodies in TKO mice immunized with ACl-36. Analysis of anti-Tau401-418 [pS404/S409] IgG1, 2a, 2b, 3 and IgM antibodies in the sera of TKO mice 47 days after the first ACl-36 immunization. Results are expressed as O.D. at a dilution of 1/100 (IgG1), 1/100 (IgG2a), 1/100 (IgG2b), 1/100 (IgG3) and 1/400 (IgM) showing mean+standard deviation obtained in the group of 5 mice.

FIG. 8a: Anti-Tau196-211 [pS202/pT205] IgG isotypes and IgM antibodies in WT mice immunized with ACl-41, Analysis of anti-Tau196-211 [pS202/pT205] IgG1, 2a, 2b, 3 and IgM antibodies in the sera of C57BL/6 mice 48 days after the first ACl-41 immunization. Results are expressed as O.D. at a dilution of 1/100 (IgG1), 1/100 (IgG2a), 1/3200 (IgG2b), 1/1600 (IgG3) and 1/3200 (IgM) showing mean+standard deviation obtained in the group of 6 mice.

FIG. 8b: Anti-Tau196-211 [pS202/pT205] IgG isotypes and IgM antibodies in TKO mice immunized with ACl-41. Analysis of anti-Tau196-211 [pS202/pT205] IgG1, 2a, 2b, 3 and IgM antibodies in the sera of TKO mice 48 days after the first ACl-41 immunization. Results are expressed as O.D. at a dilution of 1/100 (IgG1), 1/100 (IgG2a), 1/3200 (IgG2b), 1/1600 (IgG3) and 1/3200 (IgM) showing mean+standard deviation obtained in the group of 6 mice.

FIG. 9a/9b; ACl-36 Hybridoma supernatants from T25 flasks: TAUPIR and Tau ELISA screen. 9a. TAUPIR staining of old biGT mouse using undiluted supernatant. 9b. Analysis of anti-pTau peptide T4.5, anti-Tau peptide T4.6, anti-pTau protein and anti-Tau protein titers of undiluted clone supernatant samples. Results are expressed as O.D.

FIG. 10a/10b/10c: ACl-41 Hybridoma supernatants from T25 flasks: TAUPIR and Tau ELISA screen. 10a. TAUPIR staining of old biGT mouse using undiluted supernatant. 10b. Analysis of anti-pTau peptide T8.5, anti-Tau peptide T8.6, anti-pTau protein and anti-Tau protein titers of undiluted clone supernatant samples. Results are expressed as O.D. 10c. Analysis of anti-pTau peptide T9.5, anti-Tau peptide T9.6, anti-pTau protein and anti-Tau protein titers of undiluted clone supernatant samples. Results are expressed as O.D.

FIG. 11: Hybridoma supernatant on plate coted with 78: Tau206-221 [pT212/pS214], T9: Tau196-211 [pS202/pT205] and hP-Tau. Analysis of anti-Tau206-221 [pT212/pS214], anti-Tau196-211 [pS202/pT205] and anti-hP-Tau antibodies from hybridoma clones supernatant. Results are expressed as O.D. Same supernatant was tested undiluted on both pTau peptides and hP-Tau.

FIG. 12: Antibody clone ACl-41-Ab1 (T89-F4) stains NFTs in human AD brains. Brain sections from AD (a, b, and c), PSP (progressive supranuclear palsy) (d, e, and f), and healthy control (g, h, and i) subjects were stained using AT100 (a, d, and g), or ACl-41-Ab1 (T89-F4) at 1/1 (b, e, and h) or at 1/30 (c, f, and i) dilutions.

FIG. 13: Antibody 5D10 stains NFTs in human AD brains. Cortical brain sections from AD subjects were stained using 5D10 (a) or AT100 (b) antibodies.

FIG. 14: Anti-Tau393-408 [pS396/pS404] IgG antibodies in mice immunized with ACl-35. Analysis of anti-Tau393-408 [pS396/pS404] IgG antibodies in the plasma of C57BL/6 mice receiving 3 injections of ACl-35 at d0, d14 and d28 and being bled at d-7, d7, d21, d35 and d56. Results are expressed as mean O.D.+standard deviation obtained in the groups of 10 mice.

FIG. 15: Anti-Tau393-408 [pS396/pS404] IgG isotypes antibodies in mice immunized with ACl-35. Analysis of anti-Tau393-408 [pS396/pS404] IgG1, 2a, 2b and 3 antibodies in the plasma of C57BL/6 mice 35 days after the first ACl-35 immunization. Results are expressed as O.D. at a non-saturated dilution of 1/1600 (IgG1), 1/3200 (IgG2a), 1/3200 (IgG2b) and 1/800 (IgG3) showing mean+standard deviation obtained in the groups of 10 mice.

FIG. 16a: Anti-Tau393-408 [pS396/S404] IgM antibodies in mice immunized with ACl-35. Analysis of Tau393-408 [pS396/S404] IgM antibodies in the plasma of C57BL/6 mice 35 days after the first ACl-35 immunization. Results are expressed as O.D. at a dilution of 1/6400 showing mean+ standard deviation obtained in the groups of 10 mice.

FIG. 16b: Anti-Tau393-408 IgG antibodies in mice immunized with ACl-35. Analysis of Tau393-408 IgG antibodies in the plasma of C57BL/6 mice 35 days after the first ACl-35 immunization. Results are expressed as O.D. at a dilution of 1/100 showing mean+standard deviation obtained in the groups of 10 mice.

FIG. 17: Proliferation of cells from spleen restimulated with Con A or pTau/Tau peptide. Analysis of Tau-specific T cell proliferation by MTT at d56. Splenocytes were pooled from 10 mice of each group and restimulated with ConA, Tau393-408 [pS396/S404] or Tau393-408 peptides.

FIG. 18: Cytokine production by ELISPOT of splenocytes restimulated with Tau393-408 [pS396/S404] and Tau393-408 peptides, ELISPOT analysis of cytokine production by P-Tau/Tau-specific T cells. Splenocytes were pooled from 10 mice of each group and re-stimulated with Tau393-408 [pS396/S404] and Tau393-408 peptides.

FIG. 19: Anti-Tau5-20 [pY18] IgG antibodies in mice immunized with ACl-33. Analysis of anti-Tau5-20 [pY18] IgG antibodies in the sera of TPLH mice receiving 5 injections of ACl-33 at d0, d13, d28, d91 and d133 and being bleed at d-1, d27, d41, d76, d104 and d135. Results are expressed as mean O.D+standard deviation obtained in the group mice. d-1 n=10 mice. d27, d41 and d76 n=9 mice, 1 mouse died because of fighting. d104 n=6, 3 mice died from the pathology. d135 n=2, 4 mice died of the pathology.

FIG. 20: Anti-Tau393-408 [pS396/pS404] IgG antibodies in mice immunized with ACl-35. Analysis of anti-Tau393-408 [pS396/pS404] IgG antibodies in the sera of TPLH mice receiving 5 injections of ACl-35 at d0, d13, d27, d91 and d133 and being bleed at d-1, d26, d40, d75, d103, d145 and d155. Results are expressed as mean O.D+standard deviation obtained in the group mice, d-1, d26 n=10 mice. d40 n=9 mice. d75 n=6. d103 and d145 n=4. d155 n=3. All mice died of the pathology.

FIG. 21: Anti-Tau206-221 [pT212, pS214] IgG antibodies in mice immunized with ACl-39. Analysis of anti-Tau206-

221 [pT212, pS214] IgG antibodies in the sera of TPLH mice receiving 5 injections of ACI-39 at d0, d13, d28, d91 and d133 and being bleed at d-1, d27, d41, d76, d104 and d135. Results are expressed as mean O.D+standard deviation obtained in the group mice. d-1, d27 and d41 n=10 mice, d76 n=7 mice, d104 n=6, d135 n=2. All mice died of the pathology.

FIG. 22: Anti-Tau196-211 [pS202, pT205] IgG antibodies in mice immunized with ACl-40. Analysis of anti-Tau196-211 [pS202, pT205] IgG antibodies in the sera of TPLH mice receiving 5 injections of ACl-40 at d0, d13, d28, d91 and d133 and being bleed at d-1, d27, d41, d76, d104 and d135. Results are expressed as mean O.D+standard deviation obtained in the group mice. d-1, d27 and d41 n=10 mice, d76 n=8 mice, d104 n=6, d135 n=5. All mice died of the pathology.

FIG. 23: Anti-Tau5-20 [pY18] IgG isotypes and IgM antibodies in mice immunized with ACl-33. Analysis of anti-Tau5-20 [pY18] IgG1, 2a, 2b, 3 and IgM antibodies in the sera of TPLH mice at d41 after three ACl-33 immunizations. Results are expressed as non-saturated O.D. at a dilution of 1/100 (IgG1), 1/200 (IgG2a), 1/100 (IgG2b), 1/100 (IgG3) and 1/100 (IgM) showing mean+standard deviation obtained in the group of 9 mice.

FIG. 24: Anti-Tau393-408 [pS396/pS404] IgG isotypes and IgM antibodies in mice immunized with ACl-35. Analysis of anti-Tau393-408 [pS396/pS404] IgG1, 2a, 2b, 3 and IgM antibodies in the sera of TPLH mice at d40 after three ACl-35 immunizations. Results are expressed as non-saturated O.D. at a dilution of 1/100 (IgG1), 1/100 (IgG2a), 1/100 (IgG2b), 1/100 (IgG3) and 1/100 (IgM) showing mean+standard deviation obtained in the group of 9 mice.

FIG. 25: Anti-Tau206-221 [pT212, pS214] IgG isotypes and IgM antibodies in mice immunized with ACl-39. Analysis of anti-Tau206-221 [pT212, pS214] IgG1, 2a, 2b, 3 and IgM antibodies in the sera of TPLH mice at d41 after three ACl-39 immunizations. Results are expressed as non-saturated O.D. at a dilution of 1/100 (IgG1), 1/200 (IgG2a), 1/200 (IgG2b), 1/100 (IgG3) and 1/100 (IgM) showing mean+standard deviation obtained in the group of 10 mice.

FIG. 26: Anti-Tau196-211 [pS202, pT205] IgG isotypes and IgINA antibodies in mice immunized with ACl-40. Analysis of anti-Tau196-211 [pS202, pT205] IgG1, 2a, 2b, 3 and IgM antibodies in the sera of TPLH mice at d41 after three ACl-40 immunizations. Results are expressed as non-saturated O.D. at a dilution of 1/100 (IgG1), 1/400 (IgG2a), 1/200 (IgG2b), 1/800 (IgG3) and 1/100 (IgM) showing mean+standard deviation obtained in the group of 10 mice.

FIG. 27: IgG antibodies titers on different Tau peptides and proteins in mice immunized with ACl-33. Analysis IgG antibodies titers in the d-1 and d41 sera of TPLH mice after 3 injections of ACl-33. Results are expressed as O.D. showing mean+standard deviation obtained in the group of 9 mice.

FIG. 28: IgG antibodies titers on different Tau peptides and proteins in mice immunized with ACl-35. Analysis IgG antibodies titers in the d-1 and d40 sera of TPLH mice after 3 injections of ACl-35. Results are expressed as O.D. showing mean+standard deviation obtained in the group of 9 mice.

FIG. 29: IgG antibodies titers on different Tau peptides and proteins in mice immunized with ACl-39. Analysis IgG antibodies titers in the d-1 and d41 sera of TPLH mice after 3 injections of ACl-39. Results are expressed as O.D. showing mean+standard deviation obtained in the group of 10 mice.

FIG. 30: IgG antibodies titers on different Tau peptides and proteins in mice immunized with ACl-40, Analysis IgG antibodies titers in the d-1 and d41 sera of TPLH mice after 3 injections of ACl-40. Results are expressed as O.D. showing mean+standard deviation obtained in the group of 10 mice.

FIG. 31: Rotarod of mice immunized with ACl-33 versus PBS injected mice. Rotarod trials were performed on five different occasions referred by age (months) of the TPLH mice.

FIG. 32: Correlation between anti-Tau5-20 [pY18] antibody titers and rotarod test. Correlation was measured for the ACl-33 injected TPLH at age 7.8 months. Antibodies titers in mouse serum was measured by ELISA (O.D.) and the rotarod test measured the time the animals stayed on the apparatus (time).

FIG. 33: Rotarod of mice immunized with ACl-35 versus PBS injected mice. Rotarod results of 9.5 mice TPLH mice immunized with ACl-35 vs PBS control group. ACl-35 n=5 and PBS n=4 the other mice died because of the pathology displayed by the model FIG. 34: CD3+CD4+ quantification by FACS in nude and wild-type mice treated with ACl-33. The percent gated cells, which were stained positive for CD3 and CD4, of nude or wt mice or receiving ACl-33. Left panel: schematic representation of FACS analysis in two mice of nude and wt groups. Right panel: Each column represents mean and SD for groups of 6 mice. Mouse#5 and 6: nude mice, Mouse#7 and 8: wild type mice FIG. 35: Anti-Tau5-20 [pY18] IgG antibodies in nude and wt mice immunized with ACl-33. Analysis of anti-Tau5-20 [pY18] IgG antibodies in the sera of nude and wt mice receiving 3 injections of ACl-33 at d0, d14 and d28 and being bleed at d2, d7, d21, d35 and d56. Results are expressed as mean O.D+standard deviation obtained in the group of 6 mice.

Figure 36:
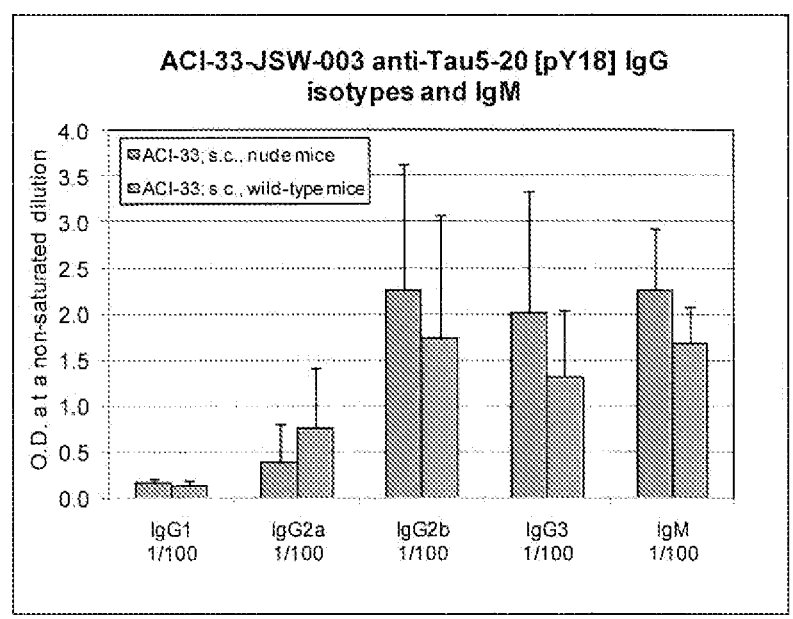

FIG. 36: Anti-Tau5-20 [pY18] IgG isotypes and IgM antibodies in nude and wt mice immunized with ACl-33. Analysis of anti-Tau5-20 [pY18] IgG1, 2a, 2b, 3 and IgM antibodies in the sera of nude and wt mice at d35 after three ACl-33 immunizations. Results are expressed as non-saturated O.D. at a dilution of 1/100 (IgG1), 1/100 (IgG2a), 1/100 (IgG2b), 1/100 (IgM) and 1/100 (IgM) showing mean+standard deviation obtained in the group of 6 mice.

Figure 37:
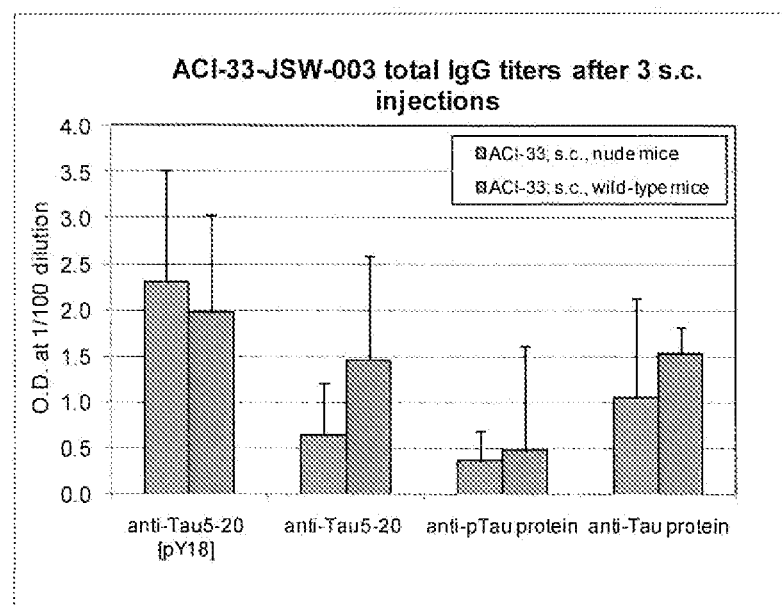

FIG. 37: IgG antibodies titers on different Tau peptides and proteins in nude and wt mice immunized with ACl-33. Analysis IgG antibodies titers in the d35 sera of nude and wt mice after 3 injections of ACl-33. Results are expressed as O.D. showing mean+standard deviation obtained in the group of 6 mice.

Figure 38:
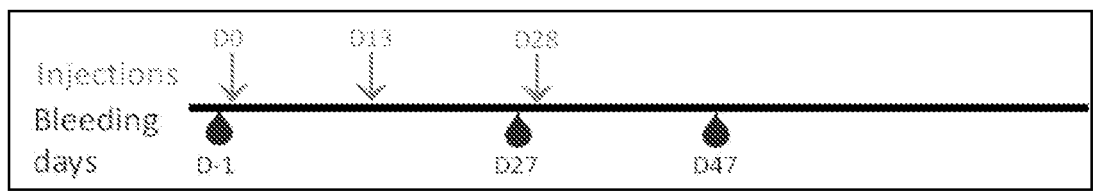

FIG. 38: Is a diagram showing an example immunization schedule used to generate tau antibodies in accordance with certain example embodiments.

Figure 39:
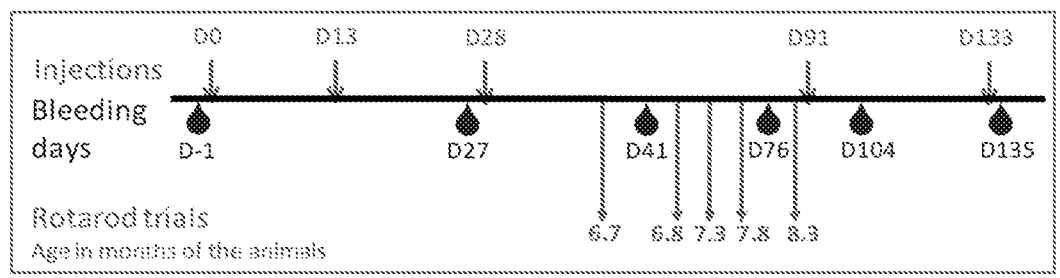

FIG. 39: Is a diagram showing an example immunization schedule used in a rotarod trial in accordance with certain example embodiments.

Figure 40:
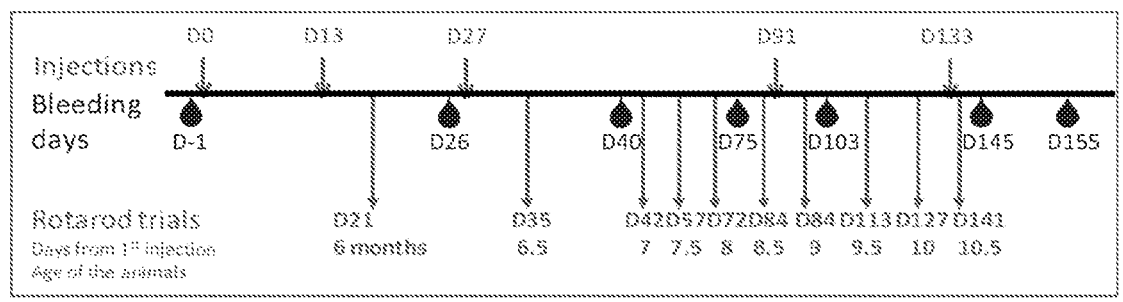

FIG. 40: Is a diagram showing an example immunization schedule used in a rotarod trial in accordance with certain example embodiments.

SEQ ID NO: 1 Amino acid sequence of control Sequence T5: Tau 379-408 [pS396, pS404]

SEQ ID NO: 2 Amino acid sequence of Sequence 1 (T1): Tau 5-20 [pY18]

SEQ ID NO: 3 Amino acid sequence of Sequence 8 (T8): Tau 206-221 [pT212, pS214]

SEQ ID NO: 4 Amino acid sequence of Sequence 9 (T9): Tau 196-211 [pS202, pT205]

SEQ ID NO: 5 Amino acid sequence of Sequence 3 (T3): Tau 393-408 [pS396, pS404]

SEQ ID NO: 6 Amino acid sequence of Sequence 4 (T4): Tau 401-418 [pS404, pS409]

SEQ ID NO: 7 Amino acid sequence of Sequence 2 (T2): Tau 200-216 [pS202+pT205 & pT212+pS214]

SEQ ID NO: 8 Amino acid sequence of Sequence 10 (T10): Tau 407-418 [pS409]

SEQ ID NO: 9 Amino acid sequence of Sequence 11 (T11): Tau 399-408 [pS404]

DEFINITION OF TERMS

The terms "polypeptide", "peptide", and "protein", as used herein, are interchangeable and are defined to mean a biomolecule composed of amino acids linked by a peptide bond.

The term "peptides," are chains of amino acids (typically L-amino acids) whose alpha carbons are linked through peptide bonds formed by a condensation reaction between the carboxyl group of the alpha carbon of one amino acid and the amino group of the alpha carbon of another amino acid. The terminal amino acid at one end of the chain (i.e., the amino terminal) has a free amino group, while the terminal amino acid at the other end of the chain (i.e., the carboxy terminal) has a free carboxyl group. As such, the term "amino terminus" (abbreviated N-terminus) refers to the free alpha-amino group on the amino acid at the amino terminal of the peptide, or to the alpha-amino group (imino group when participating in a peptide bond) of an amino acid at any other location within the peptide. Similarly, the term "carboxy terminus" (abbreviated C-terminus) refers to the free carboxyl group on the amino acid at the carboxy terminus of a peptide, or to the carboxyl group of an amino acid at any other location within the peptide.

The terms "fragment thereof" or "fragment" as used herein refer to a functional peptide fragment which has essentially the same (biological) activity as the peptides defined herein (e.g. as shown in SEQ ID NOs 2 to 9, respectively), i.e. said fragments are still capable of eliciting a highly specific, particularly a conformation specific, immune response in an organism, but particularly within an animal, particularly a mammal or a human, which is highly effective and capable of preventing or alleviating tauopathies, or the symptoms associated with tauopathies. In particular, said fragments still contain the specific pathological phospho-epitope or -epitopes of the tau peptide, as used and defined herein.

Typically, the amino acids making up a peptide are numbered in order, starting at the amino terminal and increasing in the direction toward the carboxy terminal of the peptide. Thus, when one amino acid is said to "follow" another, that amino acid is positioned closer to the carboxy terminal of the peptide than the preceding amino acid.

The term "residue" is used herein to refer to an amino acid that is incorporated into a peptide by an amide bond. As such, the amino acid may be a naturally occurring amino acid or, unless otherwise limited, may encompass known analogs of natural amino acids that function in a manner similar to the naturally occurring amino acids (i.e., amino acid mimetics). Moreover, an amide bond mimetic includes peptide backbone modifications well known to those skilled in the art.

The phrase "consisting essentially of" is used herein to exclude any elements that would substantially alter the essential properties of the peptides to which the phrase refers. Thus, the description of a peptide "consisting essentially of . . . " excludes any amino acid substitutions, additions, or deletions that would substantially alter the biological activity of that peptide.

Furthermore, one of skill will recognize that, as mentioned above, individual substitutions, deletions or additions which alter, add or delete a single amino acid or a small percentage of amino acids (typically less than 5%, more typically less than 1%) in an encoded sequence are conservatively modified variations where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T):
2) Aspartic acid (D), Glutamic acid (E);
3) Asparagine (N), Glutamine (Q):
4) Arginine (R), Lysine (K);
5) Isoleucine (I), Leucine (L), Methionine (M), Valine (V); and
6) Phenylalanine (F), Tyrosine (Y), Tryptophan (W).

The phrases "isolated" or "biologically pure" refer to material which is substantially or essentially free from components which normally accompany it as found in its native state. Thus, the peptides described herein do not contain materials normally associated with their in situ environment. Typically, the isolated, immunogenic peptides described herein are at least about 80% pure, usually at least about 90%, and preferably at least about 95% as measured by band intensity on a silver stained gel.

Protein purity or homogeneity may be indicated by a number of methods well known in the art, such as polyacrylamide gel electrophoresis of a protein sample, followed by visualization upon staining. For certain purposes high resolution will be needed and HPLC or a similar means for purification utilized.

When the immunogenic peptides are relatively short in length (i.e., less than about 50 amino acids), they are often synthesized using standard chemical peptide synthesis techniques.

Solid phase synthesis in which the C-terminal amino acid of the sequence is attached to an insoluble support followed by sequential addition of the remaining amino acids in the sequence is a preferred method for the chemical synthesis of the immunogenic peptides described herein. Techniques for solid phase synthesis are known to those skilled in the art.

Alternatively, the immunogenic peptides described herein are synthesized using recombinant nucleic acid methodology. Generally, this involves creating a nucleic acid sequence that encodes the peptide, placing the nucleic acid in an expression cassette under the control of a particular promoter, expressing the peptide in a host, isolating the expressed peptide or polypeptide and, if required, renaturing the peptide. Techniques sufficient to guide one of skill through such procedures are found in the literature.

Once expressed, recombinant peptides can be purified according to standard procedures, including ammonium sulfate precipitation, affinity columns, column chromatography, gel electrophoresis and the like. Substantially pure compositions of about 50% to 95% homogeneity are preferred, and 80% to 95% or greater homogeneity is most preferred for use as therapeutic agents.

One of skill in the art will recognize that after chemical synthesis, biological expression or purification, the immunogenic peptides may possess a conformation substantially different than the native conformations of the constituent peptides. In this case, it is often necessary to denature and reduce the antiproliferative peptide and then to cause the peptide to re-fold into the preferred conformation. Methods of reducing and denaturing proteins and inducing re-folding are well known to those of skill in the art.

Antigenicity of the purified protein may be confirmed, for example, by demonstrating reaction with immune serum, or with antisera produced against the protein itself.

The terms "a", "an" and "the" as used herein are defined to mean "one or more" and include the plural unless the context is inappropriate.

The terms "detecting" or "detected" as used herein mean using known techniques for detection of biologic molecules such as immunochemical or histological methods and refer to qualitatively or quantitatively determining the presence or concentration of the biomolecule under investigation.

By "isolated" is meant a biological molecule free from at least some of the components with which it naturally occurs.

The terms "antibody", "antibodies" or "functional parts thereof" as used herein is an art recognized term and is understood to refer to molecules or active fragments of molecules that bind to known antigens, particularly to immunoglobulin molecules and to immunologically active portions of immunoglobulin molecules, i.e molecules that contain a binding site that immunospecifically binds an antigen. The immunoglobulin according to the invention can be of any type (IgG, IgM, IgD, IgE, IgA and IgY) or class (IgG1, IgG2, IG3, IgG4, IgA1 and IgA2) or subclasses of immunoglobulin molecule.

"Antibodies" are intended within the scope of the present invention to include monoclonal antibodies, polyclonal, chimeric, single chain, bispecific, simianized, human and humanized antibodies as well as active fragments thereof. Examples of active fragments of molecules that bind to known antigens include Fab and F(ab')$_2$ fragments, including the products of a Fab immunoglobulin expression library and epitope-binding fragments of any of the antibodies and fragments mentioned above. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

A "humanized antibody" refers to a type of engineered antibody having its CDRs derived from a non-human donor immunoglobulin, the remaining immunoglobulin-derived parts of the molecule being derived from one (or more) human immunoglobulin(s).

A humanized antibody may further refer to an antibody having a variable region where one or more of its framework regions have human or primate amino acids. In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technoloy, 9:421 (1991)).

A "humanized antibody" may also be obtained by a novel genetic engineering approach that enables production of affinity-matured humanlike polyclonal antibodies in large animals such as, for example, rabbits (http://www.rctech.com/bioventures/therapeutic.php).

The term "monoclonal antibody" is also well recognized in the art and refers to an antibody that is mass produced in the laboratory from a single clone and that recognizes only one antigen. Monoclonal antibodies are typically made by fusing a normally short-lived, antibody-producing B cell to a fast-growing cell, such as a cancer cell (sometimes referred to as an "immortal" cell). The resulting hybrid cell, or hybridoma, multiplies rapidly, creating a clone that produces large quantities of the antibody.

The term "antigen" refers to an entity or fragment thereof which can induce an immune response in an organism, particularly an animal, more particularly a mammal including a human. The term includes immunogens and regions responsible for antigenicity or antigenic determinants.

As used herein, the term "soluble" means partially or completely dissolved in an aqueous solution.

Also as used herein, the term "immunogenic" refers to substances which elicit or enhance the production of antibodies, T-cells and other reactive immune cells directed against an immunogenic agent and contribute to an immune response in humans or animals.

An immune response occurs when an individual produces sufficient antibodies, T-cells and other reactive immune cells against administered immunogenic compositions of the present invention to moderate or alleviate the disorder to be treated.

The term "hybridoma" is art recognized and is understood by those of ordinary skill in the art to refer to a cell produced by the fusion of an antibody-producing cell and an immortal cell, e.g. a multiple myeloma cell. This hybrid cell is capable of producing a continuous supply of antibody. See the definition of "monoclonal antibody" above and the Examples below for a more detailed description of the method of fusion.

The term "carrier" as used herein means a structure in which antigenic peptide or supramolecular construct can be incorporated into or can be associated with, thereby presenting or exposing antigenic peptides or part of the peptide to the immune system of a human or animal. Any particle that can be suitably used in animal or human therapy such as, for example, a vesicle, a particle or a particulate body may be used as a carrier within the context of the present invention.

The term "carrier" further comprises methods of delivery wherein supramolecular antigenic construct compositions comprising the antigenic peptide may be transported to desired sites by delivery mechanisms. One example of such a delivery system utilizes colloidal metals such as colloidal gold.

Carrier proteins that can be used in the supramolecular antigenic construct compositions of the present invention include, but are not limited to, maltose binding protein "MBP"; bovine serum albumin "BSA"; keyhole lympet hemocyanin "KLH"; ovalbumin; flagellin; thyroglobulin; serum albumin of any species; gamma globulin of any species; syngeneic cells; syngeneic cells bearing Ia antigens; and polymers of D- and/or L-amino acids.

In the "supramolecular antigenic construct" according to the present invention, the liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. It is also to be understood that the supramolecular antigenic construct compositions of the present invention can further comprise additional adjuvants including, but not limited to, keyhole limpet hemocyanin (KLH), bovine serum albumin (BSA) and other adjuvants such as, for example, lipid A, alum, calcium phosphate, interleukin 1, and/or microcapsules of polysaccharides and proteins, but particularly a detoxified lipid A, such as monophosphoryl or diphosphoryl lipid A, or alum, further preservatives, diluents, emulsifiers, stabilizers, and other components that are known and used in vaccines of the prior art. Moreover, any adjuvant system known in the art can be used in the composition of the present invention. Such adjuvants include, but are not limited to, Freund's incomplete adjuvant, Freund's complete adjuvant, polydispersed β-(1,4)

linked acetylated mannan ("Acemannan"), TITERMAX® (polyoxyethylene-polyoxypropylene copolymer adjuvants from CytRx Corporation), modified lipid adjuvants from Chiron Corporation, saponin derivative adjuvants from Cambridge Biotech, killed *Bordetella pertussis*, the lipopolysaccharide (LPS) of gram-negative bacteria, large polymeric anions such as dextran sulfate, and inorganic gels such as alum, aluminum hydroxide, or aluminum phosphate.

Further, the term "effective amount" refers to the amount of antigenic/immunogenic composition which, when administered to a human or animal, elicits an immune response. The effective amount is readily determined by one of skill in the art following routine procedures.

An "immune tolerant patient" as used herein refers to an animal or human patient which shows a limited ability to respond to antigens, particularly non-self antigens, but especially new antigens such as, for examples, new antigens present in newly emerging diseases. This limitation may be due, at least in part, to the chronological age of CD4+ T cells. Further, an "immune tolerant patient" may exhibit an impaired longterm CD4+ T-cell immune response to antigen exposure due to defects in the proliferation and cytokine secretion of memory T cells during recall responses.

A "T-cell activated patient" as used herein refers to an animal or human patient which exhibits T-cell activation and where a further stimulation of the T-cell response would cause a medical risk.

An "immunocompromised patient" as used herein refers to an animal or human patient having an immune system that has been impaired by age, disease such as HIV, or cancer, or by treatment such as, for example, treatment against inflammatory diseases including, but not limited to, Rheumatoid Arthritis, Psoriasis, Systemic Lupus Erythrematosis, Wegener's Granulamatosis, etc.

Within the scope of the present invention, it was demonstrated that the antibody induced response to the antigenic composition according to the invention is largely T-cell independent. A nude mouse model was used in this respect and nude mice were vaccinated and antibody responses measured to evaluate the Aβ-specific antibody response induced by the antigenic composition according to the invention in the immunized nude mice. The nude mice carry the Foxninu mutation and as a consequence, have reduced T-cell function due to the lack of a proper thymus.

A "pharmaceutically effective amount" as used herein refers to a dose of the active ingredient in a pharmaceutical composition adequate to cure, or at least partially arrest, the symptoms of the disease, disorder or condition to be treated or any complications associated therewith.

In a specific embodiment, the present invention makes use of an antigen presentation, particularly on the surface of a carrier molecule such as a liposome that results in enhanced exposure and stabilization of a preferred antigen conformation, which ultimately leads to a highly specific immune response, particularly a T-cell independent immune response, and results in the generation of antibodies with unique properties.

In particular, the antigenic peptide is presented on the surface of the carrier molecule in a highly repetitive array, particularly a repetitive array comprising at least 10 repetitive antigenic units/carrier molecule, particularly at least 50 repetitive antigenic units/carrier molecule, particularly at least 100 repetitive antigenic units/carrier molecule, particularly at least 200 repetitive antigenic units/carrier molecule, particularly at least 300 repetitive antigenic units/carrier molecule; particularly at least 400 repetitive antigenic units/carrier molecule, particularly at least 500 repetitive antigenic units/carrier molecule.

The modified phospho-peptide antigen according to the invention and as described herein, particularly a phospho-peptide antigen mimicking a major pathological phospho-epitope of protein tau, may be synthesized following a modified method reported in Nicolau et. al. (2002) Proc Natl. Acad. Sci. USA 99, 2332-2337. This approach involves stepwise assembling of the construct by solid phase peptide synthesis on an amide resin using standard Fmoc/tBu chemistry. The orthogonal protecting groups of the terminal lysines were then removed and the free amino groups acylated with palmitic acid.

Deprotection of the side-chain protecting groups and concomitant release of the peptide from the resin was achieved under acidic conditions, providing the desired tetrapalmytoylated phosphopeptide as a crude product.

The final product can then be obtained in high purity and its identity and purity confirmed by methods known in the art such as, for example, electrospray mass spectrometry and/or HPLC analysis.

In one embodiment, the present invention provides immunogenic compositions comprising a phospho-peptide antigen according to the invention and as described herein mimicking a major pathological phospho-epitope of protein tau, which peptide antigen is modified such that it is capable of maintaining and stabilizing a defined conformation of the antigen. This defined conformation leads to the induction of a strong and highly specific immune response upon introduction into an animal or a human.

One way of achieving the formation and stabilization of the desired conformation of the antigenic peptide is by presenting the antigenic peptide attached to, or incorporated or reconstituted, partially or fully, into a carrier, particularly a carrier that can also function as an adjuvant.

A carrier that may be contemplated within the scope of the present invention is, for example, a vesicle, a particulate body or molecule; bacterial membrane proteins, enterobacterial amp proteins, nanoparticles, micelles, gold particles, microbeads and/or virosomes or any other means that can suitably serve as a carrier/adjuvant for the antigenic peptide, but, particularly, a liposome.

In a specific embodiment of the invention, the antigenic peptide is attached to, or incorporated or reconstituted in the carrier through weak interactions such as, for example, van der Waal's, hydrophobic or electrostatic interaction, or a combination of two or more of said interactions, such that the peptide is presented with a specific conformation, which is maintained and stabilized by restricting said antigenic peptide in its three dimensional freedom of movement so that conformational changes are prevented or severely restricted.

When a vesicle, a particle or a particulate body is used as a carrier/adjuvant such as, for example, a liposome, the composition of the antigenic peptide may be chosen such that its overall net charge is identical to that of the carrier/adjuvant surface to which the peptide is attached. Electrostatic repulsion forces being effective between the identically charged carrier/adjuvant surface and the antigenic peptide, but particularly the identically charged carrier surface and the amino acid residues constituting the antigenic peptide and more particularly the identically charged carrier surface and the identically charged amino acid residues comprised in the antigenic peptide, may lead to the antigenic peptide taking on a defined, highly specific and stabilized conformation which guarantees a high biological activity. As a result, the antigenic peptide is exposed and presented in a conformation that is highly biologically active in that it allows the immune system of the target organism to freely interact with the antigenic determinants contained in the antigenic construct in the biologically active conformation, which, upon administration to an animal or a human, leads to a strong and conformation-specific immune response, resulting in, for example, a high antibody titer in the target organism.

The immunogenic response may be further increased by using a liposome as a carrier, which liposome may function as an adjuvant to increase or stimulate the immune response within the target animal or human to be treated with the pharmaceutical composition according to the invention. Optionally, the liposome may, in addition, contain a further adjuvant such as, for example, lipid A, alum, calcium phosphate, interleukin 1, and/or microcapsules of polysaccharides and proteins, but particularly a detoxified lipid A, such as monophoshoiyi or diphosphoryl lipid A, or alum.

In a specific embodiment of the invention, an antigenic peptide according to the invention and described herein, particularly an antigenic peptide the overall net charge of which is negative, is used reconstituted in a liposome, particularly a liposome the constituents of which are chosen such that the net overall charge of the liposome head group is negative. In particular, the liposome is composed of constituents selected from the group consisting of dimyristoyl phosphatidyl choline (DMPC), dimyristoyl phosphatidyl ethanolamine (DMPEA), dimyristoyl phosphatidyl glycerol (DMPG) and cholesterol and, optionally, further contains monophosphoryl lipid A or any other adjuvant that can be suitably used within the scope of the present invention such as, for example, alum, calcium phosphate, interleukin 1, and/or microcapsules of polysaccharides and proteins.

In another specific embodiment of the invention a modified peptide antigen according to the invention and as described herein before is provided covalently bound to an anchor-type molecule which is capable of inserting into the carrier/adjuvant thereby fixing the peptide to the carrier/adjuvant and presenting it on or in close proximity to the surface of a carrier/adjuvant molecule such that electrostatic forces can become effective as described herein before.

When liposomes are used as a carrier/adjuvant, the antigenic peptide construct generally has a hydrophobic tail that inserts into the liposome membrane as it is formed. Additionally, antigenic peptides can be modified to contain a hydrophobic tail so that it can be inserted into the liposome.

The antigenic composition of the present invention particularly comprises peptides modified to enhance antigenic effect wherein such peptides may be modified via pegylation (using polyethylene glycol or modified polyethylene glycol), or modified via other methods such by palmitic acid as described herein before, poly-amino acids (eg poly-glycine, poly-histidine), poly-saccharides (eg polygalacturonic acid, polylactic acid, polyglycolide, chitin, chitosan), synthetic polymers (polyamides, polyurethanes, polyesters) or co-polymers (eg. poly(methacrylic acid) and N-(2-hydroxy) propyl methacrylamide) and the like.

In a specific embodiment of the invention, antigenic peptides according to the invention and as described herein before are provided, which are modified to contain a hydrophobic tail so that said peptides can be inserted into the liposome. In particular, the phospho-peptide antigen according to the invention and as described herein mimicking a major pathological phospho-epitope of protein tau, may be modified by a lipophilic or hydrophobic moiety that facilitates insertion into the lipid bilayer of the carrier/adjuvant. The lipophilic or hydrophobic moieties of the present invention may be fatty acids, triglycerides and phospholipids, particularly fatty acids, triglycerides and phospholipids, wherein the fatty acid carbon back bone has at least 10 carbon atoms particularly lipophilic moieties having fatty acids with a carbon backbone of at least approximately 14 carbon atoms and up to approximately 24 carbon atoms, with each individual number of carbon atoms falling within this range also being part of the present invention. In particular, the invention relates to an antigenic peptide according to the invention and as described herein before, which is modified to contain a hydrophobic tail, particularly a hydrophobic tail comprising hydrophobic moieties having a carbon backbone of at least 14 carbon atoms, but especially 16 carbon atoms. Examples of hydrophobic moieties include, but are not limited to, palmitic acid, stearic acid, myristic acid, lauric acid, oleic acid, linoleic acid, linolenic acid and cholesterol or 1,2-distearoyl-sn-glycero-3-phosphatidylethanolamine (DSPE). In a specific embodiment of the invention the hydrophobic moiety is palmitic acid.

In one embodiment, the antigenic peptide according to the invention and as described herein, is covalently attached to the lipophilic or hydrophobic moiety. In the context of the present invention, the covalent attachment of the antigenic peptide may be mediated by means of amino acid residues, which extend the amino acid sequences corresponding to the sequences of the antigenic peptide according to the invention, in particular at their end(s), particularly at their N- and C-terminal end(s), and to which the fatty acid residues are coupled.

In particular, each conjugate comprises at least four molecules of fatty acid containing a carbon chain of between C12 and C24, particularly a carbon chain of C16, wherein the fatty acid molecules are covalently attached at the N- and C-terminal ends of the antigenic peptides. Other distributions may also be envisioned, including within the amino acid sequence. These peptides are also coupled covalently to the fatty acid molecules.

The pharmaceutical compositions of the present invention may thus comprise liposomes made by reconstituting liposomes in the presence of purified or partially purified or modified antigenic peptides according to the invention and as described herein. Additionally, peptide fragments may be reconstituted into liposomes. The present invention also includes antigenic peptide fragments modified so as to increase their antigenicity. For example, antigenic moieties and adjuvants may be attached to or admixed with the peptide. Examples of antigenic moieties and adjuvants include, but are not limited to, lipophilic muramyl dipeptide derivatives, non-ionic block polymers, aluminum hydroxide or aluminum phosphate adjuvant, and mixtures thereof.

Liposomes that can be used in the compositions of the present invention include those known to one skilled in the art. Any of the standard lipids useful for making liposomes may be used. Standard bilayer and multi-layer liposomes may be used to make compositions of the present invention. While any method of making liposomes known to one skilled in the art may be used, the most preferred liposomes are made according to the method of Alving et al., *Infect. Immun*, 60:2438-2444, 1992, hereby incorporated by reference. The liposome can optionally contain an adjuvant or and immunomodulator or both. A preferred immunomodulator is lipid A, particularly a detoxified lipid A such as, for example, monophosphoryl or diphosphoryl lipid A.

Liposomes may be prepared by the crossflow injection technique as described, for example, in Wagner et al (2002) Journal of Liposome Research Vol 12(3), pp 259-270. During the injection of lipid solutions into an aqueous buffer system, lipids tend to form "precipitates", followed by self arrangement in vesicles. The obtained vesicle size depends on factors such as lipid concentration, stirring rate, injection rate, and the choice of lipids. The preparation system may consist of a crossflow injection module, vessels for the polar phase (e.g. a PBS buffer solution), an ethanol/lipid solution vessel and a pressure device, but particularly a nitrogen pressure device. While the aqueous or polar solution is pumped through the crossflow injection module the ethanol/lipid solution is injected into the polar phase with varying pressures applied.

In one embodiment, the modified antigenic peptide according to the invention and as described herein may thus be further modified by reconstitution into liposomes consisting of phospholipids and cholesterol (phosphatidylethanolamine, phosphatidyl glycerol, cholesterol in varied molar ratios. Other phospholipids can be used. Lipid A is used at a concentration of approximately 40 µg/pmole of phospholipids.

The liposome may have a dual function in that it can be used as a carrier comprising the supramolecular construct as described herein before and, at the same time, function as an adjuvant to increase or stimulate the immune response within the target animal or human to be treated with the therapeutic vaccine according to the invention. Optionally, the liposome may, in addition, contain a further adjuvant or and immunomodulator or both such as, for example, lipid A, alum, calcium phosphate, interleukin 1, and/or microcapsules of polysaccharides and proteins, but particularly a lipid A, more particularly a detoxified lipid A, such as monophosphoryl or diphosphoryl lipid A, or alum.

In a specific embodiment of the invention liposomes with lipid A are used as adjuvant to prepare the pharmaceutical composition of the invention. Dimyristoyiphosphatidyl-choline, -glycerol and -cholesterol are mixed, particularly in a molar ratio of 9:1:7. A strong immunmodulator such as, for example, monophosphoryl lipid A is then added at a suitable concentration, particularly at a concentration of between 20 mg and 50 mg per mmol, more particularly at a concentration of between 30 mg and 40 mg per mmol of phospholipids. The modified antigenic peptide is then added at a molar ratio peptide to phospholipids of between 1:30 and 1:200, particularly at a molar ratio of between 1:50 and 1:120, more particularly of 1:100. Solvents are removed, for example through evaporation, and the resulting film hydrated with sterile buffer solution such as, for example PBS.

In a specific embodiment of the invention an antigenic peptide according to the invention and as described herein is provided modified by at least two molecules of palmitic acid covalently bound to the N- and C-terminal ends of said antigenic peptide and by reconstitution into a liposomal carrier.

Palmitoylation, while providing an anchor for the peptide in the liposome bilayer, due to the relative reduced length of the $C_{16:0}$ fatty acid moiety leads to the peptide being presented exposed on or in close proximity to the liposome surface.

The pharmaceutical composition of the present invention comprising a peptide antigen according to the invention and as described herein, particularly a phospho-peptide mimicking major pathological phospho-epitopes of protein tau, particularly in a pharmaceutically effective amount, may be prepared in the form of a liquid solution, or of an injectable suspension, or else in a solid form suitable for solubilization prior to injection in the context of, for example, a kit for making use of the present composition, as described below.

Suitable pharmaceutical carriers, diluents and/or excipients are well known in the art and include, for example, phosphate buffered saline solutions, water, emulsions such as oil/water emulsions, various types of wetting agents, sterile solutions, etc.

Formulation of the pharmaceutical composition according to the invention can be accomplished according to standard methodology know to those skilled in the art.

The pharmaceutical composition of the present invention comprising a peptide antigen according to the invention and as described herein, particularly a phospho-peptide mimicking major pathological phospho-epitopes of protein tau, particularly in a pharmaceutically effective amount, may be administered to a human or animal suffering from a tauopathy, or the symptoms associated with a tauopathy, to induce an immune response in said human or animal to alleviate symptoms associated with the disease or to restore a condition found in healthy individuals which are unaffected by the disease.

The compositions of the present invention are administered to a human or animal by any appropriate standard routes of administration in form of a solid, liquid or aerosol at a suitable, pharmaceutically effective dose. In general, the composition may be administered by topical, oral, rectal, nasal or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

In a specific embodiment of the invention the antigenic construct according to the invention, particularly a vaccine composition comprising said antigenic construct in a pharmaceutically acceptable form, is administered in repeated doses, in particular in 1 to 15 doses, more particularly in 2 to 10 doses, more particularly in 3 to 5 doses and even more particularly in 3 doses, in time intervals of between 1 week and 20 weeks, particularly in time intervals of between 1 and 10 weeks, particularly in time intervals of between 1 and 6 weeks, more particularly in time intervals of between 1 and 4 weeks, and even more particularly in time intervals of between 2 and 3 weeks. The immune response may be monitored by taking sera/plasma samples at a suitable time after boosting, particularly 3 to 10 days after boosting, more particularly 4 to 8 days after boosting and more particularly 7 days after boosting and determining the immunogenicity of the antigenic construct using known methodology, particularly one of the commonly used immunoassays such as, for example, an ELISA assay.

In particular, the antigenic peptide composition according to the invention is administered by parenteral, particularly by intra-peritoneal, intravenous, subcutaneous and intra-muscular injection.

Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The dosage of the composition will depend on the condition being treated, the particular composition used, and other clinical factors such as weight, size and condition of the patient, body surface area, the particular compound or composition to be administered, other drugs being administered concurrently, and the route of administration.

The pharmaceutical composition according to the invention may be administered in combination with other biologically active substances and procedures for the treatment of diseases, particularly neurodegenerative diseases. The other biologically active substances may be part of the same composition already comprising the pharmaceutical composition according to the invention, in form of a mixture, wherein the pharmaceutical composition of the invention and the other biologically active substance are intermixed in or with the same pharmaceutically acceptable solvent and/or carrier or may be provided separately as part of a separate composition, which may be offered separately or together in form of a kit of parts.

The pharmaceutical composition according to the invention may be administered concomitantly with the other biologically active substance or substances, intermittently or sequentially. For example, the pharmaceutical composition according to the invention may be administered simultaneously with a first additional biologically active substance or sequentially after or before administration of the pharmaceutical composition. If an application scheme is chosen where more than one additional biologically active substance are administered together with the at least one pharmaceutical composition according to the invention, the compounds or substances may partially be administered simultaneously, partially sequentially in various combinations.

It is another object of the present invention to provide for mixtures of a pharmaceutical composition according to the invention and, optionally, one or more further biologically active substances, as well as to methods of using a pharmaceutical composition according to the invention, or mixtures thereof including compositions comprising said pharmaceutical composition or mixtures of pharmaceutical composition for the prevention and/or therapeutic treatment and/or alleviation of the effects of tauopathies, a group of diseases and disorders associated with the formation of neurofibrillary lesions, the predominant brain pathology in this group of neurodegenerative disorders including, but not limited to, Alzheimer Disease, Creutzfeldt-Jacob disease, Dementia pugilistica, Down's Syndrome, Gerstmann-Sträussler-Scheinker disease, inclusion-body myositis, and prion protein cerebral amyloid angiopathy, traumatic brain injury and further amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease, type C, Pick's disease, progressive subcortical gliosis, progressive supranuclear palsy, Subacute sclerosing panencephalitis, Tangle only dementia, Postencephalitic Parkinsonism, Myotonic dystrophy.

The mixtures according to the invention may comprise, in addition to a pharmaceutical composition according to the invention, a biologically active substance such as, for example, known compounds used in the medication of tauopathies and/or of amyloidoses, a group of diseases and disorders associated with amyloid or amyloid-like protein such as the amyloid β protein involved in Alzheimer's Disease.

In another embodiment of the invention, the other biologically active substance or compound may also be a therapeutic agent that may be used in the treatment of diseases and disorders which are caused by or associated with amyloid or amyloid-like proteins including amyloidosis caused by amyloid β or may be used in the medication of other neurological disorders.

The other biologically active substance or compound may exert its biological effect by the same or a similar mechanism as the therapeutic vaccine according to the invention or by an unrelated mechanism of action or by a multiplicity of related and/or unrelated mechanisms of action.

Generally, the other biologically active compound may include neutron-transmission enhancers, psychotherapeutic drugs, acetylcholine esterase inhibitors, calcium-channel blockers, biogenic amines, benzodiazepine tranquillizers, acetylcholine synthesis, storage or release enhancers, acetylcholine postsynaptic receptor agonists, monoamine oxidase-A or -B inhibitors, N-methyl-D-aspartate glutamate receptor antagonists, non-steroidal anti-inflammatory drugs, antioxidants, and serotonergic receptor antagonists.

In particular, the mixture according to the invention may comprise at least one other biologically active compound selected from the group consisting of compounds against oxidative stress, anti-apoptotic compounds, metal chelators, inhibitors of DNA repair such as pirenzepin and metabolites, 3-amino-1-propanesulfonic acid (3APS), 1,3-propanedisulfonate (1,3PDS), secretase activators, β- and γ-secretase inhibitors, tau proteins, neurotransmitter, β-sheet breakers, anti-inflammatory molecules, or cholinesterase inhibitors (ChEIs) such as tacrine, rivastigmine, donepezil, and/or galantamine and other drugs and nutritive supplements, together with an therapeutic vaccine according to the invention and, optionally, a pharmaceutically acceptable carrier and/or a diluent and/or an excipient.

In a further embodiment, the mixtures according to the invention may comprise niacin or memantine together with a therapeutic vaccine according to the invention and, optionally, a pharmaceutically acceptable carrier and/or a diluent and/or an excipient.

In still another embodiment of the invention mixtures are provided that comprise "atypical antipsychotics" such as, for example clozapine, ziprasidone, risperidone, aripiprazole or olanzapine for the treatment of positive and negative psychotic symptoms including hallucinations, delusions, thought disorders (manifested by marked incoherence, derailment, tangentiality), and bizarre or disorganized behavior, as well as anhedonia, flattened affect, apathy, and social withdrawal, together with an therapeutic vaccine according to the invention and, optionally, a pharmaceutically acceptable carrier and/or a diluent and/or an excipient.

In a specific embodiment of the invention, the compositions and mixtures according to the invention and as described herein before comprise the pharmaceutical composition according to the invention and the biologically active substance, respectively, in a therapeutically or prophylactically effective amount.

Other compounds that can be suitably used in mixtures in combination with the pharmaceutical composition according to the invention are described, for example, in WO 2004/058258 (see especially pages 16 and 17) including therapeutic drug targets (page 36-39), alkanesulfonic acids and alkanolsulfuric acid (pages 39-51), cholinesterase inhibitors (pages 51-56), NMDA receptor antagonists (pages 56-58), estrogens (pages 58-59), non-steroidal anti-inflammatory drugs (pages 60-61), antioxidants (pages 61-62), peroxisome proliferators-activated receptors (PPAR) agonists (pages 63-67), cholesterol-lowering agents (pages 68-75); amyloid inhibitors (pages 75-77), amyloid formation inhibitors (pages 77-78), metal chelators (pages 78-79), anti-psychotics and anti-depressants (pages 80-82), nutritional supplements (pages 83-89) and compounds increasing the availability of biologically active substances in the brain (see pages 89-93) and prodrugs (pages 93 and 94), which document is incorporated herein by reference, but especially the compounds mentioned on the pages indicated above.

EXAMPLES

Example 1

Vaccines

Eight sequences derived from the phospho-tau protein were designed as antigen for vaccine development. A previously used immunogenic peptide was used as a control (Asuni et al., 2007).

TABLE 1

Tau sequence description

| DESCRIPTION | VACCINE | SEQUENCE |
| --- | --- | --- |
| T5: Control sequence: Tau 379-408 [pS396, pS404] | ACI-37 | RENAKAKTDHGAEIVYKS(p)PVVSGDTS(p)PRHL (n = 30) (SEQ ID NO: 1) |
| T1: Sequence 1: Tau 5-20 [pY18] | ACI-33 | RQEFEVMEDHAGTY(p)GL (n = 16) (SEQ ID NO: 2) |
| T8: Sequence 8: Tau 206-221 [pT212, pS214] | ACI-39 | PGSRSRT(p)PS(p)LPTPPTR (n = 16) (SEQ ID NO: 3) |
| T9: Sequence 9: Tau 196-211 [pS202, pT205] | ACI-40 | GYSSPGS(p)PGT(p)PGSRSR (n = 16) (SEQ ID NO: 4) |
| T3: Sequence 3: Tau 393-408 [pS396, pS404] | ACI-35 | VYKS(p)PVVSGDTS(p)PRHL (n = 16) (SEQ ID NO: 5) |
| T4: Sequence 4: Tau 401-418 [pS404, pS409] | ACI-36 | GDTS(p)PRHLS(p)NVSSTGSID (n = 18) (SEQ ID NO: 6) |
| T2: Sequence 2: Tau 200-216 [pS202 + pT205 & pT212 + pS214] | ACI-34 | PGS(p)PGT(p)PGSRSRT(p)PS(p)LP (n = 17) (SEQ ID NO: 7) |
| T10: Sequence 10: Tau 407-418 [pS409] | ACI-42 | HLS(p)NVSSTGSID (n = 12) (SEQ ID NO: 8) |
| T11: Sequence 11: Tau 399-408 [pS404] | ACI-43 | VSGDTS(p)PRHL (n = 10) (SEQ ID NO: 9) |

Example 2

Preparation of the Tau-Derived Tetrapairnvtoylated Phospho-Peptides

The antigenic peptide sequence flanked by the 2 pairs of Lysines was assembled stepwise by solid phase peptide synthesis on an amide resin using standard Fmoc/tBu chemistry. The orthogonal protecting groups of the terminal lysines were then selectively removed and the free amino groups acylated with palmitic acid. Deprotection of the side-chain protecting groups and concomitant release of the peptide from the resin was achieved under acidic conditions, providing the desired tetrapalmytoylated phosphopeptide as a crude product. The identity and purity was further confirmed by MALDI-TOF mass spectrometry and HPLC analysis.

```
Sequences of the Tau-derived tetrapalmytoylated
phosphopeptides:
T1: H-K(Pal)-K(Pal)-RQEFEVMEDHAGTY(P)GL-K(Pal)-
K(Pal)-NH2

T2: H-K(Pal)-K(Pal)-PGS(p)PGT(p)PGSRSRT(p)PS(p)LP-
K(Pal)-K(Pal)-NH2

T3: H-K(Pal)-K(Pal)-VYKS(p)PVVSGDTS(p)PRHL-K(Pal)-
K(Pal)-NH2

T4: H-K(Pal)-K(Pal)-GDTS(p)PRHLS(p)NVSSTGSID-
K(Pal)-K(Pal)-NH2

T8: H-K(Pal)-K(Pal)-PGSRSRT(p)PS(p)LPTPPTR-K(Pal)-
K(Pal)-NH2

T9: H-K(Pal)-K(Pal)-GYSSPGS(p)PGT(p)PGSRSR-K(Pal)-
K(Pal)-NH2

T10: H-K(Pal)-K(Pal)-HLS(p)NVSSTGSID-K(Pal)-
K(Pal)-NH2
```

-continued

```
T11: H-K(Pal)-K(Pal)-VSGDTS(p)PRHL-K(Pal)-K(Pal)-
NH2
```

2.1: Synthesis of Peptide Antigen T1

The orthogonally protected amino acid Fmoc-Lys(Mtt)-OH (3 eq) was manually loaded to an amide resin (Rink amide MBHA resin, 1 eq, 0.26 mmol) in the presence of 2 eq of DIC/HOBt in DMF. The resin was then washed with DMF (3×1 min). After removing the N-terminal Fmoc group with 25% piperidine in DMF (1×1 min and 2×15 min), the second residue of Fmoc-Lys(Mtt)-OH (3 eq), was automatically coupled using 5 eq of PyBOP/HOBt/DIEA in DMF (2×15 min), The following 16 amino acids bearing the Fmoc standard side-chain protecting groups were automatically incorporated applying the previously described coupling protocol.

The phosphoamino acids were introduced as monobenzyl esters at the phosphate group. Each coupling step was followed by a wash step with DMF (3×30 s), Fmoc removal step with 25% piperidine in DMF (3×3 min) and a second wash step with DMF (6×30 s), After the coupling of the Tyr(PO(OBzl)2), 0.5% DBU in DMF was used for the Fmoc-deprotection step. The assembly of the peptide sequence finished with the addition of the last two Fmoc-Lys(Mtt)-OH using 2 eq of PyBOP/HOBt/D1EA in DMF.

Then, the Mtt groups of the terminal lysine residues were selectively cleaved under nitrogen by treatment of the resin (1 eq, 600 mg, 0.092 mmol) with 10 mL of a degassed mixture of TIPS/TFA/DCM (1:1:98) during several cycles of 10 min. The resin was washed with DCM (×3) and DMF (×3). Then Palmitic acid (20 eq, 473 mg, 1.85 mmol) was coupled to these deprotected amino groups using TBTU (20 eq, 593 mg, 1.85 mmol) and DIEA (40 eq, 643 µL, 3.70 mmol) in DCM/DMF (1:1) (6 mL). The resin was washed with DCM (×5) and DMF (×5). Then the N-terminal Fmoc group was removed with degassed 20% piperidine in DMF (3×10 min) and the resin was washed with DMF (×3) and DCM (×5). Finally simultaneous resin cleavage and side-chain deprotections were carried out under nitrogen with a degassed mixture of TFA/TIPS/$H_2O$/EDT (95:1:2.5:2.5) (4 mL) during 4.5 h. Trituration from cold diethyl ether gave the crude product T1 as a white solid (189 mg, 60% yield) with a purity of 56% (from HPLC analysis), MALDI-TOF mass spectrometry confirmed the identity of the major product (m/z expected: 3427.12 [MH+], found: 3426.87).

2.2: Synthesis of Peptide Antigen T3

The orthogonally protected amino acid Fmoc-Lys(Mtt)-OH (3 eq) was manually loaded to an amide resin (Rink amide MBHA resin, 1 eq, 0.4 mmol) in the presence of PyBOP/HOBt/DIEA in DMF. The resin was then washed with DMF (3×1 min). After removing the N-terminal Fmoc group with 25% piperidine in DMF (1×1 min and 2×15 min), the second residue of Fmoc-Lys(Mtt)-OH (3 eq), was coupled using the same loading conditions. The following 16 amino acids bearing the Fmoc standard side-chain protecting groups were manually incorporated applying the previously described coupling protocol. The phosphoamino acids were introduced as monobenzyl esters at the phosphate group. The coupling time was determined by TNBT test or chloranyl test after a Proline. If necessary, a second coupling was performed with 2 eq of Fmoc-amino acid in the presence of DIC/HOBt or HATU/DIEA. Each coupling step was followed by a wash step with DMF (3×1 min), Fmoc removal step with 25% piperidine in DMF (1×1 min and 2×15 min) and a second wash step with DMF (7×1 min). After the coupling of the first Ser(PO(OBzl)OH), 0.5% DBU in DMF was used for the Fmoc-deprotection step. The assembly of the peptide sequence finished with the addition of the last two Fmoc-Lys(Mtt)-OH.

Then, the Mtt groups of the terminal lysine residues were selectively cleaved by treatment of the resin (1 eq, 195 mg, 0.01 mmol) with 10 mL of TIPS/TFA/DCM (1:1:98) during several cycles of 10 min. The resin was washed with DCM (×3) and DMF (×3). Then Palmitic acid (20 eq, 51 mg, 0.2 mmol) was coupled to these deprotected amino groups using TBTU (20 eq, 64 mg, 0.2 mmol) and DIEA (40 eq, 70 µL, 0.4 mmol) in DCM/DMF (1:1) (2 mL). The resin was washed with DCM (×5) and DMF (×5). Then the N-terminal Fmoc group was removed with 20% piperidine in DMF (3×10 min) and the resin was washed with DMF (×3) and DCM (×5). Finally simultaneous resin cleavage and side-chain deprotections were carried out using a mixture of TFA/TIPS/$H_2O$ (95:2.5:2.5) (2 mL) during 2 h. Trituration from cold diethyl ether gave the crude product T3 as a white solid (34 mg, 100% yield) with a purity of 67% (from HPLC analysis). MALDI-TOF mass spectrometry confirmed the identity of the major product (m/z expected: 3365.15 [MH+], found: 3369.66).

2.3: Synthesis of Peptide Antigen T4

The orthogonally protected amino acid Fmoc-Lys(Mtt)-OH (5-fold excess) was automatically attached to the Tentagel R RAM amide resin (0.19 mm/g, 750 mg, 0.1425 mmol) using DCCI and HOBt as activating agents in DMF. After removing the N-terminal Fmoc group, a second residue of Fmoc-Lys(Mtt)-OH (5-fold excess) was coupled in the presence DCCI and HOBt. The following 16 amino acids bearing standard side-chain protecting groups were automatically incorporated applying similar coupling/deprotection protocols. The phosphoamino acids were introduced as monobenzyl esters at the phosphate group. Double couplings of 60 min were performed for all the residues followed by a capping step with acetic anhydride. The assembly of the peptide sequence finished with the addition of the last two Fmoc-Lys (Mtt)-OH.

Then, the Mtt groups of the terminal lysine residues were selectively cleaved by treatment of the resin (1 eq, 750 mg, 0.075 mmol) with 10 mL of TIPS/TFA/DCM (1:1:98) during several cycles of 10 min. The resin was washed with DCM (×3) and DMF (×3). Then, Palmitic acid (20 eq, 51 mg, 0.2 mmol) was coupled to these deprotected amino groups using TBTU (20 eq, 482 mg, 1.5 mmol) and DIEA (40 eq, 536 µL, 3.0 mmol) in DCM/DMF (1:1) (7 mL). The resin was washed with DCM (×5) and DMF (×5). Then the N-terminal Fmoc group was removed with 20% piperidine in DMF (3×10 min) and the resin was washed with DMF (×3) and DCM (×5). Finally simultaneous resin cleavage and side-chain deprotections were carried out using a mixture of TFA/TIPS/$H_2O$ (95:2.5:2.5) (6 mL) during 3.5 h. Trituration from cold diethyl ether gave the crude product T4 as a white solid (96 mg, 37% yield) with a purity of 50% (from HPLC analysis). MALDI-TOF mass spectrometry confirmed the identity of the major product (m/z expected: 3455.10 [MH+], found: 3456.13).

2.4: Synthesis of Peptide Antigen T8

The orthogonally protected amino acid Fmoc-Lys(Mtt)-OH (5 eq, 781 mg, 1.25 mmol) was manually attached to Rink amide PEGA resin (1 eq, 0.33 mmol/g, 758 g) using DIPCDI (5 eq, 196 mL, 1.25 mmol) and HOBt (5 eq, 169 mg, 1.25 mmol) in DMF (5 mL) for two couplings of 8 h. The resin was then washed with DMF (×5). After removing the N-terminal Fmoc group with 20% piperidine in DMF (7 mL×3×5 min), a second residue of Fmoc-Lys(Mtt)-OH (10 eq, 1.56 g, 2.5 mmol) was coupled in the presence of TBTU (10 eq, 803 mg, 2.5 mmol), HOBt (10 eq, 338 mg, 2.5 mmol) and DIEA (20 eq, 871 mL, 5.0 mmol). The following 16 amino acids bearing standard side-chain protecting groups were manually incorporated through similar coupling/deprotection/wash cycles. Exceptionally, the phosphoamino acids were introduced as monobenzyl esters at the phosphate group (10 eq) with TBTU (10 eq), HOBt (5 eq) and DIEA (15 eq) in DMF. A coupling time of 1 h was used throughout the synthesis. The assembly of the peptide sequence finished with the addition of the last two Fmoc-Lys(Mtt)-OH.

Then, the Mtt-groups of the terminal lysine residues were selectively cleaved by treatment of the peptidyl resin (1 eq, 385 mg, 0.019 mmol) with 10 mL of TIPS/TFA/DCM (1:1:98) during several cycles of 10 min. The resin was washed with DCM (×3) and DMF (×3). Then Palmitic acid (20 eq, 968 mg, 3.8 mmol) was coupled to these deprotected amino groups using TBTU (20 eq, 1.21 g, 3.8 mmol) and DIEA (40 eq, 1.31 mL, 7.6 mmol) in DCM/DMF (1:1) (4 mL). The resin was washed with DCM (×5) and DMF (×5). Then the N-terminal Fmoc group was removed with 20% piperidine in DMF (3×10 min) and the resin was washed with DMF (×3) and DCM (×5). Finally simultaneous resin cleavage and side-chain deprotections were carried out using a mixture of TFA/TIPS/H$_2$O (95:2.5:2.5) (4 mL) during 3.5 h. Trituration from cold diethyl ether gave the crude product T8 as a white solid (50.2 mg, 10% yield) with a purity of 55% (from HPLC analysis). MALDI-TOF mass spectrometry confirmed the identity of the major product (m/z expected: 3331.17 [MH+], found: 3335.19).

2.5: Synthesis of Peptide Antigen T9

The orthogonally protected amino acid Fmoc-Lys(Mtt)-OH (3 eq) was manually loaded to an amide resin (Rink amide MBHA resin, 1 eq, 0.4 mmol) in the presence of PyBOP/HOBt/DIEA in DMF. The resin was then washed with DMF (3×1 min). After removing the N-terminal Fmoc group with 25% piperidine in DMF (1×1 min and 2×15 min), the second residue of Fmoc-Lys(Mtt)-OH (3 eq), was coupled using the same loading conditions. The following 16 amino acids bearing the Fmoc standard side-chain protecting groups were incorporated applying the previously described coupling protocol. The phosphoaminoacicls were introduced as monobenzyl esters at the phosphate group. The coupling time was determined by TNBT test or chioranyl test after a Proline. If necessary, a second coupling was performed with 2 eq of Fmoc-amino acid in the presence of DIC/HOBt or HATU/DIEA. Each coupling step was followed by a wash step with DMF (3×1 min), Fmoc removal step with 25% piperidine in DMF (1×1 min and 2×15 min) and a second wash step with DMF (7×1 min). After the coupling of the Thr(PO(OBzl)OH), 0.5% DBU in DMF was used for the Fmoc-deprotection step. The assembly of the peptide sequence finished with the addition of the last two Fmoc-Lys(Mtt)-OH.

Then, the Mtt-groups of the terminal lysine residues were selectively cleaved by treatment of the resin (1 eq, 650 mg, 0.156 mmol) with 10 mL of TIPS/TFA/DCM (1:1:98) during several cycles of 10 min. After washing with DCM (×3) and DMF (×3), Palmitic acid (20 eq, 1.01 g, 3.15 mmol) was coupled to those deprotected amino groups using TBTU (20 eq, 814 mg, 3.15 mmol) and DEA (40 eq, 1.1 mL, 6.30 mmol) in DCM/DMF (1:1) (6 mL). The resin was washed thoroughly with DCM (×5) and DMF (×5). Then the N-terminal Fmoc group was removed with 20% piperidine in DMF (3×10 min) and the resin was washed again with DMF (×3) and DCM (×5). Finally simultaneous resin cleavage and side-chain deprotections were carried out using a mixture of TFA/TIPS/H$_2$O (95:2.5:2.5) (9 mL) during 3 h. Trituration from cold diethyl ether gave the crude product T9 as a white solid (291 mg, 59% yield) with a purity of 69% (from HPLC analysis). MALDI-TOF mass spectrometry confirmed the identity of the major product (m/z expected: 3172.98 [MH+], found: 3172.90).

2.6: Synthesis of Peptide Antigen T10

Tetrapalmitoylated peptide T10 was prepared following a similar protocol as for 19 (peptide synthesis scale; 0.25 mmol). In addition, a pseudo praline [psi(Gly-Ser)] was used as building block before the problematic sequence Asn-Val-Ser-Ser. The crude product T10 was obtained as a white solid (809 mg, quantitative yield) with a purity of 56% (from HPLC analysis). MALDI-TOF mass spectrometry confirmed the identity of the major product (m/z expected: 2761.9 [MH+], found: 2759.2).

2.7: Synthesis of Peptide Antigen T11

Tetrapalmitoylated peptide T11 was prepared following a similar protocol as for T9 (peptide synthesis scale: 0.25 mmol). The crude product T11 was obtained as a white solid (495 mg, 76% yield) with a purity of 80% (from HPLC analysis). MALDI-TOE mass spectrometry confirmed the identity of the major product (m/z expected: 2613.8 [MH+], found: 2612.2).

Example 3

Vaccine Preparation (Process A)

Tau-derived tetrapalmitoylated phosphopeptide was weighed (see table 2 below for quantity), and put into 250 ml glass round bottom flask. Then Dimyristoyl phosphatidylcholine (DMPC), Dimyristoyl phosphatidylglycerol (DMPG), Cholesterol and adjuvant Monophosphoryl Lipid A (MPLA) (all Avanti Polar Lipids Inc. AL, USA) were weighed and added at molar ratio of 9:1:7:0.2 respectively. Then Chloroform was added giving a clear solution with fine particles. After gently agitation during 15 min, the organic solvent was removed by evaporation under reduced pressure at 40° C. and then under high vacuum for 3 h. The resulting thin-film was rehydrated by addition of sterile PBS in a lamellar hood and gently agitated at RT for 18 h. The final peptide/phospholipid molar ratio was 1:100. The liposomal suspension was then aliquoted into sterile 15 ml falcon tubes (5 ml product/tube) prior to storage at 2-8° C. Final peptide concentration was 40 µM.

Example 4

Characterization of Tau Liposomal Vaccines 4.1. Methods
4.1.1 Peptide, DMPC and Cholesterol Quantification by HPLC For analysis of the liposomal tau vaccines (ACl-33, ACl-35, ACl-36, ACl-39, ACl-40 and ACl-41 all prepared according to the process A described in EXAMPLE 3), samples were prepared by adding water (20 µl) to the vaccine sample (20 µl) in a glass HPLC vial, followed by isopropanol (140 µl) and TEA (20 µl). The 5-fold diluted sample was briefly vortexed prior to injection (20 µl). Analysis was performed using a C3-reverse-phase Zorbax 300SB-B3 column (250×4.6 mm, 5 µm, 300 Å, Agilent) thermostated to 75° C., with detection at 207 and 214 nm. Eluent solvents were as follows: solvent B, 95% Isopropanol, 5% Water, 0.1% TEA; solvent A, 10% Acetonitrile, 90% Water, 0.1% TEA. A gradient from 40% B to 60% B was applied during 20 min with a flow rate of 1 ml/min. Standards of tau peptides (T1, T3, T4, T8 and T9) and DMPC/Cholesterol were used separately at different concentrations for calibration purposes. For tau peptides, a stock solution of 1 mg/ml in TFA/iPrOH/H$_2$O (1:7:2) was prepared and (1:1) serially diluted from 400 µg/ml to 12.5 µg/ml. For the lipids, a stock solutions of 8.0 mg/ml of DMPC and 3.5 mg/ml of Cholesterol in 70% isopropanol and 30% water and diluted (1:5), (1:10) and (1:50) with the same mixture.

4.1.2 MPLA Quantification by HPLC

MPLA within tau liposomal vaccine was quantified by HPLC with UV detection following derivatization of the adjuvant with the UV active chromophore 3,5-Dinitrobenzyloxyamine (DNBA). Briefly, 20 µl of liposomal tau constructs were added to a solution of DNBA in pyridine (10 mg/mil, total volume 100 µl), heated at 60° C. for 3 h and then the pyridine was removed by evaporation. The resulting pellet was resolubilized in chloroform/methanol (2:1, v/v) for HPLC analysis. MPLA (Avanti Polar Lipids) was used for calibration purposes at four different concentrations and was derivatized and analyzed as for the liposomal tau constructs. HPLC analysis was performed using an Agilent XDB-C18 reverse-phase column (250×4.6 mm, 120 Å, 5 µm), thermostated to 50° C., with detection at 254 nm. Eluent solvents were as follows: solvent A, 95% Acetonitrile, 5% Water, 4.8 mM phosphoric acid; solvent B, 95% Isopropanol, 5% Water, 4.8 mM phosphoric acid. A gradient from 10% B to 70% B was applied during 30 min with a flow rate of 1 ml/min.

4.1.3 Liposome Surface Potential

Tau liposomal construct samples were diluted 100-fold with PBS. Analysis was performed using a Zetasizer Nano (Malvern, USA) at 25° C. Measurement duration and voltage selection were performed in automatic mode, with a typical applied voltage of 50 mV. Data was transformed using the Smoluchowski equation automatically using DTS 5.0 (Malvern) software to calculate the zeta potential. As the tau liposomal constructs are composed of a mixture of DMPCID-MPG/Cholesterol/MPLA at molar ratio of 9:1:7:0.2; the expected net charge will be negative.

4.1.4 Conformational Analysis by Circular Dichroism

Tau liposomal constructs were diluted (1:1) with PBS to give a final peptide concentration of 18 µM. Liposomes with identical composition but lacking the tau peptide were used as the blank solution for baseline subtraction. CD spectra were acquired on a Jasco-815 spectropolarimeter with a 0.1 cm path length quarzt cuvette (Hellma, Germany) at 23° C. Measurements were made over a 195-250 nm wavelength range with a 1.0 nm bandwidth and 0.5 nm resolution. A scan speed of 50 nm/min with response time of 1 sec was employed. Blank spectra (from 8 scans) were averaged and substracted from the average of 8 scans of each sample spectra. The obtained spectrum ($[\theta]_{obs}$, degrees) was smoothed after being converted to mean residue molar ellipticity ($[\theta]$, degrees cm$^2$ dmol$^{-1}$) with the equation $[\theta]=[\theta]_{obs}\times(MRW/10lc)$, where MRW is the mean residue molecular weight (MW/number of residues), l is the optical path length (cm) and c is the concentration (g/cm$^3$).

4.1.5 ThT Fluorescence Assay

ThT fluorescence measurements were acquired on a microplate reader Infinite M200 (Tecan Group Ltd, Switzerland). As a general procedure, Tau liposomal constructs were diluted to different concentrations with PBS (Table 2). Liposomes of same composition but lacking tau peptide were diluted similarly to be used as negative control (batch ACl-35-081015-B). To 98 µl of each vaccine or blank solution, ThT (2 µl, 12 mM in water) was added to give a final concentration of 24 µM. After brief vortexing, an aliquot from each sample (70 µl) was added onto a black opaque 384-well Perkin Elmer microtiter plate and fluorescence emission was measured at 485 nm after 30 min upon excitation at 440 nm. The excitation bandwidth was 9 nm and the emission bandwidth 20 nm, γ-Cyclodextrin was used as an internal control. Serial 2-fold dilutions in PBS were made from a 640 mM stock solution in PBS to obtain 320, 160, and 80 mM γ-cyclodextrin control solutions.

TABLE 2

Samples prepared for ThT assay

| Peptide | Vaccine | Batch | Dilution | Conc. Peptide (µg/ml) |
|---|---|---|---|---|
| T1 | ACI-33 | ACI-33-081031-A | 2-fold | 23 |
| | | ACI-33-081031-A | 3-fold | 15 |
| | | ACI-33-081031-A | 4-fold | 7.7 |
| | | ACI-33-081031-A | 12-fold | 3.8 |
| T3 | ACI-35 | ACI-35-081015-A | 2-fold | 39 |
| | | ACI-35-081015-A | 3-fold | 26 |

TABLE 2-continued

Samples prepared for ThT assay

| Peptide | Vaccine | Batch | Dilution | Conc. Peptide (µg/ml) |
|---|---|---|---|---|
| | | ACI-35-081015-A | 4-fold | 20 |
| | | ACI-35-081015-A | 12-fold | 5 |
| T4 | ACI-36 | ACI-36-081110-A | 2-fold | 16.5 |
| | | ACI-36-081110-A | 3-fold | 11 |
| | | ACI-36-081110-A | 4-fold | 8.3 |
| | | ACI-36-081110-A | 12-fold | 2.1 |
| T8 | ACI-39 | ACI-39-090202-A | 2-fold | 24 |
| | | ACI-39-090202-A | 3-fold | 16 |
| | | ACI-39-090202-A | 4-fold | 12 |
| | | ACI-39-090202-A | 12-fold | 4 |
| T9 | ACI-40 | ACI-40-090202-A | 2-fold | 30 |
| | | ACI-40-090202-A | 3-fold | 20 |
| | | ACI-40-090202-A | 4-fold | 15 |
| | | ACI-40-090202-A | 12-fold | 5 |
| T8 + T9 | ACI-41 | ACI-41-081204-A | 2-fold | 11.5 |
| | | ACI-41-081204-A | 3-fold | 7.7 |
| | | ACI-41-081204-A | 4-fold | 5.8 |
| | | ACI-41-081204-A | 12-fold | 1.9 |
| Negative Control | Negative control | ACI-35-081015-B | 2-fold | n/a |
| | | ACI-35-081015-B | 3-fold | n/a |
| | | ACI-35-081015-B | 4-fold | n/a |
| | | ACI-35-081015-B | 12-fold | n/a |

4.2. Results 4.2.1 Peptide, DMPC and Cholesterol Quantification by HPLC

The HPLC chromatogram at the detection wavelength of 207 nm obtained from the injection of the vaccine samples showed the presence of the tau peptide, DMPC and cholesterol (see table 4). From the calibration curves determined with the standards, the quantity of each component in the vaccine was calculated. The detected tau peptide, DMPC and Cholesterol content in the tau liposomal suspensions was close to the target values.

4.2.2 MPLA Quantification by HPLC

The HPLC chromatogram at the detection wavelength of 254 nm obtained from the injection of the DNBA-derivatized tau vaccine sample showed the presence of labelled MPLA (see table 4). Using the calibration curve obtained with the standard, the quantity of MPLA in the tau liposomal vaccines was calculated. The detected MPLA content in the tau liposomal suspensions was close to the target values.

4.2.3 Liposome Surface Potential

The measured zeta potential of tau liposomal vaccines is shown in table 4.

4.2.4 Conformational Analysis of Tau Peptide within Liposomal Vaccines by CD

The conformation of tau liposomal vaccines prepared according to the description before was determined by circular dichroism. The results are shown in table 3.

4.2.5. ThT Assay of Tau Peptide within Liposomal Vaccines

The aggregated states of tau peptides of the liposomal vaccines (prepared by above-described process A) determined by ThT fluorimetric assay are shown in table 4.

TABLE 3

Summary of vaccine characteristics

| Vaccine | Component | Retention Time | Target value (µg/ml) | Result (µg/ml) | Liposome Surface Potential (mV) | Conformation Circular Dichroism | ThT assay (peptide aggregation) Fluorescence signal |
|---|---|---|---|---|---|---|---|
| ACI-33 | Peptide T1 | 19.3 min | 130 | 46 | −18.7 | beta-sheet and beta-turn mixed conformation | Aggregation |
| | Cholesterol | 11.2 min | 1027 | 923 | | | |
| | DMPC | 10.0 min | 2314 | 2463 | | | |
| | DMPG | Nd | 261 | nd | | | |
| | MPLA | 39.8 min | 135 | 62 | | | |
| ACI-35 | Peptide T3 | 19.5 min | 130 | 78 | −19.2 | random coil conformation | No aggregation |
| | Cholesterol | 11.6 min | 1046 | 1438 | | | |
| | DMPC | 10.3 min | 2357 | nd | | | |
| | DMPG | nd | 266 | nd | | | |
| | MPLA | 29.7 min | 135 | 124 | | | |
| ACI-36 | Peptide T4 | 20.3 min | 130 | 33 | −17.8 | random coil conformation with some beta-sheet contribution | Aggregation |
| | Cholesterol | 11.2 min | 1018 | 1387 | | | |
| | DMPC | 10.0 min | 2296 | nd | | | |
| | DMPG | nd | 259 | nd | | | |
| | MPLA | 29.7 min | 135 | 83 | | | |
| ACI-39 | Peptide T8 | 19.3 min | 130 | 48 | −16.8 | beta-sheet conformation | No aggregation |
| | Cholesterol | 11.8 min | 1056 | 1906 | | | |
| | DMPC | 10.5 min | 2381 | 4316 | | | |
| | DMPG | nd | 269 | nd | | | |
| | MPLA | 30.9 min | 135 | 144 | | | |
| ACI-40 | Peptide T9 | 21.0 min | 130 | 60 | −14.7 | random coil conformation | No aggregation |
| | Cholesterol | 11.8 min | 1109 | 1655 | | | |
| | DMPC | 10.5 min | 2500 | 2894 | | | |
| | DMPG | nd | 269 | nd | | | |
| | MPLA | 30.9 min | 135 | 122 | | | |
| ACI-41 | Peptide T8 + T9 | 18.3 min + 19.9 min | 65 + 65 | 23 + 34 | −17.3 | mixture of random coil and beta-sheet conformation | No aggregation |
| | Cholesterol | 11.2 min | 1109 | 34 | | | |
| | DMPC | 9.9 min | 2500 | 1574 | | | |
| | DMPG | nd | 282 | 3829 | | | |
| | MPLA | 30.9 min | 135 | 80 | | | |

Example 5

Immunogenicity of Tau Palmitoylated Antigens in Wild Type and Tau−/− KO Mice 5.1. Methods 5.1.1 Tau Knock-Out Mice (TKO)

Knocking out of the tau gene was achieved using a targeting vector which inserted the EGFP (Enhanced Green Fluorescent protein) cDNA in exon 1 of the gene in-frame with the endogenous initiation codon. This produced a fusion protein with the first 31aa of tau followed by EGFP (described by Tucker K L. et al., *Nature Neuroscience*, 2001). The deletion of the gene was confirmed by western blot of whole brains lysates. Tau protein levels using several anti-tau antibodies showed that all tau isoforms were absent in the homozygous mutant, with a 50% reduction in the heterozygous mutant. The mutation was maintained on C57BL/6 background.

5.1.2 Preparation of the Vaccine

Vaccines were prepared by process A described in EXAMPLE 3.

5.1.3 Immunizations

C57BL/6 or Tau−/− KO mice (TKO) received i.p. injections of the vaccine (ACI-33, ACI-35, ACI-36 and ACI-41) on three occasions (Scheme 1) (Table 4), For ACI-33, ACI-35. ACI-36 and ACI-41 immunization, the three immunizations were done with a 2 weeks interval between each administration (day (d)0, d13, d28) according to Scheme 1. 1 day (d-1) before the first immunizations then after the second (d27) and third (d47) immunizations blood samples were collected and sera prepared. Serum was prepared by letting the blood samples clot overnight then taking the supernatant after centrifugation. Tau phosphopeptide-specific IgG and IgM antibody titers and IgG isotype patterns were determined by ELISA. As control, non-pTau peptide-specific IgG antibody titers were also determined by ELISA.

TABLE 4

Mice Immunization

| Group | mice | Age months | Number of Animals and Gender | Treatment/ Volume[a] | Vaccine Batch | Route of Administation[b] | Dose level Quantity of peptide ug/dose[c] | Quantity of MPLA ug/dose[c] |
|---|---|---|---|---|---|---|---|---|
| ACI-33 (T1 peptide) | WT | 6 | 3 ♀ 3 ♂ | ACI-33 0.2 ml | ACI-33-081031-A | i.p. | 9 | 12 |
|  | KO | 4-5 | 3 ♀ 3 ♂ | ACI-33 0.2 ml | ACI-33-081031-A | i.p. | 9 | 12 |
| ACI-35 (T3 peptide) | WT | 6 | 3 ♀ 3 ♂ | ACI-35 0.2 ml | ACI-35-081015-A | i.p. | 16 | 23 |
|  | KO | 6-8 | 3 ♀ 3 ♂ | ACI-35 0.2 ml | ACI-35-081015-A | i.p. | 16 | 23 |
| ACI-36 (T4 peptide) | WT | 6 | 3 ♀ 3 ♂ | ACI-36 0.2 ml | ACI-36-081110-A | i.p. | 7 | 13 |
|  | KO | 4 | 3 ♀ 3 ♂ | ACI-36 0.2 ml | ACI-36-081110-A | i.p. | 7 | 13 |
| ACI-41 (T8 + T9 peptides) | WT | 7 | 3 ♀ 3 ♂ | ACI-41 0.2 ml | ACI-41-081204-A | i.p. | 5 | 7 |
|  | KO | 4 | 3 ♀ 3 ♂ | ACI-41 0.2 ml | ACI-41-081204-A | i.p. | 5 | 7 |

[a]theoretical volume
[b]i.p.: intra-peritoneal
[c]measured quantity determined after analysis 5.1.4 Quantification of Tau Peptide-Specific Antibodies Specific IgG antibodies for pTau peptides were determined by ELISA in the 3 sera bleeding samples. Tau peptides-specific IgG were determined in the sera from d-1 and d47. Peptides pTau-specific IgM and IgG isotype antibodies were determined by ELISA in the d47 sera bleeding sample. Plates were coated with 10 ug/ml of corresponding Tau peptide overnight at 4° C. After washing each well with PBS-0.05% Tween 20 and blocking with 1% BSA in PBS-0.05% Tween 20, serial dilutions of sera were added to the plates and incubated at 37° C. for 2 hours. After washing, plates were incubated with an alkaline phosphatase (AP)-conjugated anti-mouse IgG total antibody (Jackson Laboratories, Baltimore, Pa., USA) or isotype specific antibodies (horseradish Peroxidase (HRP)-conjugated anti-mouse IgM, AP-conjugated anti-mouse IgG1, biotin-conjugated anti-mouse IgG2a and IgG3, purchased from Pharmingen BD, San Diego, Calif., USA and HRP-conjugated anti-mouse IgG2b from Zymed Laboratories, San Francisco, Calif.) for 2 hours at 37° C. After washing, plates were incubated with pNPP (para-nitro-phenyl-phosphate), the phosphatase substrate for AP, or ABTS (2,2'-azino-bis(3-ethylbenzthiazoline-6-sulphonic acid)), the substrate for HRP and read at 405 nm using an ELISA plate reader. A supplemental step was done for the biotin conjugated antibodies where plates were incubated for 45 min in streptavidin-HRP(R&D Systems, Minneapolis, Minn., USA) before detection using ABTS. Results are expressed as O.D. (Optical Density) at the first dilution and a non saturated dilution for IgG and at a non-saturated O.D. for IgG isotypes and IgM.

5.1.5 Binding of Anti-Tau Antibodies to Tau Tangles on Brain Slices from Transgenic Animal (TAUPIR)

Binding of antibodies present in the serum of vaccinated animals to tangles on brain slices was done by TAUPIR immunohistochemistry.

Brain slices used were from Tau P301L (TPLH: longest isofrom (441aa) of human Tau with the P301L mutation) transgenic animal at a terminal stage and from old (>15 months) double transgenic biGT mice (GSK-3 transgenic mice cross with TPLH mice).

Brain sections were washed for 5 min in PBS then incubated for 15 min at RT in 1.5% $H_2O_2$ in PBS:MeOH (1:1) to block endogenous peroxidase. After washing the sections 3 times in PBST (PBS/0.1% Triton×100) they were incubated for 30 min at RT in PBST+10% FCS (fetal calf serum) blocking solution. The incubation with the serum containing the anti-Tau antibodies was done overnight at 4° C. Serum was diluted in PBST/10% FCS using several different dilutions from 1/2'500 to 1/10'000. Sections were washed 3 times in PBST before incubation with an HRP-conjugated goat anti-mouse (purchased from Dako, Glostrup, Denmark)) secondary antibody in PBST/10% FCS for 1 hour at RT. Prior to detection sections were washed 3 times with PBST and incubated in 50 mM Tris/HCl pH7.6 for 5 min, Detection was done using by incubating the sections for 3 min in Diaminobenzidine (DAB: 1 tablet in 10 ml of 50 mM Tris, HCl+3 ul $H_2O_2$ 30%) (MP Biomedicals, Solon, Ohio, USA). The reaction was stopped by washing the sections 3 times in PBST. The sections were then transferred onto silanized glass-plates and air-dry on warm-plate at 50° C. for 2 hours. A counterstaining was done using incubation with Mayers hematoxylin (Fluka Chemie, Buchs, Switzerland) for 1 min followed by a washing step for 4 min in running tap-water. Sections were dehydrated by passing in 50%, 70%, 90% and twice in 100% ethanol bath then in Xylol for 2 times 1 min. Finally sections were mounted with DePeX (BDH Chemicals Ltd., Poole, England) under glass cover-slips.

5.1.6 Western Blot (WB)

Binding of antibodies present in the serum of vaccinated animals to pTau in brain extract from transgenic animal was done by WB.

Brain homogenization of wild-type FVB, TPLH, biGT and Tau knock-out (TKO) mouse was done in the following buffer: 25 mM Tris/HCl pH7.6, 150 mM NaCl, 1 mM EDTA, 1 mM EGTA, 30 mM NaF, 0.2 mM $Na_3VO_4$, 1 nM Okadaic acid, 1 mM phenylmethylsulfonyl fluoride (PMSF), 5 mM Na4P2O7, 1 tablet complete protease inhibitor cocktail (CPIC) per 12 ml total. To obtain total brain homogenate the brain was homogenize on ice in 1 vol/weight hemisphere (ml/g) with a motor-driven potter-like (glass tube/teflon pestle) used at 700 rpm.

Total brain homogenate was diluted half in sample buffer (125 mM Tris/HCl. pH6.8, 4% (w/v) sodium dodecyl sulfate (SDS), 20% glycerol, 0.01% bromophenol blue)+5% beta-mercapto-ethanol then heat rapidly to 95° C. Samples were kept 5 min, diluted ¼ in sample buffer, heat again to 95° C. then cooled down and spin at 14000 rpm for 5 min to clear debris that were not solubilized. Supernatants were collected and loaded on a SDS-PAGE gel. The transfer to the nitrocellulose membrane (Hybond-ECL) was done in transfer buffer (25 mM iris pH 8.6, 190 mM Glycine, 20% methanol). Membrane was transferred to the blocking solution (0.1% Tween in TBS (50 mM Tris.HCl, pH7.6, 150 mM NaCl)+5% milkpowder) prior to overnight incubation at 4° C. with the mouse serum diluted in the blocking solution. Incubation with secondary antibody HRP-conjugated goat anti-mouse (Dako, Glostrup, Denmark) diluted 1/10'000 in blocking solution was performed at RT for 1 hour. Detection was done using the ECI Western Blotting Detection Reagents from GE Healthcare.

5.2. Results

5.2.1 Specificity of Antibody from Sera of Vaccinated Mice

Sera from vaccinated mice were tested for the specificity of their antibodies in ELISA assay against both pTau and Tau peptide, tau tangles in TAUPIR and pTau in western blot.

ACl-33 vaccine induced an anti-Tau5-20 [pY18] IgG response following i.p. injection. After 2 immunizations (d27), the IgG response remained stable with no increase with the third immunization (d47) (FIG. 1a: WT mice, 1-way Anova P<0.05 d-1 vs d27, P<0.001 d-1 vs d47 and FIG. 1b: TKO mice, 1-way Anova P<0.001 d-1 vs d27/47).

ACl-35 vaccine induced a robust anti-Tau393-408 [pS396/pS404] IgG response following i.p. injection. After 2 immunizations (d28), the IgG response remained stable (d42, 98 and 126) with no increase with the 3$^{rd}$ immunization (d42) and no decrease in bleedings before, in between and after boosting (FIG. 2a: WT mice:1-way Anova P<0.0001 d-1 vs d28/42/98/126 and FIG. 2b: TKO mice:1-way Anova P<0.0001 d-1 vs d28/42/98/126).).

ACl-36 vaccine induced a Tau401-418 [pS404/S409] IgG response following i.p. injection. After 2 immunizations (d27), the IgG response remained stable with no increase with the third immunization (d47) (FIG. 3a: WT mice: 1-way Anova P<0.001 d-1 vs d27, P<0.0001 d-1 vs d47 and (FIG. 3b: TKO mice: 1-way Anova P<0.0001 d-1 vs d27/47).

ACl-41 vaccine induced a robust IgG response following i.p. injection on both Tau206-221 [pT212/pS214] and Tau196-211 [pS202/pT205] peptides. After 2 immunizations (d34), the IgG response remained stable (d48) with no increase after third immunization (d48) (FIG. 4a: WT mice, anti-Tau206-221 [pT212/pS214]-IgG, 1-way Anova P<0.0001 d-1 vs d34/48) (FIG. 4b: WT mice, anti-Tau196-211 [pS202/pT205]-IgG, 1-way Anova P<0.0001 d-1 vs d34/48). (FIG. 4c: TKO mice, anti-Tau206-221 [pT212/pS214]-IgG, 1-way Anova P<0.0001 d-1 vs d34/48) (FIG. 4d, TKO mice, anti-Tau196-211 [pS202/pT205]-IgG, 1-way Anova P<0.0001 d-1 vs d34/48).

Sera from vaccinated mice were further tested for the specificity of the anti-tau antibodies in TAUPIR immunohistochemistry and western blot. The data from all liposomal constructs and for each mouse model are summarized in the table 5 below.

TABLE 5 synopsis of antibody specificity from sera of vaccinated mice

| Vaccine | mice | ELISA (positive/total mice) | TAUPIR (positive/total mice) | Western Blot (positive/total mice) |
|---|---|---|---|---|
| ACI-33 | WT | 4/6 | 2/6 | 1/6 |
|  | KO | 5/6 | 2/6 | 2/6 |
| ACI-35 | WT | 5/6; 1† | 5/6; 1† | 5/6; 1† |
|  | KO | 6/6 | 3/6 | 6/6 |
| ACI-36 | WT | 5/6 | 4/6 | 1/6 |
|  | KO | 5/6; 1† | 3/6; 1† | 1/6; 1† |
| ACI-41 | WT | 6/6 | 4/6 | 4/6 |
|  | KO | 6/6 | 1/6 | 3/6 |

5.2.2 Analysis of the Isotype Response from Wild-Type C57BL/6 and Tau−/− KO (TKO) Immunized Mice ACl-33

ACl-33 vaccine induced in WT mice antibody titers for all IgG2a, 2b and 3 isotypes as well as IgM following 3 i.p. immunizations (FIG. 5a; WT mice). There was almost no IgG1 and there is a significant difference between IgG1 and IgG2b and 3 (FIG. 5a; WT mice; 1-way Anova P<0.05 IgG1 vs IgG3, P<0.001 IgG1 vs IgG2b). ACl-33 vaccine induced in TKO mice antibody titers for all IgG2a, 2b and 3 isotypes as well as IgM following 3 i.p. immunizations (FIG. 5b; TKO mice). There was almost no IgG1 with a significant difference between this subclass and the other IgG isotypes (FIG. 5b, 1-way Anova P<0.05 IgG1 vs IgG2a/IgG3, P<C1.001 IgG1 vs IgG2b).

ACl-35

ACl-35 vaccine induced in WT mice high antibody titers for all IgG isotypes as well as IgM following 3 i.p. immunizations (FIG. 6a; WT mice). The only significant difference is a higher IgM response compared to IgG3 (FIG. 6a; WT mice, 1-way Anova P<0.05 IgM vs IgG3).

ACl-35 vaccine induced in TKO mice high antibody titers for all IgG isotypes as well as IgM following 3 i.p. immunizations (FIG. 6b; TKO mice).

ACl-36

ACl-36 vaccine induced in WT mice antibody titers for all IgG isotypes as well as IgM following 3 i.p. immunizations (FIG. 7a; WT mice).

ACl-36 vaccine induced in TKO mice antibody titers for all IgGs isotypes as well as IgM following 3 i.p. immunizations (FIG. 7b; TKO mice). There was a statistically significant higher level of IgG2b compared to IgG1 (FIG. 7b; TKO mice, 1-way Anova P<0.05 IgG2b vs IgG1), ACl-41

ACl-41 vaccine induced in WT mice high anti-Tau196-211 [pS202/pT205] antibody titers for all IgG isotypes as well as IgM following 3 i.p. immunizations (FIG. 8a; WT mice).

ACl-41 vaccine induced in TKO mice high anti-Tau196-211 [pS202/pT205] antibody titers for all IgG isotypes as well as IgM following 3 i.p. immunizations (FIG. 8b; TKO mice).

5.3. Conclusion

Tau vaccine induced IgG titers in all mice. There was a low IgG1 antibody response compared to IgG2b and IgG3 in ACI-33 immunized mice. In all other tau vaccinated mice, the induced antibody titers for all IgG2a, 2b and 3 isotypes as well as IgM were comparable.

Antibodies generated from tau vaccine immunized mice specifically bind pTau with marginal binding to Tau peptides. The generated antibodies were as well able to recognize tangles in Tau transgenic mouse brain and pTau from Tau transgenic mouse brain extract by WB Example 6

Generation and Screening of Hybridomas and Antibodies

The objective of this study was to generate and screen anti-Tau mAbs (monoclonal antibodies). Hybridomas were generated by fusion of tau vaccine immunized mouse spleen with a myeloma cell line. The hybridomas were assessed for reactivity against both phosphorylated and non-phosphorylated full-length Tau protein, as well as the phosphorylated and non-phosphorylated Tau antigenic peptides used in the vaccine preparation. Hybridoma screening was also performed for reactivity of hybridomas supernatant for tau tangles using immunochemistry on Tau transgenic mouse brain slices.

6.1. Methods 6.1.1 Fusion

A wild type C57BL/6 mouse vaccinated with ACI-33 (Tau5-20 [pY18]) and ACI-35 was used for hybridoma production. The mouse was boosted with ACI-33 vaccine on day 0 then again on day 4 and the fusion was performed on day 7. $173 \times 10^5$ (ACI-33), splenocytes from the immunized mouse were fused with SP2-O—Ag14 myeloma cells at a ratio of 5 splenocytes/1 myeloma cell.

A wild type C57BL/6 mouse vaccinated with ACI-36 (Tau401-418 [pS404/S409]) was used for hybridoma production. The mouse was boosted with ACI-36 vaccine on day 0 then again on day 4 and the fusion was performed on day 7. 84×106 splenocytes from the immunized mouse were fused with SP2-O—Ag14 myeloma cells at a ratio of 5 splenocytes/1 myeloma cell.

A wild type C57BU6 mouse vaccinated with ACI-41 (mix of Tau206-221 [pT212/pS214] and Tau196-211 [pS202/pT205]) was used for hybridoma production. The mouse was boosted with ACI-41 vaccine on day 0 then again on day 4 and the fusion was performed on day 8, 162×106 splenocytes from the immunized mouse were fused with SP2-O—Ag14 myeloma cells at a ratio of 5 splenocytes/1 myeloma cell.

The three fusions resulted in 8×96 well plates and the clones were name according to the plate (1-8) then the row (A-G) and finally the column (1-12).

6.1.2 Screening Method to Select Clones

The 8×96 well plates were first screened twice for IgG expression. Positive expressing clones were then transferred in 24 well plates and cell supernatants (=clones) of growing cells were tested in a Tau ELISA screen and a immunohistochemistry TAUPIR screen, Positive supernatants in ELISA and/or TAUPIR were transferred to T25 flasks and clones were screened again for IgG expression, Tau ELISA screen and TAUPIR.

6.1.3 IgG Screen

Elisa plates were coated with 50 ul/well of anti-mouse IgG antibody (CER Groupe, Marloie, Belgium) in coating buffer for 16 hrs at 4° C. After washing plates with PBS/Tween 100 ul/well of a blocking solution was applied for 1 hr at RT. 50 ul of undiluted hybridoma supernatant were incubated for 1 hr at RT. After a washing step, a mix of the HorseRadish Peroxydase (HRP)-conugated anti-mouse IgG1, IgG2a, IgG2b and IgG3 (Ab Serotec, Raleigh, N.C., USA) was applied on the plates for 1 hr at RT. After a final washing, detection was performed with TMB (3-3',5,5'-tetramethylbenzidine), the phosphatase substrate for HRP, and plates were read at 405 nm using an ELISA plate reader. Results are expressed as O.D. (Optical Density).

6.1.4 Hybridomas Tau ELISA Screen

Hybridomas ELISA screen was performed on pTau peptide (ACI-33, T1.5: Tau5-20 [pY18]; ACI-36, T4.5: Tau401-418 [pS404/S409]; ACI-41, T8.5: Tau206-221 [pT212/pS214] and T9.5: Tau196-211 [pS202/pT205] PolyPeptide Laboratories, Hillerød, Denmark), corresponding Tau peptide (ACI-33, T1.6: Tau5-20; ACI-36, T4.6: Tau401-4; ACI-41, T8.6: Tau206-221 and T9.6: Tau196-211, PolyPeptide Laboratories, Hillerød, Denmark), phosphorylated full-length (441aa) Tau protein (pTau protein, Vandebroek et al., 2005) and full-length (441aa) Tau protein (Tau protein, SignalChem, Richmond, Canada). Finally Bovine Serum Albumin (BSA) was used as negative control.

Plates were coated with 10 ug/ml of corresponding Tau peptide and 1 ug/ml of corresponding Tau protein overnight at 4° C. After washing each well with PBS-0.05% Tween 20 and blocking with 1% BSA in PBS-0.05% Tween 20, undiluted hybridoma supernatant or medium negative control were added to the plates and incubated at 37° C. for 2 hours. After washing plates were incubated with an alkaline phosphatase (AP)-conjugated anti-mouse IgG total antibody (Jackson Laboratories, Baltimore, Pa., USA) for 2 hours at 37° C. After washing plates were incubated with pNPP (para-nitro-phenyl-phosphate), the phosphatase substrate for AP, and read at 405 nm using an ELISA plate reader. Results are expressed as O.D. (Optical Density).

6.1.5 Hybridomas IHC Screen: Binding of Anti-Tau Antibodies to Tangles in Brain Sections from Transgenic Mice (TAUPIR)

TAUPIR experiments were done according to protocol from EXAMPLE 5.1.5.

6.1.6 T25 Flasks IgG Screen

Elisa plates were coated with 5 ug/ml of anti-mouse IgG F(ab')2 fragment specific antibody (Jackson Laboratories, Baltimore, Pa., USA) in carbonate-bicarbonate coating buffer pH 9.6 (Sigma, Buchs, Switzerland) overnight at 4° C. After washing plates, undiluted hybridoma supernatant, positive control IgG1 antibody (6E10 at 1 ug/ml: Covance, Emeryville, Calif., USA) or negative control (culture medium alone) were incubated for 1 hr at RT. After a washing step, the secondary AP-conjugated goat anti-mouse IgG (subclasses 1+2a+2b+3) Fcγ fragment specific antibody (Jackson Laboratories, Baltimore, Pa., USA) was incubated on the plates for 2 hrs at 37° C. After a final washing, detection was performed with pNPP (para-nitro-phenyl-phosphate), the phosphatase substrate for AP, and plates were read at 405 nm using an ELISA plate reader. Results are expressed as O.D. (Optical Density).

6.2. Results

ACI-33 Hybridomas

The cell supernatants from the 8×96 well plates resulting from the fusion were screened for production of IgG. In the 768 wells (8×96 wells) tested 277 wells were positive for IgG expression and were transferred to 24 wells plates. In the 24 well plates 79 clones were growing and supernatant from those cells were analysed. Positive clones were further transferred in T25 flasks and supernatants screened for IgG production, ELISA and TAUPIR (Table 6).

TABLE 6

| 24 well plate screen | | T25 Flasks screen | | |
|---|---|---|---|---|
| | | Positive | | |
| Positive in ELISA | Positive in TAUPIR | in IgG screen | Positive in ELISA | Positive in TAUPIR |
| 1A7 | | 1A7 | | |
| | 1A11 | | | |
| | 1C11 | 1C11 | | |
| 2C9 | | 2C9 | | |
| 3C3 | | 3C3 | 3C3 | |
| 3C5 | | 3C5 | | |
| 3E8 | | 3E8 | | |
| 3G10 | 3G10 | 3G10 | 3G10 | |
| 6C10 | 6C10 | 6C10 | 6C10 | 6C10 |
| 6F3 | | 6F3 | | |
| 6F8 | | 6F8 | | |

The clone 6C10 was the only one positive in the 3 screens and was selected for subcloning.

ACI-36 Hybridomas

The cell supernatants from the 8×96 well plates resulting from the fusion were screened for production of IgG. In the 768 wells (8×96 wells) tested 333 wells were positive for IgG expression and were transferred to 24 wells plates. In the 24 well plates 75 clones were growing and supernatant from those cells were analysed. Positive clones were further transferred in T25 flasks and supernatants screened for IgG production, ELISA and TAUPIR (Table 7).

TABLE 7

| 24 well plate screen | | T25 Flasks screen | | |
|---|---|---|---|---|
| | | Positive | | |
| Positive in ELISA | Positive in TAUPIR | in IgG screen | Positive in ELISA | Positive in TAUPIR |
| 2B6 | 2B6 | 2B6 | 2B6 | 2B6 |
| 2F9 | 2F9 | 2F9 | 2F9 | 2F9 |
| 2G1 | | 2G1 | 2G1 | 2G1 |
| 3A8 | 3A8 | 3A8 | 3A8 | 3A8 |
| 3B9 | | 3B9 | 3B9 | 3B9 |
| 3F11 | 3F11 | 3F11 | | 3F11 |
| | 4A3 | | | 4A3 |
| 4C1 | | 4C1 | 4C1 | 4C1 |
| 4C12 | | 4C12 | 4C12 | 4C12 |
| 4E12 | | 4E12 | 4E12 | 4E12 |
| 5E10 | | 5E10 | 5E10 | |
| 5F5 | | 5F5 | 5F5 | |
| 7D6 | 7D6 | 7D6 | 7D6 | 7D6 |
| 6H1 | | 6H1 | 6H1 | 6H1 |

In order to select clones for the next steps a ranking of all supernatants positives for IgG/ELISA/TAUPIR screens was performed based on the ELISA and TAUPIR results. Ranking the ELISA and TAUPIR results was performed as explained in the methods section. TAUPIR staining was almost identical for the five first clones and this corresponded to the ELISA results. 4C12 was discarded as it was found in the same plate as 4C1 which increased the likelihood of the 2 clones being the same (recognizing the same epitope). The best 4 clones selected were 3A8, 2B6, 4C1 and 6H1. The other 6 clones (4C12, 2G1, 2F9, 7D6, 3B9, 4E12) were kept as back-up.

A ranking of the 10 clones that showed positivity in ELISA screen and TAUPIR screen was performed to select the best ones (Table 8). Highlighted in grey are the best 5 clones.

TABLE 8

Ranking for positive clones in ELISA and TAUPIR

| ranking for ELISA | ranking for TAUPIR |
|---|---|
| 3A8 | 6H1 |
| 2B6 | 4C1 |
| 4C1 | 3A8 |
| 6H1 | 4C12 |
| 4C12 | 2B6 |
| 2G1 | 2F9 |
| 2F9 | 3B9 |
| 7D6 | 2G1 |
| 3B9 | 7D6 |
| 4E12 | 4E12 |

ACI-41 Hybridomas

The cell supernatants from the 8×96 well plates resulting from the fusion were screened for production of IgG. In the 768 wells (8×96 wells) tested 215 wells were positive for IgG expression and were transferred to 24 wells plates. In the 24 well plates 81 clones were growing and supernatant from those cells were analysed. Positive clones were further transferred in T25 flasks and supernatants screened for IgG production, ELISA and TAUPIR (table 9).

TABLE 9

| 24 well plate screen | | T25 Flasks screen | | |
|---|---|---|---|---|
| Positive in ELISA | Positive in TAUPIR | Positive in IgG screen | Positive in ELISA | Positive in TAUPIR |
| | 3D11 | 3D11 | | 3D11 |
| 4H6 | | 4H6 | | 4H6 |
| 5D10 | 5D10 | 5D10 | 5D10 | 5D10 |
| 5E6 | 5E6 | | | |
| 5F10 | | 5F10 | | |
| 6B7 | | 6B7 | 6B7 | |
| 7C2 | 7C2 | 7C2 | 7C2 | 7C2 |
| | | 8G8 | | 8G8 |
| | | 8H8 | 8H8 | 8H8 |

The clones 5D10 and 7C2 were the only ones positive in the 3 screens and were selected for subcloning. The clone 5D10 binds only the peptide T8.5, while the clone 7C2 binds to the two peptides of the ACI-41 vaccine (T8.5 and T9.5) (FIG. 10).

The subclone 5D10A4 originating from 5D10 was specific for pTau peptide.

8.3. Conclusion

The antibodies generated have shown high specificity to pTau peptides with only marginal binding to non-phosphorylated peptides.

From the 3 fusions (ACI-33, ACI-36 and ACI-41), a total of 7 clones were deposited at DSMZ (table 10) and selected for further subcloning.

TABLE 10

List of deposited hybridoma

| Antigen | Vaccine | Hybridoma name | Deposit number | Date of deposit |
|---|---|---|---|---|
| T8: Tau206-221 [pT212/pS214] + T9: Tau196-211 [pS202/pT205] | ACI-41 | ACI-41-Ab1 | DSM ACC3043 | Mar. 3, 2010 |
| T4: Tau401-418 [pS404, pS409] | ACI-36 | 2B6 | DSM ACC3044 | Mar. 10, 2010 |
| T4: Tau401-418 [pS404, pS409] | ACI-36 | 3A8 | DSM ACC3045 | Mar. 10, 2010 |

TABLE 10-continued

List of deposited hybridoma

| Antigen | Vaccine | Hybridoma name | Deposit number | Date of deposit |
|---|---|---|---|---|
| T4: Tau401-418 [pS404, pS409] | ACI-36 | 4C1 | DSM ACC3046 | Mar. 10, 2010 |
| T8: Tau206-221 [pT212/pS214] + T9: Tau196-211 [pS202/pT205] | ACI-41 | 5D10A3 | DSM ACC3047 | Mar. 10, 2010 |
| T1: Tau5-20 [pY18] | ACI-33 | 6C10 | DSM ACC3048 | Mar. 10, 2010 |
| T4: Tau401-418 [pS404, pS409] | ACI-36 | 6H1 | DSM ACC3049 | Mar. 10, 2010 |
| T8: Tau206-221 [pT212/pS214] + T9: Tau196-211 [pS202/pT205] | ACI-41 | 7C2 | DSM ACC3050 | Mar. 10, 2010 |

Example 7

Human AD Brain Slice Specific Staining by Two Antibodies (Acl-41-Ab1 and 5D10), Derived from ACl-41 Vaccinated Mice The objective of this study was to stain neurofibrillary tangles (NFTs) in human Alzheimer's disease (AD) brain using antibody ACl-41-Ab1 (9H3 subclone T89-F4) and 5D10, generated from two different fusions of mice immunized with the ACl-41 vaccine. To test this, a phospho-Tau protein immunoreactivity staining assay (TAUPIR) using human AD brain sections, was employed.

7.1. Methods
7.1.1 5D10 Antibody Generation
5D10 was generated as described in EXAMPLE 9.
7.1.2 ACl-41-Ab1 Generation
7.1.2.1 Fusion A wild type C57BL/6 mouse vaccinated with ACl-41 (ACl-41 vaccine contains a mixture of two phospho-Tau peptides, Tau206-221 [pT212/pS214] and Tau196-211 [pS202/pT205]) was used for hybridoma production. The mouse was boosted with ACl-41 peptide five days prior to fusion. 58×10$^6$ splenocytes from the immunized mouse were fused with SP2/0-O—Ag 14 myeloma cells at a ratio of 5 splenocytes/1 myeloma cell. The fusion resulted in 10×96 well plates that were then screened to determine interesting clones.

7.1.2.2 Hybridomas ELISA Screen

Hybridomas ELISA screen was performed on T8: Tau206-221 [pT212/pS214], T9: Tau196-211 [pS202/pT205] or hyperphosphorylated (hP)-Tau (explained under the Western Blot section) coated plates.

Plates were coated with 2 ug/ml of hP-Tau overnight at room temperature (RT). After washing each well with PBS and blocking with 2% FCS in PBS, hybridoma supernatant was added to the plates and incubated for 1 hour at RT. After a washing step, plates were incubated with peroxidase conjugated AffiniPure Goat Anti-Mouse total Ig (Detection of IgG+IgM, Dako Glostrup, Denmark) in PBS1% FCS for 1 hour at RT. Plates were developed with TMB (3,3',5,5'-tetramethylbenzidine). The reaction was stopped with 2NH$_2$SO$_4$ and read at 450 nm using an ELISA plate reader. Results were expressed in optical density (O.D.) for each hybridoma clones.

For the peptides, plates were coated with 10 ug/ml of Tau206-221 [pT212/pS214] or Tau196-211 [pS202/pT205] overnight at 4° C. After washing with PBS and blocking with 2% NHS in PBS, hybridoma supernatant was added to the plates and incubated for 1 hour at room temperature (RT). After a washing step, plates were incubated with biotinylated anti-mouse IgG (purchased from Vector labs) in PBS1% NHS for 1 hour at RT. A supplemental step was done for the biotin conjugated antibodies and plates were incubated for 30 min in streptavidin-HRP (ABC kit, Vector labs) before detection. After a washing step, plates were developed with TMB (3,3',5,5'-tetramethylbenzidine). The reaction was stopped with 2NH$_2$SO$_4$ and read at 450 nm using an ELISA plate reader. Results were expressed in optical density (O.D.) for each hybridoma clones.

7.1.2.3 Hybridomas IHC Screen: Binding of Anti-Tau Antibodies to Tangles in Brain Sections from Transgenic Mice (TAUPIR)

Binding of antibodies to tangles produced by hybridoma cells was done by immunohistochemistry (IHC) on brain sections of Tau transgenic mice.

Brain sections from old (>20 months) double transgenic biGT mice (GSK-3 transgenic mice crossed with TPLH (human Tau longest isoform (441aa) with the P301 L mutation expressing mice) and from Tau knock-out (TKO) mouse as negative control.

TAUPIR staining was done according to protocol from EXAMPLE 5.1.5.

7.1.2.4 Hybridomas Western Blot Screen (WB)

Binding of antibodies produced by hybridoma cells to pTau in brain extract from transgenic animal and/or hP-Tau extract was done by WB.

Brain homogenization of wild-type FVB, TPLH, biGT and Tau knock-out (TKO) mouse was done in the following buffer: 25 mM Tris/HCl pH7.6, 150 mM NaCl, 1 mM EDTA, 1 mM EGTA, 30 mM NaF, 0.2 mM Na$_3$VO$_4$, 1 nM Okadaic add, 1 mM phenylmethylsulfonyl fluoride (PMSF), 5 mM Na$_4$P2O$_7$, 1 tablet complete protease inhibitor cocktail (CPIC) per 12 ml total. To obtain total brain homogenate the brain was homogenize on ice in 10 vol/weight hemisphere (ml/g) with a motor-driven potter-like (glass tube/teflon pestle) used at 700 rpm.

For hP-Tau extraction, brain of TPLH and TKO mouse was homogenized with the following buffer: 100 mM MES pH 6.8, 1 mM β-mercapto-ethanol, 5 mM EDTA, 2.5 mM PMSF, 5 µg/ml tosyl-L-lysine chloromethyl ketone (TLCK), 100 mM NaF, 1 nM Okadaic acid, 0.2 mM Na$_3$VO$_4$ and 1 tablet complete protease inhibitor cocktail (CPIC) per 12 ml total. The brain was homogenized on ice in 6 vol/weight hemisphere (ml/g) with a motor-driven potter-like (glass tube/teflon pestle) used at 700 rpm. The homogenate was centrifuged at 20000×g 30 min at 4° C. and the supernatant transferred and heated rapidly to 95° C. where it was kept for 10 min after cooling it in melting ice. A centrifugation step was done before supernatant aliquots were done and stored at −20° C. as "hP-Tau".

Total brain homogenate was diluted half in sample buffer (125 mM Tris/HCl pH6.8, 4% (w/v) sodium dodecyl sulfate (SDS), 20% glycerol, 0.01% bromophenol blue)+5% beta-mercapto-ethanol then heat rapidly to 95° C. Samples were kept 5 min, diluted ¼ in sample buffer, heat again to 95° C. then cooled down and spin at 14000 rpm for 5 min to clear debris that were not solubilized. Supernatants were collected and loaded on a SDS-PAGE gel. The transfer to the nitrocellulose membrane (Hybond-ECL) was done in transfer buffer (25 mM Tris pH 8.6, 190 mM Glycine, 20% methanol). Membrane was transfered to the blocking solution (0.1% Tween in TBS (50 mM Tris.HCL, 017.6, 150 mM NaCl)+5% milk-powder) prior to overnight incubation at 4° C. with undiluted hybridoma supernatant. Incubation with secondary antibody HRP-conjugated goat anti-mouse (Dako, Glostrup, Denmark) diluted 1/10,000 in blocking solution was performed at RT for 1 hour. Detection was done using the ECI-Western Blotting Detection Reagents from GE Healthcare.

7.1.3 Binding of Anti-Phospho-Tau Antibodies to Tau Tangles in a Human AD Brain

The anti-phospho Tau antibody clones ACI-41-Ab1 (9H3 T89-F4 subclone) (mouse IgM isotype) and 5D10 (mouse IgG isotype) were generated from two separate fusions of ACl-41 vaccinated mice, The ACl-41 vaccine contains a mixture of two phospho-Tau peptides, Tau206-221 [pT212/pS214] and Tau196-211 [pS202/pT205]. Binding of antibody clone T89-F4 to tangles on brain slices from human AD brain was done by TAUPIR immunohistochemistry. Cortical brain sections from individuals with AD, progressive supranuclear palsy (PSP), and healthy controls were used. Brain sections were washed for 5 min in PBS then incubated for 15 min at RT in 1.5% $H_2O_2$ in PBS:MeOH (1:1) to block endogenous peroxidase. After washing the sections 3 times in PBST (PBS/0.1% Triton×100) they were incubated for 30 min at RT in PBST+10% FCS (fetal calf serum) blocking solution. The incubation with the primary antibodies (clone 9H3 T89-F4, 5D10 and AT100 as a positive control) was done overnight at 4° C. Sections were washed 3 times in PBST before incubation with an HRP-conjugated goat anti-mouse (purchased from Dako, Glostrup, Denmark) secondary antibody in PBST/10% FCS for 1 hour at RT. Prior to detection, sections were washed 3 times with PBST and incubated in 50 mM Tris/HCl pH7.6 for 5 min. Detection was done by incubating the sections for 3 min in Diaminobenzidine (DAB: 1 tablet in 10 ml of 50 mM Tris.HCl+3 ul $H_2O_2$ 30%; MP Biomedicals, Solon, Ohio, USA). The reaction was stopped by washing the sections 3 times in PBST. The sections were then transferred onto silanized glass-plates and air-dried on a warm-plate at 50° C. for 2 hours. Counterstaining was done by incubating with Mayers hematoxylin (Fluka Chemie, Buchs, Switzerland) for 1 min followed by a washing step for 4 min in running tap-water. Sections were deparaffined by passing in Xylol 2 times for 5 min and 2 times for 1 min in 100% EtOH, followed by 1 min wash in 90%, 70%, 50% EtOH and distilled water. For antigen retrival, sections were boiled for 10 min in a 0.01 M citric acid solution (pH 6.0) and cooled down for 20 min. Finally, sections were mounted with DePeX (BDH Chemicals Ltd., Poole, England) under glass coverslips. Stained sections were examined microscopically with epifluorescence illumination optics and a 3CCD camera (Leica, Wetzlar, Germany). Images were captured and analyzed using dedicated software (IM500, Leica).

7.2. Results 7.2.1 Hybridomas Screening

ELISA screens were performed as described in the methods and 172 hybridomas clones were selected and transferred to 12 well plates. Subsequent ELISAs were performed to evaluate the specificity of the antibodies produced against the pTau peptides Tau206-221 [pT212/pS214], Tau196-211 [pS202/pT205] and/or hP-Tau extract. This resulted in 25 positives clones for the pTau peptides and 21 clones showed specificity for hP-Tau (FIG. 11).

Immunohistochemistry studies were done in parallel with ELISA analysis. Different staining patterns were found in the clones transferred to 12 well plates. Unspecific glial, nuclear and cytoplasmatic staining was observed on some biGT sections incubated with undiluted supernatant from the selected clones Supernatant from clone 9H3 (ACl-41-Ab1) was staining with high specificity cytoplasmic tangle structures WB screen on brain and hP-Tau extracts from different mice was performed using the undiluted supernatant from selected hybridomas. No reaction with Tau was observed for any of the hybridoma supernatants tested.

7.2.2 Staining of Neurofibrillary Tangles in Human Alzheimer's Disease Brain Sections The ability of antibody clones ACl-41-Ab1 (9H3 subclone T89-F4) and 5D10 to bind to NFTs in human AD brain was examined by TAUPIR immunohistochemistry. The anti-phospho Tau antibody clone T89-F4 bound to phospho-Tau containing NFTs in human AD brain (FIG. 12).

The ability of antibody 5D10 to bind to NFTs in human AD cortical brain sections was examined by TAUPIR immunohistochemistry. The anti-phospho Tau antibody clone 5D10 bound to phospho-Tau containing NFTs and neuropil threads in human AD brain cortical sections (FIG. 13).

7.3. Conclusion

Screening of ACl-41 generated hybridoma clones by ELISA yielded 36 clones binding to phosphorylated peptides and/or full length hP-Tau extract. Screening by TAUPIR of these 36 clones confirmed staining to cytoplasmic tangle structure by one clone (9H3), ACl-41-Ab1.

The two antibodies ACl-41-Ab1 (9H3-F4) and 5D10 demonstrated specific binding to NFTs and neuropil threads in human AD brain section.

Example 8

Potency of ACl-35 Produced by 2 Different Processes to Induce pTau-Specific IgG Responses after i.p. or s.c. Immunizations in Wild-Type Mice (C57BL/6)

The objective of this study was to evaluate the potency of ACl-35 (Tau393-408 [pS396/pS404]) produced by 2 different processes, Process A ACl or Process L3 ACl to induce antibody titers following subcutaneous (s.c.) or Intraperitoneal (i.p.) injection in wild-type C57BL/6 mice. Mice were immunized 3 times with 2 weeks intervals and were bled 1 week before the first injection and then 1 week after each immunization. Total anti-pTau (Tau393-408 [pS396/pS404]) IgG responses were measured by ELISA. In addition, the isotypes pattern of the antibody response was analyzed after 3 immunizations to evaluate the distribution of the different subclasses of IgGs as well as IgM. Antibody titers against the corresponding non-pTau (Tau393-408) peptide were analyzed. T cell responses induced by ACl-35 were analyzed using the ELISPOT technique.

8.1. Methods 8.1.1 Preparation of the Vaccine ACl-35 Process A ACl

ACl-35 vaccines were prepared according to protocol from EXAMPLE 3. The liposomal suspension (batch ACl-35-081103-B) was then aliquoted prior to storage at 2-8° C. The final peptide/phospholipid molar ratio was 1:100.

8.1.2 Preparation of the Vaccine ACl-35 Process L3 ACl

Tau-derived tetrapalmitoylated phosphopeptide Tau393-408 [pS396/pS404] (human Tau 393-408 with phospho group on S396 and S404) (4.0 mg) was weighed into a 25 ml glass vial to which was added hexafluoroisopropanol (HFIP) (5 ml). This clear solution was then added to a stirred solution of Dimyristoyl phosphatidylcholine (DMPC), Dimyristoyl phosphatidylglycerol (DMPG), Cholesterol and adjuvant Monophosphoryl Lipid A (MPLA) (all Avanti Polar Lipids Inc. AL, USA) in Chloroform (35 ml) (molar ratio 9:1:7:0.2 respectively), The resulting solution was then filtered through a 0.2 um hydrophobic PTFE filter membrane into a 250 ml glass round-bottom flask. Organic solvent was then removed by evaporation under reduced pressure at 40° C. and then under high vacuum for 3 hours. The resulting thin-film was rehydrated by addition of PBS (40 ml) and gently agitation at RT for 18 hours. The liposomal suspension (batch ACl-35-081103-A) was then aliquoted prior to storage at 2-8° C. The final peptide/phospholipid molar ratio was 1:100.

8.1.3 Immunizations 13 weeks old C57BL/6 mice (10 mice per group) received s.c. or i.p. injections of the vaccine on three occasions with a 2 weeks interval between each administration (day(d)0, d14, d28) according to Table 11. 1 week (d-7) before the first immunizations then 7 days after the injections (i.e. d7, d21, d35), and at sacrifice (d56) blood samples were collected and plasma prepared. Tau393-408 [pS396/pS404]-specific IgG and IgM antibody titers and IgG isotypes patterns were determined by ELISA. As control non-pTau393-408-specific IgG antibody titers were determined by ELISA.

8.1.5 Quantification of Tau Peptide-Specific Cytokine Producing T Cells by ELISPOT Cytokine production of Tau393-408 [pS396/pS404] and Tau393-408-specific T cells was assessed by ELISPOT. Multiscreen 96-well nitrocellulose plates (Millipore, Moisheim, France) were coated overnight with anti-mouse IFN-γ and IL-4 monoclonal antibodies according to the manufacturers' instructions (Pharmingen BD, San Diego, Calif., USA), Single cell suspensions were prepared from spleens of immunized mice and incubated at serial dilutions with Tau393-408 [pS396/pS404] and Tau393-408 (10 and 1 ug/ml) and Concavalin A (5 ug/ml, Amersham) at 37° C. under 5% $CO_2$ for 72 hours. The plates were then washed and incubated 1 hour at 37° C. with biotinylated anti-mouse IFN-γ and IL-4 monoclonal antibodies. After washing, the plates were incubated for 1 hour at 37° C. with Streptavidin-HRP and after washing, spots were developed by adding a substrate (AEC, 3-amino-

TABLE 11

Mice Immunization

| Group | Number of Animals and Gender | Treatment/ Volume[a] | Vaccine Batch | Process | Route of Administration[b] | Dose level Quantity of Tau peptide ug/dose[c] | Quantity of MPLA ug/dose[c] |
|---|---|---|---|---|---|---|---|
| 1 | 10 females | ACI-35 0.2 ml | ACI-35-081103-A | L3 ACI | i.p. | 10 | 16 |
| 2 | 10 females | ACI-35 0.2 ml | ACI-35-081103-A | L3 ACI | s.c. | 10 | 16 |
| 3 | 10 females | ACI-35 0.2 ml | ACI-35-081103-B | A ACI | i.p. | 13 | 19 |
| 4 | 10 females | ACI-35 0.2 ml | ACI-35-081103-B | A ACI | s.c. | 13 | 19 |

[a]theoretical volume
[b]s.c.: subcutaneous
[c]measured quantity determined after analysis 8.1.4 Quantification of Tau Peptide-Specific Antibodies Specific IgG antibodies for Tau393-408 [pS396/pS404] were determined by ELISA in the 5 plasma bleeding samples. Specific Tau393-408 IgG antibodies, Tau393-408 [pS396/pS404]-specific IgM and IgG isotypes antibodies were determined by ELISA in the d35 plasma bleeding sample. Plates were coated with 10 ug/ml of corresponding Tau peptide overnight at 4° C. After washing each well with PBS-0.05% Tween 20 and blocking with 1% BSA in PBS-0.05% Tween 20, serial dilutions of plasma were added to the plates and incubated at 37° C. for 2 hours. After washing, plates were incubated with an alkaline phosphatase (AP)-conjugated anti-mouse IgG antibody (Jackson Laboratories, Baltimore, Pa., USA) or isotype specific antibodies (horseradish Peroxidase (HRP)-conjugated anti-mouse IgM, AP-conjugated anti-mouse IgG1, biotin-conjugated anti-mouse IgG2a and IgG3, purchased from Pharmingen BD, San Diego, Calif., USA and HRP-conjugated anti-mouse IgG2b from Zymed Laboratories, San Francisco, Calif.) for 2 hours at 37° C. After washing, plates were incubated with pNPP (para-nitro-phenyl-phosphate), the phosphatase substrate for AP, or ABTS (2,2'-azino-bis(3-ethylbenzthiazoline-6-sulphonic acid)), the substrate for HRP and read at 405 nm using an ELISA plate reader. A supplemental step was done for the biotin conjugated antibodies where plates were incubated for 45 min in streptavidin-HRP (R&D Systems, Minneapolis, Minn., USA) before detection using ABTS. Results are expressed as O.D. (Optical Density) at the first dilution and a non saturated dilution for IgG and at non-saturated O.D. for IgG isotypes and IgM.

9-ethylcarbazoie). The number of spots per well was counted by eye under a stereo-microscope and the results were expressed as spots per $10^6$ cells. Spleen of naïve mice were used as negative controls.

8.1.6 Non Radioactive Cell Proliferation Assay

Single cell suspensions were prepared from spleens of immunized mice and incubated at serial dilutions with Tau393-408 [pS396/pS404] and Tau393-408 (10 and 1 ug/ml) and Concavalin A (5 ug/ml, Amersham) at 37° C. under 5% $CO_2$ for 72 hours. To measure proliferation, a non-radioactive cell proliferation assay (MTT) kit was used (Promega, Dubendorf, Switzerland), according to the manufacturer's instructions. Briefly, 15 ul of Dye solution was added to each well and plates were incubated during 4 hours at 37° C. Next, 100 ul solubilization/Stop solutions was added per well and the plates were incubated at 4° C. for a minimum of an additional 1 hour. The O.D. was measured at 570 nm and 690 nm wavelengths.

8.2. Results 8.2.1 Evaluation of the Antibody Response Induced by Different Vaccines The ACl-35 vaccine induced a robust anti-pTau393-408 [pS396/pS404] IgG response following i.p. or s.c. injection independent of the process used. In general robust antibodies titers were already present at 7 days after the first vaccine immunization. For the same process there was a higher response for s.c. injection compared to i.p. injection for d21 and d35 for Process L3 ACl vaccinated animals (FIG. 14, 2-way Anova, $P<0.001$ d21/d35) and for d21, d35 and d56 for Process A ACl injected animals (FIG. 14, 2-way Anova, P<0.001 d21/d35, P<0.01 d56). For i.p. injected animals, the response was higher with the L3 ACl Process compared to the A ACl Process at the early bleeding d7 and d21 (FIG. 14, 2-way Anova, P<0.001 d7/d21) whereas there was no difference for s.c. injected animals. In summary the two processes seemed equivalent when they were injected s.c.

Analyzes of the results at a non-saturated O.D. dilution confirmed the difference between i.p. and s.c. injection of the different ACl-35 vaccine process. In summary the results remained the same showing that s.c. injection give higher Ab titers then i.p. injection and that for s.c. injection there is no significant differences between the 2 processes To determine the isotypes of vaccine-induced antibodies, plasma from d35 were analyzed by isotype specific IgG ELISA. ACl-35 induced in all groups anti-pTau393-408 [pS396/pS404] IgG of the IgG1, IgG2a, IgG2b and IgG3 isotypes. IgG2b was the dominant isotype with high O.D. even at a dilution of 1/3200. For the IgG1 subclass there was a higher response for s.c. compared to i.p. injection for both processes (FIG. 15, 1-way Anova, P<0.05). The same difference was observed for the IgG3 subclass. For IgG2a and 2b subclasses there was no difference between the 2 processes tested nor between i.p. or s.c. injection of the vaccine.

There was no difference between the 2 tested processes in term of anti-pTau393-408 [pS396/pS404] IgM antibody responses whereas there was a significant higher IgM titers with i.p. injection compared to s.c. injection (FIG. 16a, 1-way Anova, P<0.001).

Antibody titers against non phospho Tau393-408 were also analyzed for all the groups. Anti-Tau393-408 specific IgG antibodies were detected for all the groups but those titers were lower than the anti-pTau393-408 [pS396/pS404]. There was no difference in anti-Tau393-408 IgG titers between to the 2 processes or the mode of injection (FIG. 16b, 1-way Anova, P>0.05).

The mean of the first three IgG titers for the different Tau peptides are shown in Table 12:

TABLE 12

Mean of the first three anti-Tau393-408 [pS396/S404] IgG titers (O.D. at 1/100 dilution)

| Vaccine pTau peptide | Process to generate vaccine | Mode of injection | d7 | d21 | d35 | Mean |
|---|---|---|---|---|---|---|
| Tau393-408 [pS396/pS404] | L3 ACl | i.p. | 1.899 | 2.284 | 1.825 | 2.003 |
| | | s.c. | 1.485 | 2.956 | 2.444 | 2.295 |
| | A ACl | i.p. | 0.902 | 1.467 | 1.708 | 1.359 |
| | | s.c. | 1.276 | 2.964 | 2.426 | 2.222 |

8.22 Evaluation of the T Cell Response Induced by Acl-35

In vitro restimulation of splenocytes with ConA, pTau393-408 [pS396/pS404] or Tau393-408 peptides did not result in proliferation differences between the tested groups (FIG. 17) whereas it was positive for ConA.

Re-stimulation using 10 ug/ml of Tau393-408 [pS396/S404] induced cytokine secretion that was higher for splenocytes from vaccinated mice compared to the naïve mice (FIG. 18). Process L3 ACl injected s.c. induce the higher level of both cytokine analyzed with no clear difference between IFN-γ and IL-4. The i.p. or s.c. injection of Process A ACl induce cytokine secretion that is mainly IL-4 and the levels are higher for the i.p. injection. Re-stimulation using 1 ug/ml of Tau393-408 [pS396/S404] induced comparable results to the re-stimulation using 10 ug/ml of Tau393-408 [pS396/S404].

The re-stimulation using the non-pTau939-408 peptide induced comparable results to the pTau peptide counterparts (FIG. 18). Again the use of Process A ACl induce cytokine secretion that is mainly IL-4.

8.3. Conclusion

ACl-35 vaccine induced robust IgG titers already after 1 immunization independently of the Process or the mode of injection tested. In term of comparison, s.c. injection of the vaccines independently of the process used gave the higher IgG antibodies titers. I.p. injection of ACl-35 Process A ACl resulted in less IgG1 and IgG3 titers compared to the other group. I.p. injection of ACl-35 resulted in significant higher IgM titers than s.c. injection. Finally, all groups have IgG titers against the non-pTau393-408 peptide.

Re-stimulation using pTau or Tau peptides induced cytokine production in the ELISPOT study that was mainly IL-4 for the Process A ACl vaccinated mice.

Example 9

Immunogenicity of Tau Vaccine in Tau P301L Transgenic Mice (TPLH)

The objective of this study was to analyze the immunogenicity of anti-Tau vaccination using subcutaneous (s.c.) injection of the tau liposomal vaccines (ACl-33, ACl-35, ACl-39 and ACl-40) in Tau P301L transgenic mice, 9.1. Methods 9.1.1 Tau P301L Transgenic Mice (TPLH)

Homozygous Tau P301L transgenic mice (TPLH) with FVB/N background were used to test the efficacy of s.c. ACl-33 or ACl-35 vaccination, These mice express the longest human tau isoform with the P301L mutation under control of the mouse thy1 promoter. The clinical symptoms set in at age 6 to 7 months, and aging TPLH mice develop a moribund tauopathy with progressive neuronal impairment and formation of neurofibrillary tangles (NFT). In terminal stages they lose weight and die suddenly (likely by breathing-problems (asphyxia), most of them at age 9 to 11 months and without exception before 12 months.

9.1.2 Preparation of the Vaccine ACl-33 and ACl-35

Vaccines were prepared according to process A described in EXAMPLE 3.

The liposomal suspension (batch ACl-33-081031-A and batch ACl-35-081015-A+ACl-35-090402-A) was then aliquoted prior to storage at 2-8° C. The final peptide/phospholipid molar ratio was 1:100.

9.1.3 Immunizations

ACl-33 ACl-39 and ACl-40

TPLH mice between 21 and 31 weeks (8-10 mice per group: mix of females (♀) and males (♂) received s.c. injections of the vaccine on five occasions (Table 14). The three first immunizations were done with a 2 weeks interval between each administration (day(d)0, d13, d28) according to Scheme 1. The animals were then boosted once per month for two months (d91 and d133). 1 day (d-1) before the first immunizations then after the second (d27) and third (d41) immunizations blood samples were collected. Blood collection was also performed before, in between and after the boosts (d76, d104, d135). Serum was prepared with the blood by letting the samples clot overnight then taking the supernatant after centrifugation. Phospho-tau peptide specific IgG and IgM antibody titers and IgG isotype patterns were determined by ELISA. Specific IgG antibodies titers for non-pTau, full-length (441aa) Tau protein and phosphorylated full-length (441aa) Tau protein were also determined by ELISA. ACl-35

TPLH mice between 22 and 31 weeks (10 mice per group: mix of females (♀) and males (♂)) received s.c. injections of the vaccine on five occasions (Table 13). The three first immunizations were done with a 2 weeks interval between each administration (day(d)0, d13, d27) according to Scheme 1. The animals were then boosted once per month for two months (d91 and d133). 1 day (d-1) before the first immunizations then after the second (d26) and third (d40) immunizations blood samples were collected. Blood collection was also performed before, in between and after the boosts (d75, d103, d145, d155). Serum was prepared with the blood by letting the samples clot overnight then taking the supernatant after centrifugation. Tau393-408 [pS396/pS404]-specific IgG and IgM antibody titers and IgG isotype patterns were determined by ELISA. Specific IgG antibodies titers for non-pTau393-408, full-length (441aa) Tau protein and phosphorylated full-length (441aa) Tau protein were also determined by ELISA.

blocking with 1% BSA in PBS-0.05% Tween 20, serial dilutions of sera were added to the plates and incubated at 37° C. for 2 hours. After washing, plates were incubated with an alkaline phosphatase (AP)-conjugated anti-mouse IgG total antibody (Jackson Laboratories, Baltimore, Pa., USA) or isotype specific antibodies (horseradish Peroxidase (HRP)-conjugated anti-mouse IgM, AP-conjugated anti-mouse IgG1, biotin-conjugated anti-mouse IgG3, purchased from Pharmingen BD San Diego, Calif., USA; biotin-conjugated anti-mouse IgG2a purchased from Invitrogen CA, USA and HRP-conjugated anti-mouse IgG2b from Zymed Laboratories, San Francisco, Calif.) for 2 hours at 37° C. After washing, plates were incubated with pNPP (para-nitro-phenyl-phosphate), the phosphatase substrate for AP, or ABTS (2,2'-azino-bis(3-ethylbenzthiazoline-6-sulphonic acid)), the substrate for HRP and read at 405 nm using an ELISA plate reader. A supplemental step was done for the biotin conjugated antibodies where plates were incubated for 45 min in streptavi-

TABLE 13

Mice Immunization

| Group | Number of Animals and Gender | Treatment/ Volume[a] | Vaccine Batch | Route of Administration[b] | Dose level Quantity of tau peptide ug/dose[c] | Quantity of MPLA ug/dose[c] |
|---|---|---|---|---|---|---|
| 1 | 5 ♀<br>5 ♂ | ACI-33<br>0.2 ml | ACI-33-081031-A | s.c. | 9 | 12 |
|  | 5 ♀<br>3 ♂ | PBS<br>0.2 ml | N.A. | s.c. | N.A. | N.A. |
| 2 | 5 ♀<br>5 ♂ | ACI-35<br>0.2 ml | ACI-35-081015-A<br>ACI-35-090402-A | s.c. | 16<br>8 | 23<br>27 |
|  | 5 ♀<br>5 ♂ | PBS<br>0.2 ml | N.A. | s.c. | N.A. | N.A. |
| 3 | 5 ♀<br>5 ♂ | ACI-39<br>0.2 ml | ACI-39-090202-A | s.c. | 9.6 | 28.8 |
|  | 5 ♀<br>3 ♂ | PBS<br>0.2 ml | N.A. | s.c. | N.A. | N.A. |
| 4 | 5 ♀<br>5 ♂ | ACI-40<br>0.2 ml | ACI-40-090202-A | s.c. | 12 | 24.4 |
|  | 5 ♀<br>3 ♂ | PBS<br>0.2 ml | N.A. | s.c. | N.A. | N.A. |

N.A. = not applicable
[a] theoretical volume
[b] s.c.: subcutaneous
[c] measured quantity determined after analysis 9.1.4 Quantification of Tau Peptide-Specific Antibodies For ACI-33, ACI-39 and ACI-40 treated mice, specific IgG antibodies for respectively Tau5-20 [pY18], Tau206-221 [pT212, pS214] and Tau196-211 [pS202, pT205] were determined by ELISA in the 6 sera bleeding samples. Tau5-20-, full-length (441aa) Tau protein- and phosphorylated full-length (441aa) Tau protein-specific IgG were determined in the sera from d-1 and d41. Phospho-tau peptide-specific IgM and IgG isotype antibodies were determined by ELISA in the d41 sera bleeding sample.

For ACI-35 treated mice, specific IgG antibodies for Tau393-408 [pS396/pS404] were determined by ELISA in the 7 sera bleeding samples. Tau393-408-, full-length (441 aa) Tau protein- and phosphorylated full-length (441 aa) Tau protein-specific IgG were determined in the sera from d-1 and d40. Tau393-408 [pS396/pS404]-specific IgM and IgG isotype antibodies were determined by ELISA in the d40 sera bleeding samples.

Plates were coated with 10 ug/ml of corresponding Tau peptide and 1 ug/ml of corresponding Tau protein overnight at 4° C. After washing each well with PBS-0.05% Tween 20 and din-HRP (R&D Systems, Minneapolis, Minn., USA) before detection using ABTS. Results are expressed as O.D. (Optical Density) at a non-saturated O.D. for IgG, IgG isotypes and IgM.

9.1.5 Binding of Anti-Tau Antibodies to Tau Tangles on Brain Slices from Transgenic Animal (TAUPIR)

Binding of antibodies present in the serum of ACI-33, ACI-35, ACI-39 and ACI-40 vaccinated animals to tangles on brain slices was done by TAUPIR immunohistochemistry.

TAUPIR staining was done according to protocol from EXAMPLE 5.15.

9.1.6 Western Blot (WB)

Western Blot were done according to protocol from EXAMPLE 5.1.6 except that washing was performed before detection with the Qdot 625 streptavidin conjugate solution (Invitrogen, CA, USA) for 30-60 min at RT.

9.2. Results 9.2.1 IgG Antibody Response

All vaccine constructs have generated specific IgG antibody titers.

ACI-33 vaccine induced a specific IgG response following s.c. injection. After 2 immunizations (d27), the IgG response remained stable with no increase with the third immunization (d41) (FIG. 19 1-way Anova P<0.001 d-1 vs d27, P>0.05 d27 vs d41). A decrease in antibody titers was observed at d76 (FIG. 19, 1-way Anova P<0.001 d41 vs d76) and boosting of the animals increased slightly again the titers at d104.

ACl-35 vaccine induced an anti-Tau393-408 [pS396/pS404]-IgG response following s.c. injection. After 2 immunizations (d26), the IgG response was not increased with the third immunization (d40) (FIG. 20, 1-way Anova P<0.001 d-1 vs d26 and d40). Boosting of the animals increased again the titers at d103 (FIG. 20, 1-way Anova P<0.05 d-1 vs d104 and P<0.001 d-1 vs d145).

ACl-39 vaccine induced an anti-Tau206-221 [pT212, pS214] IgG response following s.c. injection. After 2 immunizations (d27), the IgG response remained stable with no increase with the third immunization (d41) (FIG. 21, 1-way Anova P<0.001 d-1 vs d27/d41). There was a drop in the titers at d76 and boosting of the animals restored the titers to same level as after 3 immunizations (FIG. 21, 1-way Anova P<0.05 d-1 vs d76 and P>0.05 d41 vs d104).

Analyzes of the results at a non-saturated O.D. dilution showed the same conclusions as the saturated 1/100 dilution (1-way Anova P<0.05 d-1 vs d27/d41/d104 and P>0.05 d-1 vs d76).

ACl-40 vaccine induced an anti-Tau196-211 [pS202, pT205] IgG response following s.c. injection. After 2 immunizations (d27), the IgG response remained stable with no increase with the third immunization (d41) (FIG. 22, 1-way Anova P<0.001 d-1 vs d27, P>0.05 d27 vs d41). A decrease in antibody titers was observed at d76 (FIG. 22, 1-way Anova P<0.001 d41 vs d76) and boosting of the animals increased slightly again the titers at d104.

Analyzes of the results at a non-saturated O.D. dilution showed the same conclusions as the saturated 1/100 dilution (1-way Anova P<0.001 d-1 vs d27, P>0.05 d27 vs d41 and P<0.01 d41 vs d76).

9.2.2. Isotype Analysis

ACl-33 vaccination induced antibody titers that were mainly of the IgG2a and 2b subclasses following 3 s.c. immunizations (FIG. 23). IgG1 IgG3 and IgM level were low and there was a significant different between the levels of IgG2a/2b and IgG1/IgM (FIG. 23, 1-way Anova P<0.05 IgG1 vs IgG2a/2b, P<0.001 IgM vs IgG2a/2b).

ACl-35 vaccination induced antibody titers that were mainly of the IgG2a and 2b subclasses following 3 s.c. immunizations (FIG. 24). IgG1 level were lower with a significant difference between IgG1 and IgG2a (FIG. 24, 1-way Anova P<0.05 IgG1 vs IgG2a). IgG3 and IgM level were low and there was a significant different between the levels of IgG2a/2b and IgG3/IgM (FIG. 24, 1-way Anova P<0.05 IgG3/IgM vs IgG2b, P<0.0001 IgG3/IgM vs IgG2a).

ACl-39 vaccination induced antibody titers that were mainly of the IgG2a and 2b subclasses following 3 s.c. immunizations (FIG. 25). IgG1, IgG3 and IgM level were significantly lower than IgG2a/2b titers (FIG. 25, 1-way Anova P<0.05 IgG2b vs IgG1/IgG3, P<0.01 IgG2a vs IgG1/IgG3, P<0.001 IgG2a/2b vs IgM).

ACl-40 vaccination induced antibody titers that were mainly of the IgG2b subclass following 3 s.c. immunizations (FIG. 26, 1-way Anova P<0.05 IgG2b vs IgG2a and P<0.001 IgG2b vs IgG1/IgG3/IgM). IgG2a titers were also higher then IgM (FIG. 26, 1-way Anova P<0.01 IgG2a vs IgM).

9.2.3 Antibody Specificity

IgG titers induced after 3 s.c. injection of tau vaccines were also analyzed on different Tau peptides (pTau peptide and Tau peptide) and proteins (anti-phosphorylated full-length (441aa) Tau protein=anti-pTau protein and anti-full length (441aa) Tau protein anti-Tau protein.

In ACl-33 vaccinated mice, the d-1 bleeding was used as a control and for each different coating there was a difference between the pre-bleeding and the sera collected after 3 immunizations for Tau5-20 [pY18] and Tau protein coatings (FIG. 27, 1-way Anova P<0.001 d-1 vs d41 for Tau5-20 [pY18], P<0.05 d-1 vs d41 for Tau protein).

In ACl-35 vaccinated mice, the d-1 bleeding was used as a control and there was a significant difference between d-1 and d40 only for anti-Tau393-408 [pS396/pS404] titters (FIG. 28, 1-way Anova P<0.0001 d-1 vs d40 for anti-Tau393-408 [pS396/pS404] titters). The d40 antibody levels obtained on the Tau393-408 [pS396/pS404] peptide were also significantly different then the levels obtained on all the other coatings (FIG. 28, 1-way Anova P<0.0001 d40 anti-Tau393-408 [pS396/pS404] vs d40 anti-Tau393-408/pTau protein/Tau protein).

In ACl-39 vaccinated mice, the d-1 bleeding was used as a control and only for the Tau206-221 [pT212, pS214] coating there was a difference between the pre-bleeding and the sera collected after 3 (FIG. 29; 1-way Anova P<0.001 d-1 vs d41 for Tau206-221 [pT212, pS214]).

In ACl-40 vaccinated mice, the d-1 bleeding was used as a control and there was a difference between the pre-bleeding and the sera collected after 3 immunizations for Tau196-211 [pS202, pT205] and Tau 196-211 coatings (FIG. 30, 1-way Anova P<0.001 d-1 vs d41 for Tau196-211 [pS202, pT205], P<0.05 d-1 vs d41 for Tau196-211).

Mouse serum was further used in TAUPIR experiments to determine if anti-Tau antibodies present in the serum could recognize tangles in brain slices from Tau transgenic animal.

WB on brain extract from different mice were also performed using mouse sera or the control antibody Tau-5 detection all form of Tau (pTau and Tau).

Data are summarized in the table 14 hereafter.

TABLE 14

Summary of TAUPIR and WB experiment on TPLH vaccinated mice

| Vaccine | TAUPIR (positive/total mice) | Western Blot (positive/total mice) |
| --- | --- | --- |
| ACI-33 | 6/10 | 3/9 |
| ACI-35 | 4/10 | 0/4 |
| ACI-39 | 7/10 | 1/5 |
| ACI-40 | 10/10 | 3/7 |

9.3. Conclusion

Anti-tau antibody titers were analyzed for their binding to different Tau and pTau peptides as well as the full-length pTau or Tau protein. Tau liposomal immunization generated IgG antibodies binding specifically to pTau peptides and phospho-tau protein with weaker binding to non-phosphorylated peptides and protein.

In term of IgG isotypes there was a low IgG1 antibody response compared to IgG2b and IgG3. Low IgM response was observed which is in accordance with the mode (s.c.) of immunization.

The specificity of the antibodies generated by tau vaccine immunized mice were tested in TAUPIR and almost all mouse serum show high binding to Tau tangles present in the brain slices for mutant Tau animals.

Example 10

Efficacy in Tau P301L Transgenic Mouse Model Following ACI-33 or ACI-35 Vaccination The objective of this study was to analyze the efficacy of anti-Tau vaccination using subcutaneous (s.c.) injection of the ACI-33 (Tau5-20 [pY18]) or ACI-35 (Tau393-408 [pS396/pS404]) vaccines in Tau P301L transgenic mice, Mice were immunized 5 times and behavior changes were analyzed by rotarod analyzes performed during the life span of the animal.

10.1 Methods
10.1.1 Vaccine Preparation ACI-33 and ACI-35 vaccines were prepared according to the protocol from EXAMPLE 3,
10.1.2. Immunization Animals were immunized with either ACI-33 or ACI-35 according to the protocol described in EXAMPLE 9 (Scheme 2 for ACI-33 and scheme 3 for ACI-35)

10.1.3 Behaviour (Rotarod)

To observe the motoric condition of the animals, the automated rotarod test was performed. Five mice were simultaneously tested on a revolving rotating rod (diameter 3 cm), separated by non-translucent dividers. During the test, the rod accelerates from 4 to 40 rpm in 5 min. For each mouse the time it remained on the revolving rod was scored, with a maximum of 5 min.

10.2 Results

To evaluate the motoric condition of the TPLH after ACI-33 or PBS treatments, the mice were subjected to the rotarod test on five different occasions (FIG. 31). A significant difference between ACI-33 and PBS injected animals was observed at age 7.3 months (FIG. 31, 2-way Anova P<0.001 age 7.3 months). This effect of ACI-33 on mouse motor behavior was correlated to anti-Tau5-20 [pY18] antibodies titers in the mice sera at 7.8 months (FIG. 32, Spearman r P<0.001).

To evaluate the motoric condition of the TPLH after ACI-35 or PBS treatments, the mice were subjected to rotarod testing (FIG. 33). Although there was no significant differences between the treatment and control group, a trend for ACI-35 efficacy could be observed in the rotarod trial preformed when mice where 9.5 months old (FIG. 33, Mann-Whitney test P=0.1905 age 9.5 months).

10.3 Conclusion

ACI-33 vaccination in TPLH mice showed a beneficial effect on mouse motor deficits during rotarod trial versus PBS injected animals. This positive effect was correlated to anti-Tau antibody titers in mouse serum.

ACI-35 vaccination in TPLH mice showed a trend in efficacy on mouse motor deficits during rotarod trial at 9.5 months versus PBS injected animals.

Example 11

Anti-pTau Antibody Response in Female Nude Mice

The objective of this study was to evaluate the anti-pTau antibody response induced by injection of ACI-33 (Tau5-20 [pY18]) vaccine in female nude mice. The nude mice carry the Foxn1$^{nu}$ mutation, have a reduced T cell function due to the lack of properly functioning thymic gland. Thus, the aim of this study was to analyze whether the antibody response induced by ACI-33 is T-cell independent.

Nude mice with a C57BL/6 background and corresponding wild-type littermates at an age of 11 or 13 weeks were injected subcutaneously (s.c.) Mice were immunized 3 times with 2 week intervals and were bled 1 week after each immunization. Total anti-pTau (Tau5-20 [pY18]) peptide IgG responses were measured by ELISA. In addition, the isotype pattern of the antibody response was analyzed after 3 immunizations to evaluate the distribution of the different subclasses of IgGs as well as IgM. Antibody titers against corresponding non-pTau (Tau5-20), full-length (441aa) Tau protein and phosphorylated full-length (441aa) Tau protein were also analyzed.

To verify the absence of T-helper cells in the nude mice, the percentage of CD3$^+$/CD4$^+$ cells was evaluated by fluorescence-activated cell sorter (FACS).

11.1 Methods
11.1.1 Preparation of the Vaccine ACI-33

The ACI-33 vaccines were prepared according to EXAMPLE 3.

The liposomal suspension (batch ACI-33-090818-A) was then aliquoted prior to storage at 2-8° C. The final peptide/phospholipid molar ratio was 1:100. Vaccines were shipped to JSW Life Sciences GmbH (Austria).

11.1.2 Immunizations

At JSW Life Sciences GmbH nude mice (B6.Cg-Foxn1 nu/J) with a C57BL16 background and corresponding wild-type littermates (6 ♀ mice/group) received s.c. injections of ACI-33 on three occasions with a 2-week interval between each administration (day 0, 14, 28) according to Table 15. Plasma samples from the facial vein/artery were collected 7 days before and 2, 4, 7, 21, 35 and 56 days after the first injections. Tau5-20 [pY18]-specific IgG and IgM antibody titers and IgG isotype patterns were determined by ELISA. Specific IgG antibodies titers for non-pTau5-20, full-length (441aa) Tau protein and phosphorylated full-length (441aa) Tau protein was also determined by ELISA. Blood samples were also collected on d-7 for FACS analysis to determine the percentage of CD3+/CD4+ cells.

11.1.3 Quantification of Tau Peptide-Specific Antibodies

Specific IgG antibodies for Tau5-20 [pY18] were measured by ELISA in 5 sera bleeding samples (d2, d7, d21, d35 and d56). Tau5-20-, full-length (441aa). Tau protein- and phosphorylated full-length (441aa) Tau protein-specific IgG were determined in the sera from d35. Tau5-20 [pY18]-specific IgM and IgG isotype antibodies were determined by ELISA in the d35 sera bleeding sample. Plates were coated with 1 ug/ml of corresponding Tau peptide and 1 ug/ml of corresponding Tau protein overnight at 4° C. After washing each well with PBS. 0.05% Tween 20 and blocking with 1% BSA in PBS-0.05% Tween 20, serial dilutions of sera were added to the plates and incubated at 37° C. for 2 hours. After washing plates were incubated with an alkaline phosphatase (AP)-conjugated anti-mouse IgG total antibody (Jackson Laboratories, Baltimore, Pa., USA) or isotype specific antibodies (horseradish Peroxidase (HRP)-conjugated anti-mouse IgM, AP-conjugated anti-mouse IgG1, biotin-conjugated anti-mouse IgG3, purchased from Pharmingen BD San Diego, Calif., USA; biotin-conjugated anti-mouse IgG2a purchased from invitrogen CA, USA and HRP-conjugated anti-mouse IgG2b from Zymed Laboratories, San Francisco, Calif.) for 2 hours at 37° C. After washing plates were incubated with pNPP (para-nitro-phenyl-phosphate), the phosphatase substrate for AP, or ABTS (2,2'-azino-bis(3-ethyl-benzthiazoline-6-sulphonic acid)), the substrate for HRP and read at 405 nm using an ELISA plate reader. A supplemental step was done for the biotin conjugated antibodies where plates were incubated for 45 min in streptavidin-HRP (R&D Systems, Minneapolis, Minn., USA) before detection using ABTS. Results are expressed as O.D. (Optical Density) at a non-saturated O.D. for IgG, IgG isotypes and IgM.

11.1.4 CD3+ ICD4+ Cell Quantification

Mouse blood samples were lysed with ammonium chloride until cleared, then centrifuged at 400×g for 7 minutes and pellets were resuspended in PBS containing EDTA. Then cells were blocked with CD16/CD32 blocking reagent and stained with CD4 (PE conjugate) and CD3 (PE-Cy5) antibodies for 30 min at 4° C. Samples were washed with PBS, resuspended in fixative solution (DB Cellfix diluted 1:40 in BD FACS Flow) and acquired on a BD FACS Calibur cytometer. The percentage of gated cells, which stained positive for CD3+ and CD4+ (T-helper cells) was evaluated.

TABLE 15

Mice Immunization

| Group | Number of Animals and Gender | Treatment/ Volume[a] | Vaccine Batch | Process | Route of Administration[b] | Dose level Quantity of T1 ug/dose[c] | Quantity of MPLA ug/dose[c] |
|---|---|---|---|---|---|---|---|
| 1 | 6 ♀ nude mice | ACI-33 0.2 ml | ACI-33-090818-A | ACI-A | s.c. | 12.6 | 15.8 |
| 2 | 6 ♀ Wt mice | ACI-33 0.2 ml | ACI-33-090818-A | ACI-A | s.c. | 12.6 | 15.8 |

[a]theoretical volume
[b]s.c.: subcutaneous
[c]measured quantity determined after analysis

11.2 Results
11.2.1 General Observations

None of the animals died prematurely and no side effects due to the treatment were reported. For all E36.Cg-Foxn1nu/J animals, the typical nude phenotype was present, while the wild-type (wt) littermates had a normal fur.

11.2.2 CD3+/CD4+ Cell Quantification

CD3+/CD4+ staining followed by FACS analysis revealed significant reduction in T-helper cell counts (CD3+/CD4+ cells) in nude mice, compared to wt animals (FIG. 34).

11.2.3 Immune Response Analysis

The anti-Tau5-20 [pY18] IgG titers generated by ACI-33 vaccination were analyzed to study the immunogenicity of the vaccine in wt and nude mice. The anti-Tau5-20 [pY18] IgG titers of nude were analyzed to study whether the response induced by ACI-33 was independent on T cell function. The vaccine induced an anti-Tau5-20 [pY18] IgG response in nude mice and there was no significant difference between the antibody response induced by ACI-33 in wt or nude mice at all time points tested (FIG. 35; 2-way ANOVA $P<0.05$ for all bleedings between nude and wt mice).

ACI-33 vaccine induced in both mouse types an anti-Tau5-20 [pY18] IgG response following s.c. injection that peaked after 2 immunizations (d27) (FIG. 35).

ACI-33 vaccination induced antibody titers of the same profile for the different IgG subclass and IgM between nude and wt mice as there was no significant differences between the two mouse types following 3 s.c. immunizations of the vaccine (FIG. 36, 1-way ANOVA $P>0.05$ IgG1 nude vs. IgG1 wt, IgG2a/2b nude vs. IgG2a/2b wt, IgG3 nude vs. IgG3 wt, IgM nude vs. IgM wt). In both mouse type there was a significant lower level of IgG1 compared to IgG2b and IgM (FIG. 36, 1-way ANOVA, nude mice: $P<0.01$ IgG1 vs. IgG2b or IgM; Wt mice: $P<0.05$ IgG1 vs. IgG2b or IgM). Furthermore nude mice showed a significant lower level of IgG1 compared to IgG3 (FIG. 36, 1-way ANOVA, nude mice: $P<0.05$ IgG1 vs. IgG3) and the level of IgG2a were also lower compared to IgG2b, IgG3 and IgM (FIG. 36, 1-way ANOVA. nude mice: $P<0.05$ IgG2a vs. IgG2b, IgG3 or IgM).

IgG titers induced after 3 s.c. injection of ACI-33 were also analyzed on different Tau peptides (anti-Tau5-20 [pY18] and anti-Tau5-20) and proteins (anti-phosphorylated full-length (441aa) Tau protein=anti-pTau protein and anti-full-length (441aa) Tau protein=anti-Tau protein (FIG. 37). There was no difference in the titers on the different peptides and protein between wt and nude mice. In the nude mice group there was a significant difference in the anti-Tau5-20 [pY18] being higher then the anti-Tau5-20 titers (FIG. 37, 1-way ANOVA, $P<0.05$ anti-Tau5-20 [pY18] titers vs. anti-Tau5-20 titers).

11.3 Conclusion

Despite the small percentage of CD3+ and CD4+ cells in nude mice, ACI-33 vaccine induced a robust anti-Tau5-20 [pY18] IgG response. The persistence of the antibody response and the IgG isotype distribution were similar in wt and nude mice suggesting that these parameters are independent on T cells in the context of ACI-33 vaccination. Compared to immune-competent mice, ACI-33 immunization induced an identical antibody titer and kinetic with similar IgG profile in T cell deficient mice. Furthermore the antibody titers on the different Tau peptides and proteins were similar between immune-competent and T cell deficient mice. These data indicated that ACI-33 induced a T cell-independent antibody response in both nude and wt mice.

REFERENCE LIST

Alving et al., (1992) Infect. Immun. 60:2438-2444
Asuni et al., (2007) J. Neurosc. 27 (34), 9115-29
Hodgson et al., (1991) Bio/Technoloy, 9:421
Khaw, B. A. et al. (1982) J. Nucl. Med. 23:1011-1019
Lewis et al., (2000) Nature Genetics, 25:402-405
Masliah et al., (2005) Neuron, 46(6), 857-68
Muhs et al., (2007) Proc Natl Acad Sci USA, 104(23), 9810-5
Muyllaert et al, (2006) Rev Neurol, 162(10), 903-907
Muyllaert et al, (2008) Genes Brain Behav., Suppl. 1, 57-66
Nicolau et. al. (2002) Proc Natl. Acad. Sci. USA 99, 2332-2337
Nicoll et al., (2003) Nature Med, 9, 448-452
Oddo et al., (2004) Neuron, 43, 321-332
Queen et al., (1989) Proc. Natl Acad Sci USA, 86:10029-10032
Ribe et al., (2005) Neurobiol Dis, 20(3), 814-22
Roberson et al, (2007) Science, 316 (5825), 750-4
Rosenmann et al., (2006) Arch Neurol, 63(10), 1459-67

Rousseaux et al. Methods Enzymology, (1986), Academic Press 121:663-69

Terwel et al., (2006) J Blot Chem, 280, 3963-3973

Terwel et al, (2008) Am J pathol., 172(3), 786-98

Urushitiani et al, (2007) Proc. Natl Acad Sci USA, 104(79, 2495-500

Wagner et at (2002) Journal of Liposome Research Vol 12(3), pp 259-270

Deposits

The following hybridoma cell lines were deposited in the name of AC IMMUNE S.A. with the "Deutsche Sammlung von Mikroorganismen and Zellkulturen GmbH (DSMZ) in Braunschweig, Inhoffenstr. 7B, D-28124 Braunschweig, under the provisions of the Budapest Treaty:

| Hybridoma name | Accession number | Date of deposit |
| --- | --- | --- |
| ACI-41-Ab1 | DSM ACC3043 | Mar. 3, 2010 |
| 2B6 | DSM ACC3044 | Mar. 10, 2010 |
| 3A8 | DSM ACC3045 | Mar. 10, 2010 |
| 4C1 | DSM ACC3046 | Mar. 10, 2010 |
| 5D10A3 | DSM ACC3047 | Mar. 10, 2010 |
| 6C10 | DSM ACC3048 | Mar. 10, 2010 |
| 6H1 | DSM ACC3049 | Mar. 10, 2010 |
| 7C2 | DSM ACC3050 | Mar. 10, 2010 |

The invention claimed is:

1. An antigenic peptide obtainable from a tau protein reconstituted in a liposome, wherein the antigenic peptide is modified through linkage to a lipophilic or hydrophobic moiety that facilitates insertion into a lipid bilayer of the liposome such that the antigenic peptide is presented on the surface of the liposome, and wherein the antigenic peptide consists of an amino acid sequence selected from one of SEQ ID NO: 2 to SEQ ID NO: 9, and modified variant fragments thereof, the modified variant fragment being modified through a conservative substitution or deletion of at least one but not more than 5 amino acids.

2. The antigenic peptide of claim 1, wherein said peptide is capable of eliciting a conformation specific and/or a T-cell independent immune response.

3. The antigenic peptide of claim 1, wherein the antigenic peptide is SEQ ID NO: 5.

4. The antigenic peptide of claim 1, wherein the lipophilic or hydrophobic moiety is palmitic acid, stearic acid, myristic acid, lauric acid, oleic acid, linoleic acid, linolenic acid and cholesterol, or 1,2-distearoyl-sn-gylcero-3-phophatidylethanolamine (DSPE).

5. The antigenic peptide of claim 4, wherein the lipophilic or hydrophobic moiety is palmitic acid.

6. The antigenic peptide of claim 1, wherein the antigenic peptide is linked to at least four lipophilic or hydrophobic moieties.

7. A pharmaceutical composition comprising an antigenic peptide obtainable from a tau protein an reconstituted in a liposome and a pharmaceutically acceptable carrier, wherein the antigenic peptide is modified through linkage to a lipophilic or hydrophobic moiety that facilitates insertion into a lipid bilayer of the liposome such that the antigenic peptide is presented on the surface of the liposome, and wherein the antigenic peptide consists of an amino acid sequence selected from one of SEQ ID NO: 2 to SEQ ID NO: 9, and modified variant fragments thereof, the modified variant fragment being modified through a conservative substitution or deletion of at least one but not more than 5 amino acids.

8. The pharmaceutical composition of claim 7, wherein the antigenic peptide is SEQ ID NO: 5.

9. The pharmaceutical composition of claim 7, further comprising a pharmaceutically acceptable adjuvant, an immunomodulator, or a combination thereof.

10. A method for inducing an immune response in an animal suffering from a neurodegenerative disorder comprising administering to said animal an antigenic peptide obtainable from a tau protein and reconstituted in a liposome, wherein the antigenic peptide is modified through linkage to a lipophilic or hydrophobic moiety that facilitates insertion into a lipid bilayer of the liposome such that the antigenic peptide is presented on the surface of the liposome, and wherein the antigenic peptide consists of an amino acid sequence selected from one of SEQ ID NO: 2 to SEQ ID NO: 9, and modified variant fragments thereof, the modified variant fragment being modified through a conservative substitution or deletion of at least one but not more than 5 amino acids, and a pharmaceutically acceptable carrier.

11. The method of claim 10, wherein the pharmaceutical composition further comprises a pharmaceutically acceptable adjuvant, an immunomodulator, or a combination thereof.

12. A method for the treatment of a neurodegenerative disease or disorder comprising administering to an animal suffering from such a disease or disorder a pharmaceutical composition comprising an antigenic peptide obtainable from a tau protein and reconstituted in a liposome, wherein the antigenic peptide is modified through linkage to a lipophilic or hydrophobic moiety such that the antigenic peptide is presented on the surface of the liposome, and wherein the antigenic peptide consists of an amino acid sequence selected from one of SEQ ID NO: 2 to SEQ ID NO: 9, and modified variant fragments thereof, the modified variant fragment being modified through a conservative substitution or deletion of at least one but not more than 5 amino acids, and a pharmaceutically acceptable carrier.

13. The method of claim 12, wherein the pharmaceutical composition further comprises a pharmaceutically acceptable adjuvant, an immunomodulator, or a combination thereof.

14. The method of claim 12, wherein the disease or disorder is caused by or associated with the formation of neurofibrillary lesions.

15. The method of claim 12, wherein the disease or disorder is Alzheimer's Disease, Creutzfeldt-Jacob disease, Dementia pugilistica, Down's Syndrome, Gerstmann-Sträussler-Scheinker disease, inclusion body myositis, prion protein cerebral amyloid angiopathy, traumatic brain injury, amyotrophic lateral sclerosis/parkinsonism-dementia complex of Guam, Non-Guamanian motor neuron disease with neurofibrillary tangles, argyrophilic grain dementia, corticobasal degeneration, diffuse neurofibrillary tangles with calcification, frontotemporal dementia with parkinsonism linked to chromosome 17, Hallevorden-Spatz disease, multiple system atrophy, Niemann-Pick disease (type C), Pick's disease, progressive subcortical gliosis, progressive supranuclear palsy, Subacute sclerosing panencephalitis, Tangle only dementia, Postencephalitic Parkinsonism, or Myotonic dystrophy.

* * * * *